(12) United States Patent
Tyrrell et al.

(10) Patent No.: US 6,749,860 B2
(45) Date of Patent: Jun. 15, 2004

(54) ABSORBENT ARTICLES WITH NON-AQUEOUS COMPOSITIONS CONTAINING BOTANICALS

(75) Inventors: David John Tyrrell, Appleton, WI (US); Chantel Spring Buhrow, Weyauwega, WI (US); Beth Anne Lange, Appleton, WI (US); Duane Gerard Krzysik, Appleton, WI (US); Earl David Brock, Kimberly, WI (US); James Louis Cahall, Appleton, WI (US); Samuel Qcheng Lin, Paramus, NJ (US); Ronni Lynn Weinkauf, Oradell, NJ (US); Uma Santhanan, Tenafly, NJ (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 217 days.

(21) Appl. No.: 09/747,382

(22) Filed: Dec. 22, 2000

(65) Prior Publication Data

US 2002/0136755 A1 Sep. 26, 2002

(51) Int. Cl.⁷ .................................. A01N 25/34
(52) U.S. Cl. ........................ 424/404; 424/402
(58) Field of Search ................... 424/402, 405

(56) References Cited

U.S. PATENT DOCUMENTS

| | | |
|---|---|---|
| 3,305,392 A | 2/1967 | Britt |
| 3,489,148 A | 1/1970 | Duncan et al. |
| 3,585,998 A | 6/1971 | Hayford et al. |
| 3,724,465 A | 4/1973 | Duchane |
| 3,756,238 A | 9/1973 | Hanke |
| 3,814,101 A | 6/1974 | Kozak |

(List continued on next page.)

FOREIGN PATENT DOCUMENTS

| | | |
|---|---|---|
| CA | 2019557 A1 | 12/1990 |
| DE | 3536318 A1 | 4/1987 |
| DE | 41 36 540 A1 | 5/1992 |
| EP | 0 212 870 B1 | 7/1986 |
| EP | 0 613 675 A1 | 9/1994 |
| EP | 0 797 968 A1 | 10/1997 |

(List continued on next page.)

OTHER PUBLICATIONS

Akin, Frank J.; Lemmen, Jac T.; Bozarth, Dena L.; Garofalo, Martin J.; and Grove, Gary L.; "A refined method to evaluate diapers for effectiveness in reducing skin hydration using the adult forearm," *Skin Research and Technology*, ISSN 0909–752X, 1997, pp. 173–176.

Berg, Ronald W., Ph.D; Milligan, Michael C., M.B.A.; and Sarbaugh, Frank C.; "Association of Skin Wetness and pH with Diaper Dermatitis," *Pediatric Dermatology*, Mar., 1994, vol. 11, No. 1, pp. 18–20.

Imai, Satoshi and Kuwabara, Chihiro; Pigeon Co., Ltd., Ibaragi, Japan; "Infant Skin and Its Care," *Cosmetics & Toiletries*, vol. 107, Jul., 1992, pp. 85–86, 88–90.

(List continued on next page.)

Primary Examiner—Thurman K Page
Assistant Examiner—Sharon L. Howard
(74) Attorney, Agent, or Firm—Alyssa A. Dudkowski

(57) ABSTRACT

The present invention relates to absorbent articles including non-aqueous compositions for protecting the barrier function of the skin. The compositions can be applied to the bodyfacing surfaces of absorbent articles so that the compositions come into contact with the skin. The compositions of the invention have improved stability on the bodyfacing surfaces after processing. The compositions of the invention provide several benefits including prevention and alleviation of skin irritations associated with the use of absorbent articles. The compositions can include emollients, viscosity enhancers and extracted botanical actives.

54 Claims, 6 Drawing Sheets

U.S. PATENT DOCUMENTS

| | | |
|---|---|---|
| 3,821,350 A | 6/1974 | Suchane |
| 3,881,488 A | 5/1975 | Delanty et al. |
| 3,896,807 A | 7/1975 | Buchalter |
| 3,902,493 A | 9/1975 | Baier et al. |
| 4,040,857 A | 8/1977 | Lissant |
| 4,100,324 A | 7/1978 | Anderson et al. |
| 4,164,563 A | 8/1979 | Chang |
| 4,273,786 A | 6/1981 | Kraskin |
| 4,343,783 A | 8/1982 | Hooper et al. |
| 4,355,020 A | 10/1982 | Kuy |
| 4,355,046 A | 10/1982 | Suess |
| 4,556,560 A | 12/1985 | Buckingham |
| 4,604,313 A | 8/1986 | McFarland et al. |
| 4,613,447 A | 9/1986 | Hara et al. |
| 4,623,339 A | 11/1986 | Ciraldo et al. |
| 4,634,438 A | 1/1987 | Sustmann et al. |
| 4,634,439 A | 1/1987 | Sustmann et al. |
| 4,637,820 A | 1/1987 | Marini et al. |
| 4,655,756 A | 4/1987 | Fawkes |
| 4,657,537 A | 4/1987 | Zimmerer |
| 4,675,014 A | 6/1987 | Sustmann et al. |
| 4,685,909 A | 8/1987 | Berg et al. |
| 4,711,780 A | 12/1987 | Fahim |
| 4,732,797 A | 3/1988 | Johnson et al. |
| 4,738,678 A | 4/1988 | Paulis |
| 4,753,643 A | 6/1988 | Kassai |
| 4,753,647 A | 6/1988 | Curtis |
| 4,760,096 A | 7/1988 | Sakai et al. |
| 4,772,501 A | 9/1988 | Johnson et al. |
| 4,790,836 A | 12/1988 | Brecher |
| 4,790,840 A | 12/1988 | Cortina |
| 4,798,603 A | 1/1989 | Meyer et al. |
| 4,808,175 A | 2/1989 | Hansen |
| 4,861,405 A | 8/1989 | Kassai |
| 4,882,204 A | 11/1989 | Tenenbaum |
| 4,911,932 A | 3/1990 | Clum et al. |
| 4,931,052 A | 6/1990 | Feldman |
| 4,960,592 A | 10/1990 | Hagen et al. |
| 4,978,534 A | 12/1990 | Saitoh |
| 4,990,144 A | 2/1991 | Blott |
| 4,996,238 A | 2/1991 | Matravers |
| 5,043,155 A | 8/1991 | Puchalski et al. |
| 5,049,440 A | 9/1991 | Bornhoeft, III et al. |
| 5,091,193 A | 2/1992 | Enjolras et al. |
| 5,110,593 A | 5/1992 | Benford |
| 5,139,790 A | 8/1992 | Snipes |
| 5,141,803 A | 8/1992 | Pregozen |
| 5,147,576 A | 9/1992 | Montague et al. |
| 5,176,668 A | 1/1993 | Bernardin |
| 5,176,672 A | 1/1993 | Bruemmer et al. |
| 5,192,277 A | 3/1993 | Chung et al. |
| 5,192,606 A | 3/1993 | Proxmire et al. |
| 5,194,261 A | 3/1993 | Pichierri |
| 5,232,691 A | 8/1993 | Lemole |
| 5,244,668 A | 9/1993 | Snipes |
| 5,306,486 A | 4/1994 | McCook et al. |
| 5,336,212 A | 8/1994 | De Francesco |
| 5,336,692 A | 8/1994 | Gans et al. |
| 5,350,624 A | 9/1994 | Georger et al. |
| 5,362,488 A | 11/1994 | Sibley et al. |
| 5,364,382 A | 11/1994 | Latimer et al. |
| 5,376,655 A | 12/1994 | Imaki et al. |
| 5,384,125 A | 1/1995 | DiPippo et al. |
| 5,409,903 A | 4/1995 | Polak et al. |
| 5,436,007 A | 7/1995 | Hartung et al. |
| 5,482,765 A | 1/1996 | Bradley et al. |
| 5,486,166 A | 1/1996 | Bishop et al. |
| 5,490,846 A | 2/1996 | Ellis et al. |
| 5,496,298 A | 3/1996 | Kuepper et al. |
| 5,509,915 A | 4/1996 | Hanson et al. |
| 5,525,346 A | 6/1996 | Hartung et al. |
| 5,533,990 A | 7/1996 | Yeo |
| 5,569,230 A | 10/1996 | Fisher et al. |
| 5,578,310 A | 11/1996 | M'Timkulu et al. |
| 5,601,871 A | 2/1997 | Krzysik et al. |
| 5,605,749 A | 2/1997 | Pike et al. |
| 5,607,760 A | 3/1997 | Roe |
| 5,607,980 A | 3/1997 | McAtee et al. |
| 5,609,587 A | 3/1997 | Roe |
| 5,614,293 A | 3/1997 | Krzysik et al. |
| 5,618,529 A | 4/1997 | Pichierri |
| 5,618,850 A | 4/1997 | Coury et al. |
| 5,631,012 A | 5/1997 | Shanni |
| 5,635,191 A | 6/1997 | Roe et al. |
| 5,643,588 A | 7/1997 | Roe et al. |
| 5,643,899 A | 7/1997 | Elias et al. |
| 5,648,083 A * | 7/1997 | Blieszner et al. ............ 424/402 |
| 5,650,218 A | 7/1997 | Krzysik et al. |
| 5,652,049 A | 7/1997 | Suzuki |
| 5,652,194 A | 7/1997 | Dyer et al. |
| 5,658,559 A | 8/1997 | Smith |
| 5,665,368 A | 9/1997 | Lentini et al. |
| 5,693,037 A | 12/1997 | Lee et al. |
| 5,695,868 A | 12/1997 | McCormack |
| 5,738,859 A | 4/1998 | Posner |
| 5,801,107 A | 9/1998 | Everhart et al. |
| 5,830,487 A | 11/1998 | Klofta et al. |
| 5,843,056 A | 12/1998 | Good et al. |
| 5,849,314 A | 12/1998 | Dobkowski et al. |
| 5,855,897 A | 1/1999 | Pelle |
| 5,855,999 A | 1/1999 | McCormack |
| 5,856,245 A | 1/1999 | Caldwell et al. |
| 5,869,033 A | 2/1999 | Schulz |
| 5,869,075 A | 2/1999 | Krzysik |
| 5,869,172 A | 2/1999 | Caldwell |
| 5,871,763 A | 2/1999 | Luu et al. |
| 5,879,341 A | 3/1999 | Odorzynski et al. |
| 5,891,126 A | 4/1999 | Osborn, III et al. |
| 5,938,649 A | 8/1999 | Ducker et al. |
| 5,945,110 A | 8/1999 | Vianen et al. |
| 5,951,990 A | 9/1999 | Ptchelintsev |
| 5,989,577 A | 11/1999 | Hoath et al. |
| 5,990,377 A | 11/1999 | Chen et al. |
| 6,004,566 A | 12/1999 | Friedman et al. |
| 6,051,749 A | 4/2000 | Schulz |
| 6,075,179 A | 6/2000 | McCormack et al. |
| 6,100,442 A | 8/2000 | Samuelsson et al. |
| 6,103,245 A | 8/2000 | Clark et al. |
| 6,107,537 A | 8/2000 | Elder et al. |
| 6,117,439 A | 9/2000 | Kake |
| 6,118,041 A | 9/2000 | Roe et al. |
| 6,120,488 A | 9/2000 | VanRijswijck et al. |
| 6,136,332 A | 10/2000 | Grollier et al. |
| 6,149,934 A * | 11/2000 | Krzysik et al. ............ 424/443 |
| 6,152,906 A | 11/2000 | Faulks et al. |
| 6,153,209 A | 11/2000 | Vega et al. |
| 6,156,024 A | 12/2000 | Schulte et al. |
| 6,166,285 A | 12/2000 | Schulte et al. |
| 6,183,766 B1 | 2/2001 | Sine et al. |
| 6,217,890 B1 | 4/2001 | Paul et al. |
| 6,238,682 B1 | 5/2001 | Klofta et al. |
| 6,287,581 B1 * | 9/2001 | Krzysik et al. ............ 424/402 |
| 6,294,186 B1 | 9/2001 | Beerse et al. |
| 6,309,736 B1 | 10/2001 | McCormack et al. |
| 6,316,030 B1 | 11/2001 | Kropf et al. |
| 6,331,305 B1 * | 12/2001 | Sang ................... 424/401 |
| 6,344,218 B1 | 2/2002 | Dodd et al. |
| 6,506,394 B1 | 1/2003 | Yahiaoui et al. |
| 2001/0006666 A1 | 7/2001 | Harbeck |

FOREIGN PATENT DOCUMENTS

| EP | 0 815 841 A1 | 1/1998 |
|---|---|---|
| EP | 0 875 233 A1 | 11/1998 |
| EP | 0 922 452 A1 | 6/1999 |
| EP | 0 922 456 A1 | 6/1999 |
| EP | 1 057 476 A1 | 12/2000 |
| EP | 0 808 151 B1 | 8/2001 |
| GB | 880276 | 10/1961 |
| GB | 884688 | 12/1961 |
| GB | 2 033 751 A | 5/1980 |
| GB | 2311727 A | 10/1997 |
| JP | 10-37070 | 2/1988 |
| WO | WO 90/12555 A1 | 11/1990 |
| WO | WO 92/09289 A1 | 6/1992 |
| WO | WO 93/16670 A1 | 9/1993 |
| WO | WO 93/21878 A1 | 11/1993 |
| WO | WO 94/09757 A1 | 5/1994 |
| WO | WO 94/09796 A1 | 5/1994 |
| WO | WO 95/19190 A1 | 7/1995 |
| WO | WO 96/16681 A1 | 6/1996 |
| WO | WO 96/16682 A1 | 6/1996 |
| WO | WO 97/05908 A2 | 2/1997 |
| WO | WO 97/05909 A2 | 2/1997 |
| WO | WO 97/38735 A1 | 10/1997 |
| WO | WO 97/38738 A1 | 10/1997 |
| WO | WO 98/00858 A1 | 1/1998 |
| WO | WO 98/03147 A1 | 1/1998 |
| WO | WO 98/47546 A1 | 10/1998 |
| WO | WO 98/551559 A2 | 12/1998 |
| WO | WO 99/12530 A1 | 3/1999 |
| WO | WO 99/13861 A1 | 3/1999 |
| WO | WO 99/26610 A1 | 6/1999 |
| WO | WO 99/26618 A1 | 6/1999 |
| WO | WO 99/26619 A1 | 6/1999 |
| WO | WO 99/45771 A1 | 9/1999 |
| WO | WO 99/45973 A1 | 9/1999 |
| WO | WO 99/45974 A1 | 9/1999 |
| WO | WO 99/45976 A1 | 9/1999 |
| WO | WO 99/46316 A1 | 9/1999 |
| WO | WO 99/62478 A1 | 12/1999 |
| WO | WO 00/38747 A2 | 7/2000 |
| WO | WO 00/64407 A1 | 11/2000 |
| WO | WO 00/64501 A1 | 11/2000 |
| WO | WO 00/64503 A1 | 11/2000 |
| WO | WO 00/69481 A1 | 11/2000 |
| WO | WO 00/69482 A1 | 11/2000 |
| WO | WO 00/69483 A1 | 11/2000 |
| WO | WO 00/69484 A1 | 11/2000 |
| WO | WO 00/71177 A1 | 11/2000 |

OTHER PUBLICATIONS

Preston, Sandra L., PharmD & Bryant, Bobby G., MS, PharmD; "Etiology and Treatment of Diaper Dermatitis," *Hospital Pharmacy*, 1994, vol. 29, No. 12, pp. 1086–1088, 1097.

Sires, Ulrike I., MD & Mallory, Susan B., MD; "Diaper dermatitis," *Postgraduate Medicine*, vol. 98, No. 6, Dec., 1995, pp. 79–82, 84, 86.

Zielinski, Ruth, C.N.M., Hanson, Elizabeth, C.N.M.; "Diaper Dermatitis: Medical Aspects of Skin Care," *Nonwovens World*, Feb.–Mar., 2000, pp. 60–65.

Patent Cooperation Treaty Search Report from the International Search Authority, International Application No. PCT/US 01/50274 dated Oct. 28, 2002.

American Society for Testing Materials (ASTM) Designation: D 1321 —92, "Standard Test Method for Needle Penetration of Petroleum Waxes[1]", pp. 483–485, published Dec. 1992.

American Society for Testing Materials (ASTM) Designation: D 3236—88, "Standard Test Method for Apparent Viscosity of Hot Melt Adhesives and Coating Materials[1]", pp. 326–331, published Dec. 1988.

Federal Test Method Standard No. 191A, Method 5514, "Water Resistance of Cloth; Low Range, Hydrostatic Pressure Method", Jul. 20, 1978.

Federal Test Method Standard No. 191A, Method 5450, "Permeability to Air; Cloth; Calibrated Orifice Method", Jul. 20, 1978.

Haverback, B. J., Dyce, B.J., Gutentag, P.J. and Montgomery, D. W. (1963) "Measurement of Trypsin and Chymotrypsin in Stool." *Gasteroenterology* 44:588–597.

Barbero, G.J., Sibinga, M.S., Marino, J. M., and Seibel, R. (1966) "Stool Trypsin and Chymotrypsin. "*Amer. J. Dis. Child* 112:536–540.

"Statistical Methods in Research and Production", p. 460, edited by Owen L. Davies and Peter L. Goldsmith, published by Longman Group Limited, fourth revised edition (1984).

Patent Abstracts of Japan 02043265 A: Description of Masaru et al. , "Thixotropic Semisolid Composition."

Patent Abstracts of Japan 02053709 A: Description of Masaru et al. , "Thixotropic Semi–Solid Composition."

Patent Abstracts of Japan 06065104 A: Description of Michio, "Powder Composition for Dermatic Application Prevented From Scatterability."

Patent Abstracts of Japan 07267839 A: Description of Yoshiko et al. , "Ointment Composition Adhesive to Oral Mucosa,"

Patent Abstracts of Japan 09151112 A: Description of Yasuhiro et al., "Microemulsion Composition."

Patent Abstracts of Japan 10306039 A: Description of Christine et al. , "Solid Topical Aqueous Composition Capable of Forming Film, When Applied, and Having Gel Appearance."

Patent Abstracts of Japan 55025430 A: Description of Mikio et al. , "Thickening and Gelling Agent."

Patent Abstracts of Japan 56110611 A: Description of Mitsue et al. , "Preparation of Ointment Embrocation for Skin."

Patent Abstracts of Japan 59053409 A: Description of Susumu et al. , "Base Composition and Pharmaceutical Composition for External Use."

Patent Abstracts of Japan 59122420 A: Description of Katsuo et al. , "Local Ointment."

Patent Abstracts of Japan 59227816 A: Description of Kenji et al. , "Skin Cleaning and Wiping Agent Composition."

Patent Abstracts of Japan 60006759 A: Description of Tadashi et al. , "Water–Dispersible Resin for Cataplasm."

Patent Abstracts of Japan 61129117 A: Description of Sakahito et al. , "Aloe–Containing Cataplasm."

Patent Abstracts of Japan 61194014 A: Description of Hiroshi et al. , "Hydrophilic Base."

Patent Abstracts of Japan 63264413 A: Description of Kazuo, "Gabexate Mesylate Ointment."

American Society for Testing Materials (ASTM) Designation: D 1321–92, "Standard Test Method for Needle Penetration of Petroleum Waxes," pp. 483–485, published Dec. 1992.

American Society for Testing Materials (ASTM) Designation: D 3236–88, "Standard Test Method for Apparent Viscosity of Hot Melt Adhesives and Coating Materials," pp. 326–331, published Dec. 1988.

Federal Test Method Standard (FTMS) No. 191A, Method 5514, "Water Resistance of Cloth; Low Range, Hydrostatic Pressure Method," Jul. 20, 1978, 3 pages.

Federal Test Method Standard (FTMS) No. 191A, Method 5450, "Permeability To Air; Cloth; Calibrated Orifice Method," Jul. 20, 1978, 5 pages.

"Blue Moon Salves and Balms," Blue Moon Soaps: Herbal, Natural Bath Supplies and Gifts, Internet web page, "http://www.bluemoonsoaps.com/balm.html", viewed and printed Feb. 28, 2002, 2 pages.

"Snow Balm," Snow Pharmaceuticals, LLC, Internet web page, "http://www.snowbalm.com/intro.htm", viewed and printed Feb. 28, 2002, 3 pages.

"The Arbonne Baby Care," The White Whale, Internet web page, "http://thewhitewhale.com/babycare.htm", viewed and printed Feb. 28, 2002, 2 pages.

Barbero, G.J. et al., "Stool Trypsin and Chymotrypsin, "American Journal of Diseases of Children, vol. 112, Jul. through Dec., 1966, pp. 536–540.

Barry, B.W. and A.J. Grace,"Investigation of Semisolid Lipophilic Preparations by Small Strain and Continuous Shear Viscometry and Their Application to Texture Profile," Journal of Pharmaceutical Sciences, vol. 60, No. 6, Jun. 1971, pp. 814–820.

Boylan, James C., "Rheological Study of Selected Pharmaceutical Semisolids," Journal of Pharmaceutical Sciences, vol. 55, No. 7, Jul. 1966, pp. 710–715.

Braudo, E.E. et al., "The Effect Produced by the Green Tea Components and Tannin on the Fermentative Activity of Trypsin in Vitro," Vopr Pitan, vol. 27, Issue No. 6, Nov.–Dec. 1968, pp. 40–44. (Russian w/English summary).

Bremecker, K.D. et al., "Novel Concept for a Mucosal Adhesive Ointment," Journal of Pharmaceutical Sciences, vol. 73, No. 4, Apr. 1984, pp. 548–552.

Davies, Owen L. and Peter L. Goldsmith, editors, Statistical Methods in Research and Production, Fourth Revised Edition, published by Longman Inc., New York, 1984, p. 460.

Davis, S.S. et al., "Some Limitations of Continuous Shear Methods for the Study of Pharmaceutical Semi–Solids," Journal of Pharmacy and Pharmacology, vol. 20, Supplemental Issue, Dec. 1968, pp. 157S–167S.

Drechsler, Lee Ellen et al., "The Wipe: A Carrier of Skin Benefits," Cosmetics & Toiletries, vol. 116, No. 10, Oct. 2001, pp. 33–36, 38, 40, 42.

Eccleston, G.M. et al., "Correlation of Viscoelastic Functions for Pharmaceutical Semisolids: Comparison of Creep and Oscillatory Tests for Oil–in–Water Creams Stabilized by Mixed Emulsifiers," Journal of Pharmaceutical Sciences, vol. 62, No. 12, Dec. 1973, 1954–1961.

Eccleston, G.M., "Structure and Rheology of Cetomacrogol Creams: The Influence of Alcohol Chain Length and Homologue Composition," Journal of Pharmacy and Pharmacology, vol. 29, No. 3, Mar. 1977, pp. 157–162.

Eros, I. and A. Thaleb, "Rheological Studies of Creams: I. Rheological Functions and Structure of Creams," Acta Pharmaceutica Hungarica, vol. 64, No. 3, May 1994, pp. 101–103.

Fuhrer, C., "Gel Structure of Fatty Alcohols in Ointment Bases," Pharmazie, vol. 26, No. 1, Jan. 1971, pp. 43–5. (German).

Haverback, Bernard J. et al., "Measurement of Trypsin and Chymotrypsin in Stool: A Diagnostic Test for Pancreatic Exocrine Insuffieciency," Gastroenterology, vol. 44, 1963, pp. 588–597.

Huttenrauch, R., "Activation Energies in Plastic Deformation of Ointment Gels," Pharmazie, vol. 28, No. 4, Apr. 1973, 244–249. (German).

Kedzierewicz, F. et al., "Preparation of Silicone Microshperes by Emulsion Polymerization: Application to the Encapsulation of a Hydrophilic Drug," Journal of Microencapsulation, vol. 15, No. 2, Mar.–Apr. 1998, pp. 227–236.

Muguet, V. et al., "Formulation of Shear Rate Sensitive Multiple Emulsions," Journal of Controlled Release, vol. 70, No. 1–2, Jan. 29, 2001, pp. 37–49.

Odio, Mauricio R. et al., "Continuous Topical Administration of a Petrolatum Formulation by a Novel Disposable Diaper. 1. Effect on Skin Surface Microtopography," Dermatology, 2000; 200(3):232–237.

Odio, Mauricio R. et al., "Continuous Topical Administration of a Petrolatum Formulation by a Novel Disposable Diaper. 2. Effect on Skin Condition," Dermatology, 2000; 200(3):238–243.

Pena, Lorraine E. et al., "Structural Rheology of a Model Ointment," Pharmaceutical Research, vol. 11, No. 6, Jun. 1994, pp. 875–881.

Popovici, Iuliana et al., "The Physico–Chemical Characterization and Therapeutic Evaluation of Cicatrol," Revista Medico–Chirurgicala Societatii Medici si Naturalisti din Lasi, vol. 96, No. 1–2, Jan.–Jun. 1992, pp. 57–64.

Salo, D.P. et al., "Ion Exchange Properties of Clay Minerals and Its Use for Obtaining Clays with Planned Properties. 3. Effect of the Nature of Exchange Kation on the Structure–Mechanical Properties of Suspensions and Ointment Bases Prepared From Clays of Montmorillonite and Sepiolite–Mountain Leather Groups," Farm Zh, vol. 23, No. 6, 1968, pp. 61–66. (Ukrainian).

Taleb, A. and I. Eros, "Rheological Studies of Creams. II. Effect of Water Content on Rheological Characteristics," Acta Pharmaceutica Hungarica, vol. 66, No. 2, Mar. 1996, pp. 71–76.

Tamburic, S. et al., "An Investigation Into the Use of Thermoheology and Texture Analysis in the Evaluation of W/O Creams Stabilized With a Silicone Emulsifer," Pharmaceutical Development Technology, vol. 1, No. 3, Oct. 1996, pp. 299–306.

Vinson, Joe and John Proch, "Inhibition of Moisture Penetration to the Skin by a Novel Incontinence Barrier Product," Journal of Wound Ostomy Continence Nursing, vol. 25, No. 5, Sep. 1998, pp. 256–260.

* cited by examiner

ABSORBENT ARTICLES WITH NON-AQUEOUS COMPOSITIONS CONTAINING BOTANICALS

FIELD OF THE INVENTION

The present invention relates to the inclusion of non-aqueous compositions that contain botanical compounds on the bodyfacing materials of disposable absorbent articles, such as diapers, training pants, adult incontinence products, underpants, feminine care products, nursing pads, wound dressings and similar articles having absorbent capacity. The present invention also relates to improving skin health through delivery of non-aqueous compositions containing botanicals from the bodyfacing materials of disposable absorbent articles to the skin. Prior to delivery to the skin, the compositions are stable on the bodyfacing materials. Compositions of the invention have improved transfer from the bodyfacing materials of disposable absorbent articles to the skin. The compositions of the invention can also improve skin health when they are incorporated into other skin-contacting materials such as tissues, wet wipes and cosmetic cleansing or buffing pads.

BACKGROUND OF THE INVENTION

The stratum corneum is the outer-most layer of the skin and is responsible for regulating skin water levels and functioning as a barrier against chemicals and other stress agents found in the environment. The complex arrangement of lipids in the intercellular space of the stratum corneum is responsible for the establishment of normal barrier function. Multi-layered structures of cholesterol, ceramides and fatty acids, as well as some other minor lipids, provide the major barrier to the transport of substances into or through the skin. The overall structure of the stratum corneum acts as the frontline barrier to the skin. The link between skin barrier function and skin health is apparent from the skin inflammation caused by lipid extraction from the skin. That is, when skin barrier function is impaired, the other layers of the skin can be injured and have a response to that injury in the form of inflammation.

A variety of commercially available products contain "botanicals". "Botanical" is typically used to refer to a substance, extract or derivative of a plant. Though some botanicals are exotic, many botanicals are sourced from very common, well-known plants. Botanicals having been extensively used to distinguish and add perceived value to personal care products such as shampoos, hand lotions, facial creams, cosmetics and related types of products. In addition to personal care products, botanicals have been a boon to the vitamin and nutritional supplement area where they are often described as "herbals".

In the area of skin health, it is known to apply lipid-containing compositions to the skin in order to enhance the barrier function of the stratum corneum. This approach is disclosed in U.S. Pat. No. 5,643,899 issued to Elias et al. on Jul. 1, 1997. For some time, those of skill in the art have believed that it is necessary to apply all three of the lipid components of the stratum corneum (cholesterol, ceramides and fatty acids) to the skin in order to replenish and repair the skin and in order to not affect the normal repair processes of the skin. In particular, ceramides are believed to be very important. In fact, the art teaches that if fewer than all three of the components are used in a skin composition, the composition could actually compromise or delay repair of the barrier.

In U.S. patent application Ser. No. 09/379,928 filed Aug. 24, 1999, various compositions for improving skin health are described, including compositions suitable for use in conjunction with absorbent articles. The compositions in patent application Ser. No. 09/379,928 were found to provide benefits for skin health. The compositions were described as containing a variety of potential components and, in some forms, the compositions included natural fats and oils, sterols and sterol derivatives, humectants and surfactants. These compositions have been found to improve skin health even though they do not necessarily include any ceramides. Efficacy without ceramides was unexpected. Though the exact mechanism of functionality was not known, one hypothesis was that an emulsion of the lipid components (natural fats/oils and sterols/sterol derivatives) was formed in the humectant component (through the use of a surfactant). In some of the aspects that were described, the humectant was glycerin. Incorporation of such an emulsion into an ointment formulation was predicted to be more easily absorbed or taken up by the skin. The ointment formulation, which could include petrolatum, would form an occlusive film on the skin, thereby trapping water between the skin and the occlusive film. The trapped water was predicted to facilitate uptake of the emulsion and, therefore, the natural fats/oils and sterols, by the skin. Therefore, the humectant and surfactant components of the compositions were perceived to be facilitating the transfer of the lipid components to the skin.

Therefore, benefits and improvements to skin health have been observed when compositions containing the lipids naturally present in the stratum corneum are applied to the skin. Though the exact mechanisms are not known, one hypothesis is that the lipids being applied with the compositions are replenishing lipids that have been lost from the stratum corneum as a result of physical or biological insults. Another hypothesis is that the lipids being applied with the compositions are providing additional lipids to the stratum corneum resulting in better protection against insults. The stratum corneum of the skin is constantly exposed to physical and biological insults that could have a negative effect on barrier function.

Absorbent articles such as diapers, training pants, incontinence products and feminine care products are worn such that they are in direct contact with the skin of the wearer. An unavoidable consequence of the use of absorbent articles is that the skin is exposed more directly to various physical and biological insults. Consequently, the barrier function of the skin covered by the absorbent article is put at risk. In order to provide disposability, absorbent articles are primarily constructed of nonwoven materials. Even though nonwoven materials are engineered to have soft hand and drape, they rub against the skin and there is friction. Such friction constitutes one form of physical insult to the skin barrier. Friction against the skin barrier also occurs with the use of absorbent tissues and wipes. Absorbent tissue and wipe products are frequently used for cleansing the skin areas covered by absorbent articles. Absorbent tissue and wipe products are necessary for removing biological waste materials from the skin.

In addition to these physical insults, skin covered by absorbent articles is also frequently exposed to biological insults. Biological fluids, such as urine, feces, vaginal secretions and nasal secretions, may contain a variety of components that can damage the skin barrier. Examples of these components include proteases, lipases and bile acids. Once the skin barrier is compromised, these components, in addition to other constituents of biological fluids, can initiate or exacerbate inflammation of the skin.

Diaper dermatitis is a genre of skin conditions that, in large part, originate from impaired skin barrier function. Impairment of the skin barrier can result from a variety of factors, including: increased skin hydration due to the occlusion of the skin caused by diapers, enzymatic skin damage due to fecal and urinary enzymes, and physical damage caused by friction against the diaper surface and repeated cleaning of the skin with absorbent tissues or wet wipes.

Excessive hydration of the skin also has a negative effect on the skin barrier. The hydration level of diapered skin, for example, may reach between five to ten times that of undiapered skin. Frequent contact of diapered skin with urine may also contribute to increased skin hydration. Increased skin hydration disrupts skin lipid organization in the stratum corneum. This disruption may increase the permeability of the skin to irritants from feces and urine, thus increasing the risk of skin inflammation.

Disposable absorbent articles such as diapers, training pants, adult incontinence products, absorbent under pants, feminine care products and nursing pads have been used to absorb body fluids and leave the skin dry. Disposable absorbent articles of this type generally include a liquid impermeable backsheet member, an absorbent core or assembly, and a liquid permeable body facing or liner material. The body facing or liner material comes into contact with the wearer's skin. While the body facing material is made of a soft, compliant material, the material rubs against the skin during use and may not leave the skin completely dry and free of the bodily fluids, such as solid or semi-solid waste, the absorbent article is trying to absorb. During frequent insults of bodily fluids and frequent use of disposable absorbent articles, the skin can become irritated and appear red and be sore to the touch.

Creams, lotions or ointments can be used to provide an artificial hydrophobic barrier on the skin and to treat skin conditions such as diaper rash. Application of these types of products to the skin is often messy and inconvenient. Often, these products are not used prophylactically and are only used when signs of diaper rash are visible.

Diaper liners and other bodyfacing materials may be treated with emollients, such as petrolatum, that can be transferred to the skin through normal diapering practices. Once transferred to the skin, diaper liner formulations may provide an artificial barrier against feces and urine. These formulations may require high concentrations of petrolatum to ensure sufficient transfer to the skin to provide a benefit. High concentrations of petrolatum can be messy, greasy to the touch, and may impair the fluid handling properties of an absorbent article, such as a diaper. The slow penetration of petrolatum into the skin can lead to smearing of the agent over the skin and onto clothes and other materials.

Formulations, such as those containing petrolatum, are applied to the bodyfacing materials of absorbent articles during manufacture. In order to process and apply the formulations to the bodyfacing materials, the formulations need to be in a semi-solid or fluid state. However, in order to have stability on the bodyfacing material after manufacture, the formulations need to be semi-solid or solid across a wide range of shipping and storage temperatures. Not all of the presently known formulations are sufficiently stable on the bodyfacing materials. Consequently, such formulations may transfer off of the bodyfacing material prematurely or the formulations may migrate away from the skin-facing surfaces of the materials.

Other compositions are known for treating skin irritations, such as diaper rash. For example, U.S. Pat. No. 5,869,033 issued to Schulz on Feb. 9, 1999 describes organophilic clays as being effective for inactivating irritating fecal proteolytic enzymes. The Schulz patent describes organophilic clays as clays that have been treated with long-chain organic amphiphilic compounds such as long-chain quaternary amines so as to result in the exchange of alkali metal ions by cationic organic molecules to render the clay organophilic. Therefore, the clays described as being capable of adsorbing and inactivating fecal enzymes in the Schulz patent are modified clays. The Schulz patent describes hydrophilic clays such as montmorillonite, bentonite, beidellite, hectorite, saponite and stevensite as suitable thickeners for vehicles that include the organophilic clays. The Schulz patent does not, however, recognize any anti-irritation benefit of hydrophilic clays. Though hydrophobic vehicles are described as being suitable vehicles for the organophilic clays, the Schulz patent discourages the use of vehicle compounds having relatively long hydrocarbon chains (C-8 and longer) because of their interaction with the organophilic clays that causes the organophilic clays to have diminished adsorptive capability for fecal enzymes.

In U.S. patent application Ser. No. 09/475,535 filed Dec. 30, 1999, compositions for use in conjunction with absorbent articles are taught. The compositions include unmodified clays for the purpose of sequestering skin irritants such as fecal enzymes. The Ser. No. 09/475,535 application recognizes an efficacy for unmodified clays that was not disclosed or suggested by the Schulz patent. Further, the Ser. No. 09/475,535 application teaches unmodified clays as having sequestering activity in compositions containing long hydrocarbon chains of C-8 or longer.

Thus, what is needed is a topically effective composition delivered from a bodyside or bodyfacing material of an absorbent article that protects, maintains, recovers or otherwise benefits skin barrier function against physical damage and irritants in biological fluids. It would also be desirable to provide a topical composition delivered from a bodyside material of an absorbent article that absorbs into the skin, is non-greasy and cosmetically acceptable to the consumer. Additionally, it would be desirable to provide a topical composition having improved stability on the bodyside material of an absorbent article. Further, it would be desirable to provide a topical composition delivered from a bodyside material of an absorbent article that does not impair the waste containment functions of the absorbent article.

SUMMARY OF THE INVENTION

In response to the difficulties and problems discussed above, compositions and the use of those compositions on absorbent articles for protecting the skin barrier and subduing the inflammatory response of the skin have been discovered. The compositions of the invention provide several benefits associated with barrier function including protecting the skin barrier and subduing the inflammatory response of the skin barrier. While the compositions of the inventions can have a variety of applications, the compositions are particularly beneficial when used in conjunction with absorbent articles such as diapers, incontinence garments, feminine care products, training pants, diaper pants, nursing pads and wound dressings. Additionally, the compositions of the invention could also provide benefits when used in conjunction with tissue, pre-moistened wipe products and cosmetic cleansing and buffing pads. A further benefit of the compositions of the invention is that the compositions show improved transfer from the absorbent articles to the skin. The purposes and advantages of the present invention will be set forth in and apparent from the description that follows, as well as will be learned by practice of the invention. Additional advantages of the invention will be realized and attained by the compositions and articles particularly pointed out in the written description and claims hereof, as well as from the appended drawings.

In one aspect, the present invention relates to an absorbent article that includes an outer cover, a bodyside liner, an absorbent body and a composition. The bodyside liner is typically liquid permeable and defines a bodyfacing surface. The bodyside liner is connected in a generally superposed relation to the outer cover. The absorbent body is located between the bodyside liner and the outer cover. The composition is on a portion or the entire bodyfacing surface of the bodyside liner. The composition can be generally solid, semi-solid or liquid. The composition may be in a variety of forms, including, but not limited to, emulsions, lotions, creams, ointments, salves, suspensions, gels and the like. The composition can be applied to the bodyside liner using a variety of techniques including foam application, spraying, slot coating and printing. The present invention also encompasses technology that would permit integration of the composition directly with fibers or other materials used to form the bodyside liner. The compositions can be applied to the bodyfacing surface in amounts of from about 0.1 grams per meter squared ($g/m^2$) to about 30 $g/m^2$. The compositions of the invention could also be applied to or be present on other skin contacting surfaces of absorbent articles such as the waist and leg elastics and the containment flaps.

The compositions of the invention can include from about 5 to about 95 percent by weight of one or more emollients. Emollients are skin conditioning ingredients that help to soften, smooth, plasticize, lubricate, moisturize, improve the appearance of, improve the feel of and protect the skin. More specifically, the compositions include from about 20 to about 75 percent by weight of emollient(s). Even more specifically, the compositions include from about 40 to about 60 percent by weight of emollient(s). Suitable emollients include petroleum based oils, petrolatum, vegetable oils, hydrogenated vegetable oils, animal oils, hydrogenated animal oils, mineral oils, alkyl dimethicones, alkyl methicones, alkyldimethicone copolyols, phenyl silicones, alkyl trimethylsilanes, dimethicone, lanolin and its derivatives, esters, branched esters, glycerol esters and their derivatives, propylene glycol esters and their derivatives, alkoxylated carboxylic acids, alkoxylated acids, fatty alcohols, triglycerides, alkyl hydroxystearates and mixtures of such compounds.

The compositions of the invention also include from about 5 to about 95 percent by weight of one or more solidifying agents. More specifically, the compositions include from about 25 to about 75 percent by weight of solidifying agents. Even more specifically, the compositions include from about 40 to about 60 percent by weight of solidifying agents. A solidifying agent is a material capable of solidifying the composition so that the composition is solid at room temperature and has a penetration hardness of at least 5 mm. More specifically, the solidifying agent includes one or more materials that are capable of solidifying the natural fats/oils and emollient combination so as to have a penetration hardness of 5 to about 365 mm at 25° C. Further, the solidifying agent solidifies the emollient (or the fat/oil/emollient combination when fats and oils are used in the composition) so that it has a melting point between 32° C. and 100° C. One or more solidifying agents can be selected from alkyl siloxanes (with a melting point greater than 35° C.), polymers, waxes (animal, vegetable or mineral), synthetic waxes, hydrogenated vegetable/animal oils having a melting point of 35° C. or greater, fatty acid esters and branched esters having a melting point of 35° C. or greater, alkyl hydroxystearates ($>C_{16}$), alkoxylated alcohols and alkoxylated carboxylic acid.

Examples of suitable solidifying agents include, but are not limited to, the following compounds: alkyl silicones, alkyl trimethylsilanes, beeswax, behenyl behenate, behenyl benzoate, $C_{24}$–$C_{28}$ alkyl dimethicone, $C_{30}$ alkyl dimethicone, cetyl methicone, stearyl methicone, cetyl dimethicone, stearyl dimethicone, cerotyl dimethicone, candelilla wax, carnauba, synthetic carnauba, PEG-12 carnauba, cerasin, hydrogenated microcrystalline wax, jojoba wax, microcrystalline wax, lanolin wax, ozokerite, paraffin, synthetic paraffin, cetyl esters, behenyl behenate, $C_{20}$–$C_{40}$ alkyl behenate, $C_{12}$–$C_{15}$ lactate, cetyl palmitate, stearyl palmitate, isosteryl behenate, lauryl behenate, stearyl benzoate, behenyl isostearate, cetyl myristate, cetyl octanoate, cetyl oleate, cetyl ricinoleate, cetyl stearate, decyl oleate, di-$C_{12}$–$C_{15}$ alkyl fumerate, dibehenyl fumerate, myristyl lactate, myristyl lignocerate, myristyl myristate, myristyl stearate, lauryl stearate, octyldodecyl stearate, octyldodecyl stearoyl stearate, oleyl arachidate, oleyl stearate, tridecyl behenate, tridecyl stearate, tridecyl stearoyl stearate, pentaerythrityl tetrabehenate, pentaerythritylhydrogenated rosinate, pentaerythrityl distearate, pentaerythrityl tetraabeite, pentaerythrityl tetracocoate, pentaerythrityl tetraperlargonate, pentaerythrityl tetrastearate, ethylene vinyl acetate, polyethylene, hydrogenated cottonseed oil, hydrogenated vegetable oil, hydrogenated squalene, hydrogenated coconut oil, hydrogenated jojoba oil, hydrogenated palm oil, hydrogenated palm kernel oil, hydrogenated olive oil, polyamides, metal stearates and other metal soaps, $C_{30}$–$C_{60}$ fatty alcohols, $C_{20+}$ fatty amides, polypropylene, polystyrene, polybutane, polybutylene terephthalate, polydipentane, polypropylene, zinc stearate, dodecyl laurate, stearyl palmitate, octadecyl hexadecanoate, octadecyl palmitate, stearyl behenate, docosyl octanoate, tetradecyl-octadecanyl behenate, hexadecyl-cosanyl hexacosanate, shellac wax, glycol montanate, fluoranated waxes, $C_{20}$–$C_{40}$ alkyl hydroxystearyl stearate and mixtures of such compounds. Examples of suitable branched esters include tetradecyl-octadecanyl behenate and hexadecyl-cosanyl-hexacosanate.

In addition to the components already described, the compositions of the invention may further include from about 0.1 to about 40 percent by weight of one or more compounds acting as viscosity enhancers that increase the meltpoint viscosity of the emollients of the composition. More specifically, the compositions include from about 5 to about 20 percent by weight of one or more viscosity enhancers. Even more specifically, the compositions include from about 10 to about 15 percent by weight of viscosity enhancer(s). The viscosity enhancer increases the meltpoint viscosity of the compositions to have a high viscosity under low shear and at the "hot box car" stability temperature of approximately 54.5° C. Having high viscosity (>50,000 centipoise) at elevated temperatures prevents the compositions from migrating into or away from the materials to which they are applied. However, the viscosity enhancer component also provides a low viscosity (<5,000 centipoise) for the compositions under high shear and at processing temperatures. The viscosity enhancers of the invention are capable of providing a desirable viscosity, depending on shear and temperature conditions, for compositions having a range of melting points. While it is desirable for compositions of the invention to have increased viscosity under "hot box car" stability conditions, the increased viscosity can be maintained, in part, through the use of one or more viscosity enhancers up to the melting point of the particular composition. Typically, process temperatures are approximately 5° C. above the melting point of the composition. Examples of suitable viscosity enhancers include polyolefin resins, lipophilic/oil thickeners, ethylene/vinyl acetate copolymers, organically modified clays, polyethylene, silica, silica silylate, silica methyl silylate, colloidal silicone dioxide, alkyl hydroxy ethyl cellulose, other organically modified celluloses, PVP/decane copolymer, PVM/MA decadiene crosspolymer, PVP/eicosene copolymer, PVP/hexadecane copolymer, microcrystalline wax, hexadecyl-cosanyl-hexacosanate, shellac wax, glycol montanate, PEG-12 carnauba, synthetic paraffin, ozokerite, C20–C40 alkyl hydroxystearyl stearate, polyperfluoromethylisopropylether montan wax and mixtures of these compounds. Many of the solidifying agents, also described herein, have been found to provide the same benefits to the compositions of the invention as the viscosity enhancers.

The viscosity enhancers are selected to influence the rheological properties of the compositions. For example, one or more viscosity enhancers can be selected so that the composition has a viscosity of greater than about 50,000 centipoise at temperatures of about 55° C. and lower under low shear. Additionally, one or more viscosity enhancers can be selected so that the composition has a viscosity less than about 5,000 centipoise at temperatures of about 60° C. and higher under shear for processing conditions.

The compositions of the invention can also include from about 0.1 to about 10 percent by weight of one or more extracted botanical actives. More specifically, the compositions can include from about 0.5 to about 8 percent by weight of one or more extracted botanical actives. Even more specifically, the compositions include from about 1 to about 5 percent by weight of extracted botanical actives. The extracted botanical actives, in combination with the other components of the composition, provide several benefits to the skin, particularly skin that is frequently covered by an absorbent article and that is exposed to biological insults. Extracted botanical actives can include any water-soluble or oil-soluble active extracted from a particular plant. Examples of suitable extracted botanical actives are actives extracted from echinacea, yucca glauca, willow herb, basil leaves, Turkish oregano, carrot root, grapefruit fruit, fennel fruit, rosemary, thyme, blueberry, bell pepper, black tea, blackberry, black currant fruit, Chinese tea, coffee seed, dandelion root, date palm fruit, gingko leaf, green tea polyphenols (i.e. including epicatechin gallate and epigallocatechin 3-O-gallate), hawthorn berries, licorice, oolong tea, sage, strawberry, sweet pea, tomato, vanilla fruit, neohesperidin, quercetin, rutin, morin, myricetin, chlorogenic acid, glutathione, glycyrrhizin, absinthe, arnica, centella asiatica, chamomelle, comfrey, cornflower, horse chestnut, ivy (*Herdera helix*), magnolia, mimosa, oat extract, pansey, scullcap, seabuckthorn, white nettle, witch hazel and any combinations thereof. Particular benefits have been observed with compositions including echinacea, yucca glauca, green tea, black tea, oolong tea and willow herb. Echinacea actives may be obtained from the following echinacea species: *Echinacea angustifolia, Echinacea purpurea*, and *Echinacea pallida*. Varieties of black tea include Flowery Orange Pekoe, Golden Flowery Orange Pekoe and Fine Tippy Golden Flowery Orange Pekoe. Varieties of green tea include Japanese and Green Darjeeling.

Botanicals are primarily extracts of the plants from which they originate and botanicals are available from suppliers as part of a composition that also contains an extracting solvent. Amounts of the botanicals in the compositions of the invention in terms of active component (not extract) may range from about 0.000001 to about 10% by weight. Desirably, the amount of active botanical is from about 0.00001 to about 5% and more desirably from about 0.0001 to about 1% by weight of the composition. Further, it is also desirable that the amount of active botanical is from about 0.0001 to about 0.5% of the composition and more desirably from about 0.001 to about 0.1% by weight of the composition.

Sometimes it is necessary for the compositions of the invention to include additional components that can be used to emulsify or suspend the extracted botanical active with the rest of the composition. If the extracted botanical active is not properly incorporated into the composition, it may not have the bioavailability to provide benefits to the skin. In addition to modifications to the formulation, extracted botanical actives can also be better incorporated through the use of processing techniques. For compositions of the invention including Echinacea, it may be necessary to add an emulsifying agent such as an emulsifier having an HLB less than 7. An appropriate emulsifying agent is ABIL EM90 emulsifier available from Goldschmidt AG of Germany. Other appropriate emulsifiers include sorbitan monooleate, sorbitan sesquioleate, sorbitan trioleate and glycerol monooleate. The Echinacea can also be better incorporated into the composition by using high shear in processing or a suitable viscosity enhancer. Another option for dispersing a botanical such as Echinacea is to first blend the botanical with a hydrophilic solvent such as water, propylene glycol, butylene glycol or glycerol. Dispersing the botanical in a hydrophilic solvent and using an emulsifying agent to incorporate the solvent into the remainder of the composition provides the botanical in a "bioavailable" form in which it can contribute to protecting the skin barrier and subduing the inflammatory response of the skin.

For the reasons described above, emulsifiers, particularly those of HLB below 7, may be useful for purposes of the present invention at levels to from about 0.1 to about 10% by weight. Suitable emulsifiers include alkoxylated $C_8$–$C_{30}$ fatty acids and fatty alcohols. Examples of such emulsifiers are polyoxyethylene (2) lauryl ether, polyoxyethylene (3) monostearate, polyoxyethylene (6) cetyl ether and polyoxyethylene (5) stearyl ether and Myreth-3-Myristate (CTFA name) available commercially as "Cetiol 1414-E®". Other suitable emulsifiers included cetyl phosphate salts and dimethicone copolyol, the latter commercially available as ABIL EM90 emulsifier from Goldschmidt AG of Germany. Phosphatides such as lecithin may also be useful as emulsifiers in the compositions of the invention.

The compositions of the invention can also include from about 0.1 to about 95 percent by weight of natural fats or natural oils that contain essential and non-essential fatty acids. More specifically, the compositions can include from about 5 to about 75 percent by weight of natural fats or natural oils. Desirably, the compositions of the invention include from about 10 to about 50 percent by weight of natural fats, natural oils or mixtures of both. Natural fats and oils include fats, oils, essential oils, fatty acids, fatty alcohols, phospholipids and mixtures of these compounds. The natural fats and oils can be similar to the lipids that are present in healthy skin in order to mimic the naturally present lipids. Synthetic or synthetically modified fats and oils could potentially also be used if they functioned in the same manner as their natural counterparts. Examples of fats and oils include Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lanolin, Lanolin Alcohol, Lauric Acid, Palmitic Acid, Stearic Acid, Linoleic Acid, Stearyl Alcohol, Lauryl Alcohol, Myristyl Alcohol, Behenyl Alcohol, Rose Hip Oil, Calendula Oil, Chamomile Oil, Eucalyptus Oil, Juniper Oil, Sandlewood Oil, Tea Tree Oil, Sunflower Oil, Soybean Oil and mixtures thereof.

The compositions can also include sterols, sterol derivatives or mixtures of both in an amount of from about 0.1 to about 10 percent by weight. Sterols and sterol derivatives include compounds such as β-sterols with a tail on the 17 position and no polar groups, such as cholesterol, $C_{10}$–$C_{30}$ cholesterol/lanosterol esters, tall oil sterols, soy sterols, sterol esters and mixtures of these compounds. More specifically, the compositions include from about 0.5 to about 5 percent by weight of sterols, sterol derivatives or mixtures of both. Even more specifically, the compositions include from about 0.8 to about 1 percent by weight of the sterol compounds. Examples of suitable sterol compounds include cholesterol, sitosterol, stigmasterol, and ergosterol, as well as, $C_{10}$–$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, "AVOCADIN" (available from Croda Ltd. of Parsippany, N.J.), sterol esters and mixtures thereof.

In addition to one or more viscosity enhancers, the compositions of the invention may also include one or more rheology modifiers. Rheology modifiers are compounds that increase the viscosity of the compositions at lower temperatures as well as process temperatures. Rheology modifiers or suspending agents also provide "structure" to the compositions to prevent settling out (separation) of insoluble and partially soluble components. Other components or additives of the compositions may effect the temperature viscosities/rheologies of the compositions. By increasing the viscosity at process temperatures, the rheology modifiers will increase the low shear viscosity above 50,000 centipoise. However, the rheology modifiers are thixotropic in behavior; therefore, their viscosity decreases as shear and pressure increases. Consequently, when the rheology modifiers are used in the compositions of the invention, they maintain the suspension of insoluble and partially soluble components. This capability can be particularly important if, during processing, the composition must be left stagnant in process lines and hoses. The rheology modifiers will maintain the suspension of the insoluble and partially soluble components for a period of time that depends on the viscosity of the composition and on the amount of rheology modifier present. The thixotropic behavior of the rheology modifiers causes their viscosity to drop when processing is resumed and the composition is no longer stagnant due to the application of pressure and shear forces. In addition to stabilizing the suspension of insoluble and partially soluble components, the rheology modifiers of the invention also help to stabilize the compositions on the bodyfacing or other materials to which the compositions are applied. Examples of suitable rheology modifiers include silica, silica silylate, silica methyl silylate, quaternary starch compounds, quaternary modified clays, organically modified clays and mixtures thereof. Such rheology modifiers can help maintain the suspension of an insoluble emollient, such as a siloxane, particulates such as microencapsulates, clays and inorganic materials or an insoluble extracted botanical active, such as Echinacea, within the composition. The compositions of the invention can include from about 0.5 to about 20 percent by weight of one or more rheology modifiers.

The use of one rheology modifier, or more than one rheology modifier, such as an organically modified clay in combination with a silica, can provide a benefit to the rheology of the compositions of the invention by increasing the viscosity of the compositions at process temperatures. When a silica, an organically modified clay or both are used in an ointment or lotion type composition, it is expected that they will increase the hardness of the composition and, consequently, have a potentially negative effect on transfer of the ointment to the skin. However, when a natural clay or a synthetic analog of a natural clay is used in combination with an organically modified clay or a silica, there is an unexpected, synergistic enhancement of the rheology of the composition. The organically modified clay and silica assist the suspension of the natural clay/synthetic analog of a natural clay in the compositions of the invention. While the penetration hardness of the composition increases, the transfer of the composition is not affected due to rheology enhancement and, in many instances, the transfer is increased. When a natural clay or synthetic analog of a natural clay is combined with an organically modified clay or a silica, a small amount of shear (such as rubbing) will unexpectedly cause the composition to become soft and to spread easily. Therefore, when such a combination is used in the compositions of the invention, there is an improvement in the transfer of the composition from the bodyside liner of the article to the skin. Though these compositions provide improved transfer from the liner to the skin, they remain stable on the bodyside liner under storage conditions. Natural clays include montmorillonite, bentonite, beidellite, hectorite, saponite, stevensite, magnesium aluminum silicate and similar clays. Synthetic analogs of natural clays, such as LAPONITE synthetic clay available from Southern Clay Products, Inc. of Gonzales, Tex. can also be used to provide the rheology benefit to compositions of the invention when used in combination with organically modified clays or silica.

As will be described later in further detail, the compositions of the invention are suspected to improve the health of skin frequently occluded by absorbent articles through several mechanisms. One mechanism of action is believed to be the inhibition of enzymes present in the various forms of biological insults, namely proteases and lipases. Through inhibition of such enzymes, the compositions can protect the skin barrier by "deactivating" those substances that can deteriorate the skin barrier. Another mechanism of action is believed to be interaction of the compositions with the stratum corneum to provide a protective barrier against irritant entrance. A further mechanism of action is believed to be a subduing of the inflammatory response of the skin. Because several botanicals and their extracts are believed to have an antioxidant effect, it is believed that they are capable of reducing and preventing inflammation of the skin.

In addition to the components already described, the compositions of the invention may also include active ingredients such as those ingredients that may be useful for treating skin irritations such as diaper rash. Examples of such active ingredients include allantoin and its derivatives, aloe, aluminum hydroxide gel, calamine, cocoa butter, cod liver oil, dimethicone, glycerin, kaolin and its derivatives, lanolin and its derivatives, mineral oil, petrolatum, shark liver oil, talc, topical starch, zinc acetate, zinc carbonate, zinc oxide and mixtures of these ingredients. Some of the ingredients listed as possible active ingredients for treating the skin can also be used as emollients.

In order to enhance or increase the function of the compositions of the invention, additional ingredients may be added. Examples of the classes of ingredients along with their functions include: antifoaming agents (reduce the tendency of foaming during processing); antimicrobial actives; antifungal actives; antiseptic actives; antioxidants (product integrity); antioxidants-cosmetic (reduce oxidation); astringents-cosmetic (induce a tightening or tingling sensation on skin); astringent-drug (a drug product that checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); other emollients (help to maintain the soft, smooth, and pliable appearance of the skin by their ability to remain on the skin surface or in the stratum corneum to act as lubricants, to reduce flaking, and to improve the skin's appearance); external analgesics (a topically applied drug that has a topical analgesic, anesthetic, or antipruritic effect by depressing cutaneous sensory receptors, or that has a topical counterirritant effect by stimulating cutaneous sensory receptors); film formers (to hold active ingredients on the skin by producing a continuous film on skin upon drying); fragrances (consumer appeal); silicones/organomodified silicones (protection, water resistance, lubricity, softness); oils (mineral, vegetable, and animal); natural moisturizing agents (NMF) and other skin moisturizing ingredients known in the art; opacifiers (reduce the clarity or transparent appearance of the product); powders (enhance lubricity, oil adsorption, provide skin protection, astringency, opacity, etc.); skin conditioning agents; solvents (liquids employed to dissolve components found useful in the cosmetics or drugs); and surfactants (as cleansing agents, emulsifying agents, solubilizing agents, and suspending agents).

Ranges are used to describe the relative quantities of compounds in the compositions of the invention and ranges are used to describe the relative physical properties of the compositions of the invention. It is understood that the ranges are by way of illustration only and that one of skill in the art would recognize that the nature of the specific compositions dictates the levels to be applied to achieve the desired results. The levels of components are ascertainable by routine experimentation in view of the present disclosure.

The compositions of the invention typically have a melting point of from about 32° C. to about 100° C. Melting behavior in this range provides compositions that are relatively immobile and localized on the bodyfacing surface of the bodyside liner of the absorbent article at room temperature. Though relatively immobile and localized at room temperature, the compositions are also readily transferable to the wearer of the article at body temperature through natural rubbing or friction during wearing and through adhesion of the composition to the skin of the wearer. The compositions also maintain their integrity and are not completely liquid at elevated temperatures such as may be experienced during storage. Stability in a solid state at elevated temperatures is made possible, in part, by the increase in viscosity provided by the viscosity enhancers. Desirably, the compositions of the invention are easily transferable to the skin by way of normal contact, including adhesion of the composition to the skin, wearer motion or body heat. Because the compositions are relatively immobilized on the bodyfacing surfaces of the articles, the quantities of the compositions necessary to provide the desired skin barrier benefits are reduced. In addition, special barrier or wrapping materials may not be necessary for the articles of the invention.

The compositions of the invention have high shear viscosities of less than about 5,000 centipoise at processing temperatures such as at a temperature of about 60° C. or higher. The melting points and, therefore, the processing temperatures vary for different compositions of the invention. At about 55° C. or less, the compositions have low shear viscosities greater than about 50,000 centipoise. The compositions may also have a penetration hardness of from about 5 millimeters to about 365 millimeters at 25° C.

In addition to the articles and compositions already described, the present invention is also directed to absorbent articles that include an outer cover, a liquid permeable bodyside liner, an absorbent body and a composition on at least a portion of the bodyside liner. The bodyside liner defines a bodyfacing surface and the bodyside liner is connected in superposed relation to the outer cover. The absorbent body is located between the bodyside liner and the outer cover. The composition is on at least a portion of the bodyfacing surface of the bodyside liner.

The composition can include from about 0.1 to about 95 percent by weight of natural fats or oils that contain essential and non-essential fatty acids. The natural fats and oils may be selected from avocado oil, borage oil, lanolin, sunflower oil, soybean oil, corn oil, cottonseed oil and mixtures of such fats and oils. The composition can also include from about 0.1 to about 10 percent by weight of sterols and sterol derivatives. The sterols and sterol derivatives may be selected from cholesterol, sitosterol, stigmasterol, tall oil sterol, soy sterol and mixtures of such sterols. Additionally, the composition can include from about 1 to about 95 percent by weight of one or more emollients. The emollients may be selected from petrolatum, silicone oils, dimethicone, esters, hydrogenated animal/vegetable oils, triglycerides, glycerol esters, propylene glycol esters, alkoxylated alcohols, alkoxylated carboxylic acid, lanolin and mixtures of such emollients. The composition can also include from about 5 to about 95 percent by weight of one or more solidifying agents. The solidifying agents may be selected from beeswax, behenyl behenate, behenyl benzoate, branched esters, candelilla wax, carnauba wax, synthetic carnauba wax, PEG-12 carnauba wax, cerasin, microcrystalline wax, polyperfluoromethylisopropylether montan wax, hydrogenated microcrystalline wax, alkylmethylsiloxanes, glycol montanate, jojoba wax, lanolin wax, ozokerite, paraffin, synthetic paraffin, polyethylene, $C_{20}$–$C_{40}$ alkyl hydroxystearate, $C_{30}$ alkyl dimethicone, cetyl esters, zinc stearate and mixtures of such solidifying agents. The composition further includes from about 0.1 to about 40 percent by weight of one or more viscosity enhancers. The viscosity enhancers may be selected from ethylene/vinyl acetate copolymers, organically modified clays, polyethylene, silica and mixtures of such viscosity enhancers. The composition also includes from about 0.1 to about 10 percent by weight of one or more extracted botanical actives. The extracted botanical actives may be selected from extracts of Echinacea, Yucca, Willow Herb, Green Tea, Black Tea, Oolong Tea, Chinese Tea and mixtures of such botanicals. The composition may also include a rheology modifier for providing stability of insoluble and partially soluble components of the compositions.

The articles with respect to this aspect of the invention may have compositions on at least a portion of the bodyfacing surface of the bodyside liner in which the compositions may have certain physical properties. For example, the compositions may have melting points of from about 32° C. to about 100° C. such that the compositions are relatively immobile on the bodyfacing surface at room temperature but are readily transferable to the skin at body temperature. The compositions may also have viscosities less than about 5,000 centipoise at temperatures of about 60° C. and higher and viscosities greater than about 50,000 centipoise at temperatures of about 55° C. and lower. Additionally, the compositions may have a penetration hardness of from about 5 millimeters to about 365 millimeters at 25° C. The compositions may be applied to at least a portion of the bodyfacing surface in an amount of from about 0.1 grams per meter squared (g/m$^2$) to about 30 g/m$^2$. Those of skill in the art will know how to modify the components and attributes of the compositions encompassed by the invention to achieve the desired benefits to the skin barrier and reduction in inflammatory response of the skin based on the disclosure provided herein.

The present invention is further directed to a method of applying a composition to a bodyfacing surface of a bodyside liner of an absorbent article. The method of the invention includes a step of heating a composition to a temperature above the melting point of the composition. The composition can have a melting point of from about 32° C. to about 100° C. The composition can include an emollient, a viscosity enhancer and an extracted botanical active. The composition can also include fats and oils, sterols or sterol derivatives, solidifying agents, rheology modifiers or clays. The method further includes a step of applying the composition to the bodyfacing surface of a bodyside liner of an absorbent article. The bodyfacing surface is that surface of the absorbent article that comes into contact with the skin of the wearer of the absorbent article. Other components of the absorbent article besides the bodyside liner may come into contact with the skin of the wearer. The composition can also be applied to those components including the waist elastics, the leg elastics, containment flaps and any other components coming into contact with the skin.

The composition can be applied to the bodyfacing surface using a variety of techniques including foam application, spraying, slot coating, printing or combinations of these application techniques. The method of the invention also includes a step of resolidifying the composition. The composition can be resolidified in a variety of ways including chilling, slow cooling, curing or a combination of these techniques. Further, the composition can have a penetration hardness of from about 5 to about 365 millimeters at 25° C. after the step of resolidification.

In an additional aspect, the present invention is directed to a method for protecting the skin barrier on a skin surface of a user. The method can include a step of contacting the skin surface of a user with a bodyfacing surface of a liner material. The liner material may be any type of woven or non-woven material. More specifically, the liner material is of a material that is typically used for the bodyside liner of an absorbent article. The bodyfacing surface of the liner material has a composition on it. The composition can include an emollient, a viscosity enhancer and an extracted botanical active. More specifically, the composition can include from about 50 to about 95 percent by weight of emollients, from about 1 to about 40 percent by weight of viscosity enhancers and from about 0.1 to about 10 percent by weight of extracted botanical actives.

The method can also include a step of maintaining the bodyfacing surface of the liner material in contact with the skin surface of a user for a sufficient amount of time to transfer the composition to the skin surface. For purposes of the method, a sufficient amount of time would be the amount of time necessary for enough of the composition to have been transferred so as to have a protective effect on the skin barrier. The method of the invention further includes a step of repeating contact of the skin surface with the bodyfacing surface of the liner material for a sufficient amount of time in order to have an improvement in the skin barrier function of the wearer's skin. The repeated contact can occur by either applying additional composition to the bodyfacing surface of the liner material or by applying a new liner material having a full amount of the composition on the bodyfacing surface.

The absorbent articles, methods and compositions of the invention advantageously protect the skin barrier and subdue inflammation in such a way not observed with conventional absorbent articles and compositions. Consequently, use of the absorbent articles and compositions of the invention protect the skin barrier against damage caused by physical and biological irritations. It is to be understood that both the foregoing general description and the following detailed description are exemplary and are intended to provide further explanation of the invention claimed. The accompanying drawings, that are incorporated in and constitute part of this specification, are included to illustrate and provide a further understanding of the articles, methods and compositions of the invention. Together with the description, the drawings serve to explain the various aspects of the invention.

BRIEF DESCRIPTION OF THE DRAWINGS

The present invention will be more fully understood and further advantages will become apparent when reference is made to the following detailed description of the invention and the accompanying drawings. The drawings are merely representative and are not intended to limit the scope of the claims. Like parts of the absorbent articles depicted in the drawings are referred to by the same reference numerals.

DETAILED DESCRIPTION OF THE INVENTION

The present invention is directed to solving problems related to protecting the skin barrier and subduing inflammatory response when the skin is exposed to causes of physical and biological damage. Similarly, the present invention is directed to solving problems related to the prevention and treatment of diaper rash.

The present disclosure of the invention will be expressed in terms of its various components, elements, constructions, configurations, arrangements and other features that may also be individually or collectively referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components or groups thereof.

The present invention encompasses compositions, compositions as they are applied to the bodyfacing materials of absorbent articles, absorbent articles including compositions and methods of applying compositions to absorbent articles. The following detailed description will be made in the context of one type of absorbent article, a disposable diaper that is adapted to be worn by infants about their lower torso. It is readily apparent, however, that the absorbent article of the present invention would also be suitable for use as another type of absorbent article, such as a feminine care pad, an incontinence garment, a training pant, a prefastened or refastenable diaper pant, a wound dressing or a nursing pad. Further, the compositions of the invention are not limited to application on the bodyfacing materials of absorbent articles. For example, the compositions of the inventions could be used on skin-contacting substrates such as tissues, wet (pre-moistened) wipe materials and cosmetic pads (such as for cleansing or buffing).

Figure 1:
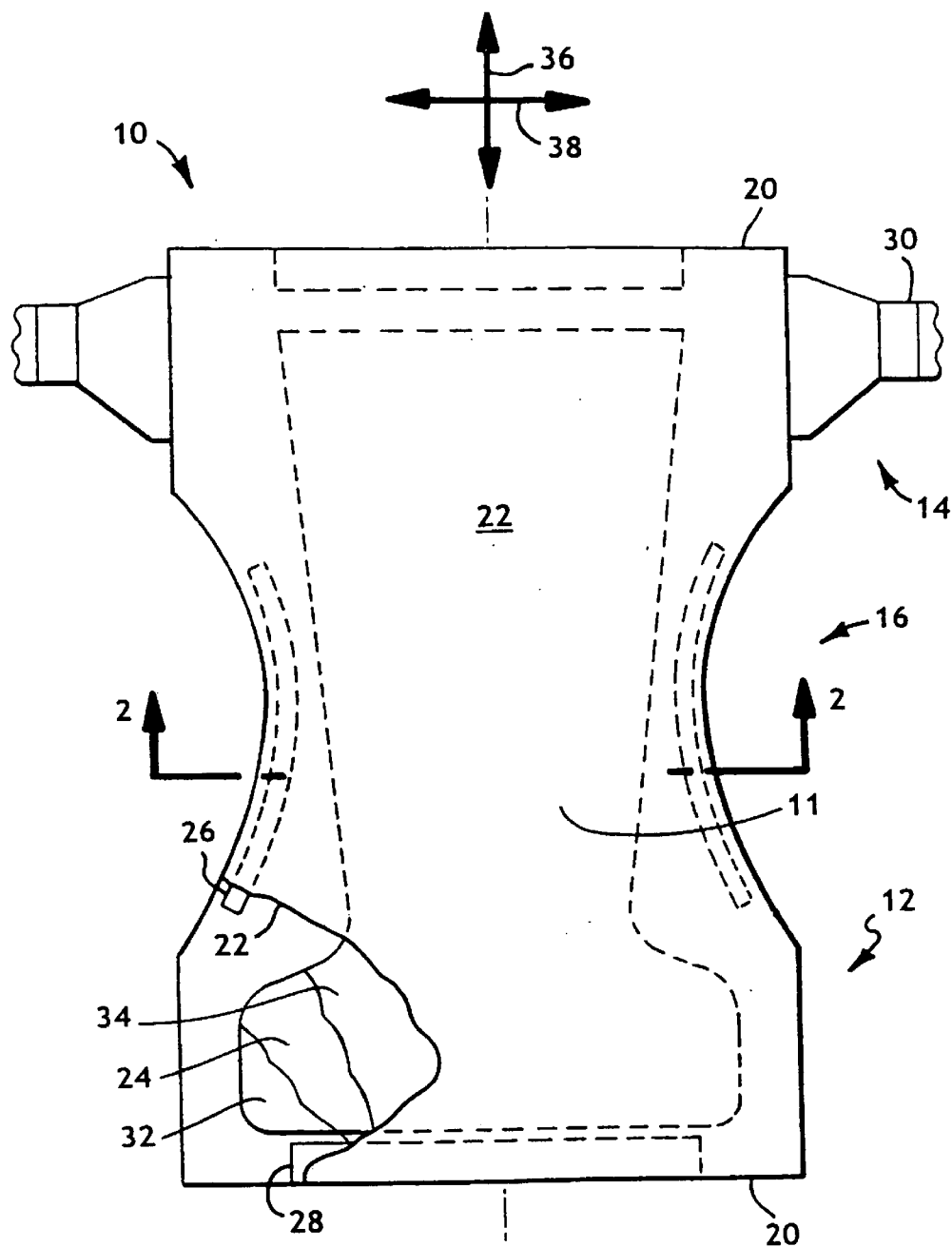
FIG. 1 representatively shows a partially cut away, top plan view of an absorbent article according to one aspect of the invention in a stretched and laid flat condition with the surface of the article that contacts the skin of the wearer facing the viewer.

FIG. 1 is a representative plan view of a disposable diaper 10 of the present invention in a flat-out, uncontracted state (i.e., with all elastic induced gathering and contraction removed). The bodyfacing surface 11 of the diaper 10, that is, the surface 11 of the diaper 10 that contacts the wearer is facing the viewer. The compositions of the invention can be applied to one or more bodyfacing materials that are components of the diaper 10. As used herein, the term 'bodyfacing material' includes, but is not limited to, materials such as the bodyside liner or topsheet, elastic material, tissue, intake and distribution material, absorbent material, and backsheet material. Each of these materials and components of a diaper 10 are described more fully herein. The compositions of the invention are applied to one or more of the bodyfacing materials in order to have a beneficial effect on the skin barrier. The bodyfacing material of the present invention can be a single layer or multi-layered.

With reference to FIG. 1, the diaper 10 generally defines a front waist section 12, a rear waist section 14, and an intermediate section 16 that interconnects the front and rear waist sections 12 and 14. The front and rear waist sections 12 and 14 include the general portions of the diaper 10 that are constructed to extend substantially over the wearer's front and rear abdominal regions, respectively, during use. The intermediate section 16 of the diaper 10 includes the general portion of the diaper 10 that is constructed to extend through the wearer's crotch region between the legs.

The diaper 10 includes a vapor permeable backsheet or outer cover 20, a liquid permeable topsheet or bodyside liner 22 positioned in facing relation with the outer cover 20, and an absorbent body 24, such as an absorbent pad, which is located between the outer cover 20 and the bodyside liner 22. The outer cover 20 defines a length and a width that, in the illustrated aspect, coincide with the length and width of the diaper 10. The absorbent body 24 generally defines a length and width that are less than the length and width of the outer cover 20, respectively. Thus, marginal portions of the diaper 10, such as marginal sections of the outer cover 20, may extend past the terminal edges of the absorbent body 24. In the illustrated aspects, for example, the outer cover 20 extends outwardly beyond the terminal marginal edges of the absorbent body 24 to form side margins and end margins of the diaper 10. The bodyside liner 22 is generally coextensive with the outer cover 20 but may optionally cover an area that is larger or smaller than the area of the outer cover 20, as desired. In other words, the bodyside liner 22 is connected in superposed relation to the outer cover 20. The outer cover 20 and bodyside liner 22 are intended to face the garment and body of the wearer, respectively, while in use.

To provide improved fit and to help reduce leakage of body exudates from the diaper 10, the diaper side margins and end margins may be elasticized with suitable elastic members, such as single or multiple strands of elastic. The elastic strands may be composed of natural or synthetic rubber and may optionally be heat shrinkable or heat elasticizable. For example, as representatively illustrated in FIG. 1, the diaper 10 may include leg elastics 26 which are constructed to operably gather and shirr the side margins of the diaper 10 to provide elasticized leg bands which can closely fit around the legs of the wearer to reduce leakage and provide improved comfort and appearance. Similarly, waist elastics 28 can be employed to elasticize the end margins of the diaper 10 to provide elasticized waists. The waist elastics 28 are configured to operably gather and shirr the waist sections to provide a resilient, comfortably close fit around the waist of the wearer. In the illustrated aspects, the elastic members are illustrated in their uncontracted, stretched condition for the purpose of clarity.

Fastening means, such as hook and loop fasteners 30, are employed to secure the diaper 10 on a wearer. Alternatively, other fastening means, such as buttons, pins, snaps, adhesive tape fasteners, cohesives, mushroom-and-loop fasteners, or the like, may be employed. Additionally, more than two fasteners can be provided, particularly if the diaper 10 is to be provided in a prefastened configuration. The fasteners can vary in size and form.

The diaper 10 may further include other layers between the absorbent body 24 and the bodyside liner 22 or outer cover 20. For example, as representatively illustrated in FIGS. 1 and 2, the diaper 10 may include a ventilation layer 32 located between the absorbent body 24 and the outer cover 20 to insulate the outer cover 20 from the absorbent body 24, to improve air circulation and to effectively reduce the dampness of the garment facing surface of the outer cover 20. The ventilation layer 32 may also assist in distributing fluid exudates to portions of the absorbent body 24 that do not directly receive the insult. The diaper 10 may also include a surge management layer 34 located between the bodyside liner 22 and the absorbent body 24 to prevent pooling of the fluid exudates and further improve air exchange and distribution of the fluid exudates within the diaper 10.

The diaper 10 may be of various suitable shapes. For example, the diaper may have an overall rectangular shape, T-shape or an approximately hourglass shape. In the shown aspect, the diaper 10 has a generally I-shape. The diaper 10 further defines a longitudinal direction 36 and a lateral direction 38. Other suitable diaper components that may be incorporated on absorbent articles of the present invention include containment flaps, waist flaps, elastomeric side panels, and the like which are generally known to those skilled in the art. Likewise, if the diaper 10 is to be sold in a prefastened condition, the diaper 10 may have passive bonds (not shown) that join the rear waist section 14 with the front waist section 12.

Examples of diaper configurations suitable for use in connection with the instant application that may include other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996 to Hanson et al., the disclosures of which are herein incorporated by reference.

The various components of the diaper 10 are integrally assembled together employing various types of suitable attachment means, such as adhesive, sonic bonds, thermal bonds or combinations thereof. In the shown aspect, for example, the bodyside liner 22 and outer cover 20 are assembled to each other and to the absorbent body 24 with lines of adhesive, such as a hot melt, pressure-sensitive adhesive. Similarly, other diaper components, such as the elastic members 26 and 28, fastening members 30, and ventilation and surge layers 32 and 34 may be assembled into the diaper 10 by employing the above-identified attachment mechanisms.

The outer cover 20 of the diaper 10, as representatively illustrated in FIG. 1, is composed of a substantially vapor permeable material. The permeability of the outer cover 20 is configured to enhance the breathability of the diaper 10 and to reduce the hydration of the wearer's skin during use without allowing excessive condensation of vapor, such as urine, on the garment facing surface of the outer cover 20 that can undesirably dampen the wearer's clothes. The outer cover 20 is generally constructed to be permeable to at least water vapor and has a water vapor transmission rate of at least about 1000 g/m$^2$/24 hr., desirably at least about 1500 g/m$^2$/24 hr, more desirably at least about 2000 g/m$^2$/24 hr., and even more desirably at least about 3000 g/m$^2$/24 hr. For example, the outer cover 20 may define a water vapor transmission rate of from about 1000 to about 6000 g/m$^2$/24 hr. Materials that have a water vapor transmission rate less than those above do not allow a sufficient amount of air exchange and undesirably result in increased levels of skin hydration.

The outer cover 20 is also desirably substantially liquid impermeable. For example, the outer cover 20 may be constructed to provide a hydrohead value of at least about 60 cm, desirably at least about 80 cm, and more desirably at least about 100 cm when subjected to the Hydrostatic Pressure Test. Materials that have hydrohead values less than those above undesirably result in the strike through of liquids, such as urine, during use. Such fluid strike through can undesirably result in a damp, clammy feeling on the outer cover 20 during use.

The outer cover 20 may be composed of any suitable materials that either directly provide the above desired levels of liquid impermeability and air permeability or, in the alternative, materials that can be modified or treated in some manner to provide such levels. In one aspect, the outer cover 20 may be a nonwoven fibrous web constructed to provide the required level of liquid impermeability. For example, a nonwoven web composed of spunbond or meltblown polymer fibers may be selectively treated with a water repellent coating or laminated with a liquid impermeable, vapor permeable polymer film to provide the outer cover 20. In a particular aspect of the invention, the outer cover 20 may include a nonwoven web composed of a plurality of randomly deposited hydrophobic thermoplastic meltblown fibers that are sufficiently bonded or otherwise connected to one another to provide a substantially vapor permeable and substantially liquid impermeable web. The outer cover 20 may also include a vapor permeable nonwoven layer that has been partially coated or otherwise configured to provide liquid impermeability in selected areas.

Examples of suitable materials for the outer cover 20 are also described in U.S. Pat. No. 5,482,765 issued Jan. 9, 1996 in the name of Bradley et al. and entitled "NONWOVEN FABRIC LAMINATE WITH ENHANCED BARRIER PROPERTIES"; U.S. Pat. No. 5,879,341 issued Mar. 9, 1999 in the name of Odorzynski et al. and entitled "ABSORBENT ARTICLE HAVING A BREATHABILITY GRADIENT"; U.S. Pat. No. 5,843,056 issued Dec. 1, 1998, in the name of Good et al. and entitled "ABSORBENT ARTICLE HAVING A COMPOSITE BREATHABLE BACKSHEET"; and U.S. patent application Ser. No. 08/882,712 filed Jun. 25, 1997, in the name of McCormack et al. and entitled "LOW GAUGE FILMS AND FILM/NONWOVEN LAMINATES", the disclosures of which are herein incorporated by reference.

In a particular aspect, the outer cover 20 is provided by a microporous film/nonwoven laminate material that includes a spunbond nonwoven material laminated to a microporous film. The spunbond nonwoven comprises filaments of about 1.8 denier extruded from a copolymer of ethylene with about 3.5 weight percent propylene and defines a basis weight of from about 17 to about 25 grams per square meter. The film comprises a cast coextruded film having calcium carbonate particles therein and defines a basis weight of about 58 grams per square meter prior to stretching. The film is preheated, stretched and annealed to form the micropores and then laminated to the spunbond nonwoven. The resulting microporous film/nonwoven laminate based material has a basis weight of from about 30 to about 60 grams per square meter and a water vapor transmission rate of from about 3000 to about 6000 g/m$^2$/24 hr. Examples of such film/ nonwoven laminate materials are described in more detail in U.S. patent application Ser. No. 08/882,712 filed Jun. 25, 1997, in the name of McCormack et al. and entitled "LOW GAUGE FILMS AND FILM/NONWOVEN LAMINATES", the disclosure of which has been incorporated by reference.

In another aspect, the outer cover 20 is provided by an extensible material. Further, the outer cover 20 can also be provided by a material having stretch in both the longitudinal 36 and lateral 38 directions. Extensible and stretchable outer cover materials can be used in absorbent articles to provide various benefits including better fitting articles.

Figure 2:
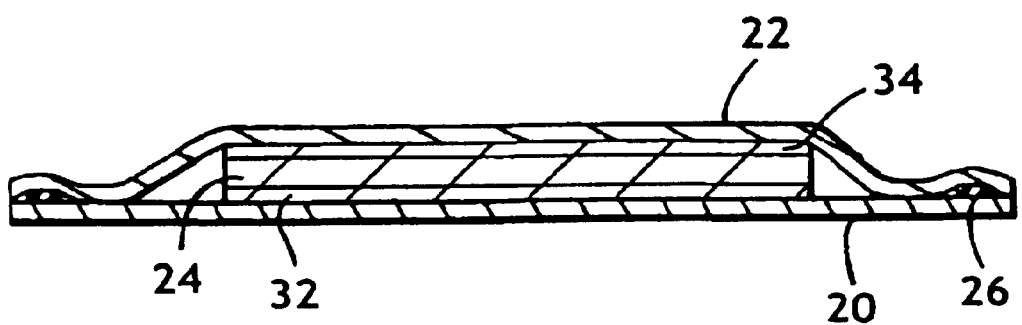
FIG. 2 representatively shows a sectional view of the absorbent article of FIG. 1 taken along line 2—2.

The bodyside liner 22, as representatively illustrated in FIGS. 1 and 2, defines a bodyfacing surface 11 that is compliant, soft feeling, and nonirritating to the wearer's skin. Further, the bodyside liner 22 may be less hydrophilic than the absorbent body 24, to present a relatively dry surface to the wearer, and may be sufficiently porous to be liquid permeable, permitting liquid to readily penetrate through its thickness. A suitable bodyside liner 22 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 22 is suitably employed to help isolate the wearer's skin from liquids held in the absorbent body 24.

Various woven and nonwoven fabrics can be used for the bodyside liner 22. For example, the bodyside liner 22 may be composed of a meltblown or spunbond web of polyolefin fibers. The bodyside liner 22 may also be a bonded-carded web composed of natural and/or synthetic fibers. The bodyside liner 22 may be composed of a substantially hydrophobic material, and the hydrophobic material may, optionally, be treated with a surfactant or otherwise processed to impart a desired level of wettability and hydrophilicity. In a particular aspect of the present invention, the bodyside liner 22 comprises a nonwoven, spunbond, polypropylene fabric composed of about 2.8–3.2 denier fibers formed into a web having a basis weight of about 22 grams per square meter and a density of about 0.06 gram per cubic centimeter.

In a particular aspect of the present invention, the bodyside liner 22 may be surface treated with about 0.3 weight percent of a surfactant mixture that contains a mixture of AHCOVEL Base N-62 and GLUCOPON 220UP surfactants in about a 3:1 ratio based on a total weight of the surfactant mixture. The AHCOVEL Base N-62 surfactant is purchased from Hodgson Textile Chemicals Inc., a business having offices in Mount Holly, N.C., and includes a blend of hydrogenated ethoxylated castor oil and sorbitan monooleate in a 55:45 weight ratio. The GLUCOPON 220UP surfactant is purchased from Henkel Corporation and includes alkyl polyglycoside. The surfactant may also include additional ingredients such as aloe. The surfactant may be applied by any conventional means, such as spraying, printing, brush coating, foam or the like. The surfactant may be applied to the entire bodyside liner 22 or may be selectively applied to particular sections of the bodyside liner 22, such as the medial section along the longitudinal centerline of the diaper, to provide greater wettability of such sections.

The absorbent body 24 of the diaper 10, as representatively illustrated in FIG. 1, may suitably comprise a matrix of hydrophilic fibers, such as a web of cellulosic fluff, mixed with particles of a high-absorbency material commonly known as superabsorbent material. In a particular aspect, the absorbent body 24 includes a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. Alternatively, the absorbent body 24 may include a laminate of fibrous webs and superabsorbent material or other suitable matrix for maintaining a superabsorbent material in a localized area.

The absorbent body 24 may have any of a number of shapes. For example, the absorbent body 24 may be rectangular, I-shaped, or T-shaped. It is generally preferred that the absorbent body 24 is narrower in the intermediate section than in the front or rear waist sections of the diaper 10. The absorbent body 24 may be provided by a single layer or, in the alternative, may be provided by multiple layers, all of which need not extend the entire length and width of the absorbent body 24. In a particular aspect of the invention, the absorbent body 24 can be generally T-shaped with the laterally extending cross-bar of the "T" generally corresponding to the front waist section 12 of the absorbent article for improved performance, especially for male infants. In the illustrated aspects, for example, the absorbent body 24 across the front waist section 12 of the article has a cross-directional width of about 18 centimeters, the narrowest portion of the intermediate section 16 has a width of about 7.5 centimeters and in the rear waist section 14 has a width of about 11.4 centimeters.

The size and the absorbent capacity of absorbent body 24 should be compatible with the size of the intended wearer and the liquid loading imparted by the intended use of the absorbent article. Further, the size and the absorbent capacity of the absorbent body 24 can be varied to accommodate wearers ranging from infants through adults. In addition, it has been found that with the present invention, the densities and/or basis weights of the absorbent body 24 can be varied. In a particular aspect of the invention, the absorbent body 24 has an absorbent capacity of at least about 300 grams of synthetic urine.

In aspects wherein the absorbent body 24 includes the combination of hydrophilic fibers and high-absorbency particles, the hydrophilic fibers and high-absorbency particles can form an average basis weight for the absorbent body 24 that is within the range of about 400–900 grams per square meter. In certain aspects of the invention, the average composite basis weight of such an absorbent body 24 is within the range of about 500–800 grams per square meter, and preferably is within the range of about 550–750 grams per square meter to provide the desired performance.

To provide the desired thinness dimension to the various configurations of the absorbent article of the invention, the absorbent body 24 can be configured with a bulk thickness that is not more than about 0.6 centimeters. Preferably, the bulk thickness is not more than about 0.53 centimeters, and more preferably is not more than about 0.5 centimeters to provide improved benefits. The bulk thickness is determined under a restraining pressure of 0.2 psi (1.38 kPa).

The high-absorbency material can be selected from natural, synthetic, and modified natural polymers and materials. The high-absorbency materials can be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers thereof. Further polymers suitable for use in the absorbent body 24 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers can also be useful in the present invention.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. In general, the high absorbency material is present in the absorbent body 24 in an amount of from about 5 to about 90 percent by weight, desirably in an amount of at least about 30 percent by weight, and even more desirably in an amount of at least about 50 percent by weight based on a total weight of the absorbent body 24. For example, in a particular aspect, the absorbent body 24 may include a laminate which includes at least about 50 percent by weight and desirably at least about 70 percent by weight of high-absorbency material overwrapped by a fibrous web or other suitable material for maintaining the high-absorbency material in a localized area.

An example of high-absorbency material suitable for use in the present invention is SANWET IM 3900 polymer available from Hoechst Celanese, a business having offices in Portsmouth, Va. Other suitable superabsorbents may include FAVOR SXM 880 polymer obtained from Stockhausen, a business having offices in Greensboro, N.C.

Optionally, a substantially hydrophilic tissue wrapsheet (not illustrated) may be employed to help maintain the integrity of the structure of the absorbent body 24. The tissue wrapsheet is typically placed about the absorbent body 24 over at least the two major facing surfaces thereof. The tissue wrapsheet can be composed of an absorbent cellulosic material, such as creped wadding or a high wet-strength tissue. In one aspect of the invention, the tissue wrapsheet can be configured to provide a wicking layer that helps to rapidly distribute liquid over the mass of absorbent fibers constituting the absorbent body 24.

The absorbent body 24 of the different aspects of the present invention further includes a plurality of zones of high air permeability which allow air and vapors to readily pass through the absorbent body 24 and through the vapor permeable outer cover 20 out of the diaper 10 into ambient air. For example, the absorbent body 24 may include a plurality of air passageways that provide the absorbent body 24 with zones or regions of high air permeability. The portions of the absorbent body 24 adjacent the air passageways provide zones or regions of high absorption. The zones of high air permeability are designed to provide the maximum air exchange from the absorbent body 24 while the zones of high absorption are designed to receive and hold the majority of the body exudates. The absorbent body 24 may define any number of zones of high air permeability that provide the improved air exchange. Desirably, the absorbent body 24 defines at least 3 and more desirably at least 5 different zones of high air permeability for improved performance.

The zones of high air permeability, such as the air passageways, are configured to enhance the breathability of the article to reduce the hydration of the wearer's skin during use without allowing excessive condensation of vapor, such as urine, on the garment facing surface of the outer cover 20. Such condensation of vapor on the outer surface of the diaper 10 can undesirably dampen the wearer's clothes. The zones of high air permeability are generally located in the area of the diaper over which air and vapor can transfer from the bodyside liner 22, through the absorbent body 24 and any other intervening layer or layers of material, and out the vapor permeable outer cover 20. For example, the zones of high air permeability may be located throughout the entire absorbent body 24 or may be selectively located in those regions of the absorbent body 24 that provide the maximum air exchange, such as the intermediate section 16 of the diaper 20. In a particular aspect, the zones of high air permeability are located in the front and intermediate sections 12 and 16, respectively, of the diaper 10 for improved air exchange.

The zones of high absorption, on the other hand, are not designed to transfer a high level of air and vapor from the interior of the diaper 10. Thus, the air exchange from the bodyside liner 22 of the diaper 10 to the outer cover 20 of the diaper and into the ambient atmosphere (exterior of the diaper 10) occurs generally through the absorbent body 24 in the zones of high air permeability. Some air exchange through the absorbent body 24 can also occur in the zones of high absorption to a limited degree. The zones of high air permeability may have any desired configuration including rectangular, circular, hourglass, oval, and the like, and may also include selected longitudinal or lateral strips or multiple regions which may be intermittently located.

The zones of high air permeability may have any desired dimensions that effectively provide improved air exchange while preventing excessive condensation of vapor from the absorbent body 24 through and onto the garment facing surface of the outer cover 20. Desirably, the zones of high air permeability may define a total area of from about 5 to about 75 percent, more desirably at least about 10 percent, even more desirably from about 10 to about 70 percent, and still more desirably from about 10 to about 60 percent of the total surface area of the absorbent body 24 of the diaper 10. For example, in a diaper 10 intended for use on a medium sized infant, the zones of high air permeability may define a total area of from about 6 to about 90 square centimeters.

When the total area of the zones of high air permeability is greater than the above amounts, the diaper 10 may exhibit an undesirable amount of condensation of vapor on the exposed, garment facing surface of the outer cover 20 undesirably resulting in a clammy feeling on the outer surface of the diaper 10. Whereas, when the total area of the zones of high air permeability is less than the above amounts, the diaper 10 may exhibit a low level of air exchange resulting in high levels of skin hydration that can undesirably lead to skin irritation and rash.

The zones of high air permeability of the absorbent body 24 of the diaper 10 are constructed to be substantially permeable to at least air and preferably permeable to water vapor. For example, the zones of high air permeability of the absorbent body 24 define a Frazier Porosity value which is at least about 10 percent, more desirably at least about 20 percent and even more desirably at least about 50 percent greater than the Frazier Porosity value of the zones of high absorption of the absorbent body 24. As used herein, the term "Frazier Porosity" refers to the value determined according to the Frazier Porosity Test set forth below. When the zones of high air permeability exhibit Frazier Porosity values less than those indicated above, the diaper 10 may exhibit a low level of air exchange resulting in high levels of skin hydration that can undesirably lead to skin irritation and rash.

The zones of high air permeability may be provided in a variety of ways. The zones of high air permeability may be integral portions of the absorbent body 24 of the absorbent article or may be provided by apertures, holes or open spaces in the absorbent body 24. For example, portions of the absorbent body 24 may be discontinuous or removed to provide the zones. Alternatively, the zones of high air permeability may be provided by portions of the absorbent body 24 that are constructed to absorb less fluid exudates thereby resulting in improved air flow through such portions in use. For example, portions of the absorbent body 24 may be void of or contain substantially less high-absorbency material than other portions of the absorbent body 24 to provide such improved air flow. Portions of the absorbent body 24 may otherwise be treated or coated with a solution that renders them hydrophobic to provide the zones of high air permeability in selected areas. In other alternative configurations, the zones of high air permeability may be provided by creating voids or holes in the absorbent body 24 and placing other materials having a higher air permeability than the absorbent body 24, such as those materials described below as being suitable for the surge management layer 34, in the holes or voids.

Due to the thinness of absorbent body 24 and the high absorbency material within the absorbent body 24, the liquid uptake rates of the absorbent body 24, by itself, may be too low, or may not be adequately sustained over multiple insults of liquid into the absorbent body 24. To improve the overall liquid uptake and air exchange, the diaper 10 of the different aspects of the present invention may further include a porous, liquid-permeable layer of surge management material 34, as representatively illustrated in FIG. 1. The surge management layer 34 is typically less hydrophilic than the absorbent body 24, and has an operable level of density and basis weight to quickly collect and temporarily hold liquid surges, to transport the liquid from its initial entrance point and to substantially completely release the liquid to other parts of the absorbent body 24. This configuration can help prevent the liquid from pooling and collecting on the portion of the diaper 10 positioned against the wearer's skin, thereby reducing the feeling of wetness by the wearer. The structure of the surge management layer 34 also generally enhances the air exchange within the diaper 10.

Various woven and nonwoven fabrics can be used to construct the surge management layer 34. For example, the surge management layer 34 may be a layer composed of a meltblown or spunbond web of synthetic fibers, such as polyolefin fibers. The surge management layer 34 may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The surge management layer 34 may be composed of a substantially hydrophobic material, and the hydrophobic material may optionally be treated with a surfactant or otherwise processed to impart a desired level of wettability and hydrophilicity. In a particular aspect, the surge management layer 34 includes a hydrophobic, nonwoven material having a basis weight of from about 30 to about 120 grams per square meter.

For example, in a particular aspect, the surge management layer 34 may include a bonded-carded-web, nonwoven fabric that includes bicomponent fibers and that defines an overall basis weight of about 83 grams per square meter. The surge management layer 34 in such a configuration can be a homogeneous blend composed of about 60 weight percent polyethylene/polyester (PE/PET), sheath-core bicomponent fibers that have a fiber denier of about 3 d and about 40 weight percent single component polyester fibers that have a fiber denier of about 6 d and that have fiber lengths of from about 3.8 to about 5.08 centimeters.

In the illustrated aspects, the surge management layer 34 is arranged in a direct, contacting liquid communication with the absorbent body 24. The surge management layer 34 may be operably connected to the bodyside liner 22 with a conventional pattern of adhesive, such as a swirl adhesive pattern. In addition, the surge management layer 34 may be operably connected to the absorbent body 24 with a conventional pattern of adhesive. The amount of adhesive add-on should be sufficient to provide the desired levels of bonding, but should be low enough to avoid excessively restricting the movement of liquid from the bodyside liner 22, through the surge management layer 34 and into the absorbent body 24.

The absorbent body 24 is positioned in liquid communication with surge management layer 34 to receive liquids released from the surge management layer 34, and to hold and store the liquid. In the shown aspect, the surge management layer 34 includes a separate layer that is positioned over another, separate layer including the absorbent body 24, thereby forming a dual-layer arrangement. The surge management layer 34 serves to quickly collect and temporarily hold discharged liquids, to transport such liquids from the point of initial contact and spread the liquid to other parts of the surge management layer 34, and then to substantially completely release such liquids into the layer or layers constituting the absorbent body 24.

The surge management layer 34 can be of any desired shape. Suitable shapes include for example, circular, rectangular, triangular, trapezoidal, oblong, dog-boned, hourglass-shaped, or oval. In certain aspects, for example, the surge management layer 34 can be generally rectangular-shaped. In the illustrated aspects, the surge management layer 34 is coextensive with the absorbent body 24. Alternatively, the surge management layer 34 may extend over only a part of the absorbent body 24. Where the surge management layer 34 extends only partially along the length of the absorbent body 24, the surge management layer 34 may be selectively positioned anywhere along the absorbent body 24. For example, the surge management layer 34 may function more efficiently when it is offset toward the front waist section 12 of the diaper 10. The surge management layer 34 may also be approximately centered about the longitudinal center line of the absorbent body 24.

Additional materials suitable for the surge management layer 34 are set forth in U.S. Pat. No. 5,486,166 issued Jan. 23, 1996 in the name of C. Ellis et al. and entitled "FIBROUS NONWOVEN WEB SURGE LAYER FOR PERSONAL CARE ABSORBENT ARTICLES AND THE LIKE"; U.S. Pat. No. 5,490,846 issued Feb. 13, 1996 in the name of Ellis et al. and entitled "IMPROVED SURGE MANAGEMENT FIBROUS NONWOVEN WEB FOR PERSONAL CARE ABSORBENT ARTICLES AND THE LIKE"; and U.S. Pat. No. 5,364,382 issued Nov. 15, 1994 in the name of Latimer et al. and entitled "ABSORBENT STRUCTURE HAVING IMPROVED FLUID SURGE MANAGEMENT AND PRODUCT INCORPORATING SAME", the disclosures of which are hereby incorporated by reference.

As representatively illustrated in FIG. 1, the diaper 10 may also include a ventilation layer 32 located between the outer cover 20 and the absorbent body 24. The ventilation layer 32 serves to facilitate the movement of air within and through the diaper 10 and prevent the outer cover 20 from being in surface to surface contact with at least a portion of the absorbent body 24. Specifically, the ventilation layer 32 serves as a conduit through which air and water vapor can move from the absorbent body 24 through the vapor permeable outer cover 20.

The ventilation layer 32 may be formed from materials described above as being suitable for the surge management layer 34 such as nonwoven, (e.g., spunbond, meltblown or carded), woven, or knitted fibrous webs composed of natural fibers and/or synthetic polymeric fibers. Suitable fibers include, for example, acrylic fibers, polyolefin fibers, polyester fibers, or blends thereof. The ventilation layer 32 may also be formed from a porous foam material such as an open-celled polyolefin foam, a reticulated polyurethane foam, and the like. The ventilation layer 32 may include a single layer of material or a composite of two or more layers of material. In a particular aspect, the ventilation layer 32 includes a hydrophobic, nonwoven material having a thickness of at least about 0.10 centimeters determined under a restraining pressure of 0.05 psi (0.34 kPa) and a basis weight of from about 20 to about 120 grams per square meter. For example, the ventilation layer 32 may comprise a bonded-carded-web, nonwoven fabric that includes bicomponent fibers and that defines an overall basis weight of about 83 grams per square meter. The ventilation layer 32 in such a configuration can be a homogeneous blend composed of about 60 weight percent polyethylene/polyester (PE/PET), sheath-core bicomponent fibers that have a fiber denier of about 3 d and about 40 weight percent single component polyester fibers that have a fiber denier of about 6 d and that have fiber lengths of from about 3.8 to about 5.08 centimeters.

The ventilation layer 32 can be of any desired shape. Suitable shapes include for example, circular, rectangular, triangular, trapezoidal, oblong, dog-boned, hourglass-shaped, or oval. The ventilation layer 32 may extend beyond, completely over or partially over the absorbent body 24. For example, the ventilation layer 32 may suitably be located over the intermediate section 16 of the diaper 10 and be substantially centered side-to-side with respect to the longitudinal centerline 36 of the diaper 10. It is generally desired that the entire absorbent body 24 be overlaid with the ventilation layer 32 to prevent substantially all surface to surface contact between the outer cover 20 and the absorbent body 24. In the illustrated aspects, the ventilation layer 32 is coextensive with the absorbent body 24. This allows for the maximum degree of air exchange with minimal dampness on the garment facing surface of the outer cover 20.

In the illustrated aspects, the ventilation layer 32 is arranged in a direct, contacting liquid communication with the absorbent body 24. The ventilation layer 32 may be operably connected to the outer cover 20 with a conventional pattern of adhesive, such as a swirl adhesive pattern. In addition, the ventilation layer 32 may be operably connected to the absorbent body 24 with a conventional pattern of adhesive. The amount of adhesive add-on should be sufficient to provide the desired levels of bonding, but should be low enough to avoid excessively restricting the movement of air and vapor from the absorbent body 24 and through the outer cover 20.

The ventilation layer 32 may further serve to quickly collect and temporarily hold discharged liquids, which pass through the absorbent body 24 and, in particular, through the zones of high air permeability within the absorbent body 24. The ventilation layer 32 may then transport such liquids from the point of initial contact and spread the liquid to other parts of the ventilation layer 32, and then substantially completely release such liquids into the layer or layers of the absorbent body 24.

In order to protect the barrier of the skin covered by the diaper 10, a composition is applied to the bodyfacing surface 11 of the bodyside liner 22 of the diaper 10. The composition generally can include emollient(s), viscosity enhancer(s) and extracted botanical active(s). The composition can also include natural fats or oils, solidifying agents and sterols or sterol derivatives. Additionally, the composition can include a rheology modifier and a natural clay or a synthetic analog of a natural clay. For example, the compositions of the invention may include from about 50 to about 95 percent by weight of one or more emollients; from about 0.1 to about 40 percent by weight of one or more viscosity enhancers; and, from about 0.1 to about 10 percent by weight of one or more extracted botanical actives. The composition may include other ingredients as well. Ranges are used to describe the relative amounts of components in the compositions of the invention as well as to describe the relative physical properties of the compositions. These ranges are illustrative and one of skill in the art will recognize that the nature of the composition will dictate the various levels of components that must be used to achieve the intended benefit for the skin barrier. The levels can be determined by routine experimentation in view of the disclosure provided herein.

The compositions of the invention can be in a variety of physical forms including emulsions, lotions, creams, ointments, salves, suspensions, gels or hybrids of these forms.

The emollients of the compositions act as lubricants to reduce the abrasiveness of the bodyside liner 22 to the skin and, upon transfer to the skin, help to maintain the soft, smooth and pliable appearance of the skin. In general, emollients are skin-conditioning ingredients that help to soften, smooth, plasticize, lubricate, moisturize, improve the appearance of, improve the feel of and protect skin. Suitable emollients that can be incorporated into the compositions include oils such as petroleum based oils, petrolatum, vegetable based oils, hydrogenated vegetable oils, animal oils, hydrogenated animal oils, mineral oils, natural or synthetic oils, alkyl dimethicones, alkyl methicones, alkyldimethicone copolyols, phenyl silicones, siliconized waxes, alkyl trimethylsilanes, dimethicone, lanolin and its derivatives, esters, branched esters, glycerol esters and derivatives, propylene glycol esters and derivatives, alkoxylated carboxylic acids, alkoxylated alcohols, fatty alcohols, triglycerides, alkyl hydroxystearates and mixtures of such compounds. The esters can be selected from cetyl palmitate, stearyl palmitate, cetyl stearate, isopropyl laurate, isopropyl myristate, isopropyl palmitate, behenyl behenate, stearyl behenate, $C_{12}$–$C_{15}$ alkyl fumarate, $C_{20}$–$C_{40}$ alkyl behenate, dibehenyl fumarate, branched esters and mixtures thereof. Ethers such as eucalyptol, cetearyl glucoside, dimethyl isosorbicide polyglyceryl-3 cetyl ether, polyglyceryl-3 decyltetradecanol, propylene glycol myristyl ether and mixtures thereof can also be used as emollients. The fatty alcohols include octyldodecanol, lauryl, myristyl, cetyl, stearyl and behenyl alcohol, $C_{24}$ and greater fatty alcohols and mixtures thereof. For example, a particularly well suited emollient is petrolatum. Other conventional emollients may also be added in a manner that maintains the desired properties of the compositions set forth herein.

To provide improved stability and transfer to the skin of the wearer, the compositions may include from about 1 to about 95 percent by weight, desirably from about 20 to about 75 percent by weight, and more desirably from about 40 to about 60 percent by weight of the emollient. In particular aspects, the emollient can be at least a minimum of about 1 percent by weight. The emollient can alternatively be at least about 20 percent, and optionally, can be at least about 40 percent to provide improved performance. In other aspects, the emollient can be not more than a maximum of about 95 percent by weight. The emollient can alternatively be not more than about 75 percent, and optionally, can be not more than about 60 percent to provide improved effectiveness. Compositions that include an amount of emollient greater than the recited amounts tend to have lower viscosities that undesirably lead to migration of the composition. Whereas, compositions that include an amount of emollient less than the recited amounts tend to provide less transfer to the wearer's skin.

The solidifying agent(s) in the compositions of the present invention primarily functions to solidify the composition so that the composition is a solid at room temperature and has a penetration hardness of at least 5 mm and has a melting point of at least 32° C. The solidifying agent may also provide a tackiness to the composition that improves the transfer by adhesion to the skin of the wearer. Depending on the solidifying agent selected, the solidifying agent can also modify the mode of transfer so that the composition tends to fracture or flake off instead of actually rubbing off onto the skin of the wearer which can lead to improved transfer to the skin. The solidifying agent may further function as an emollient, occlusive agent, moisturizer, barrier enhancer, viscosity enhancer and combinations thereof. The solidifying agents may include waxes as well as compounds that perform functionally as waxes.

The solidifying agents can be selected from alkyl siloxanes, polymers, hydrogenated vegetable oils having a melting point of 35° C. or greater, fatty acid esters and branched esters with a melting point of 35° C. or greater, alkyl hydroxystearates (>C16), alkoxylated alcohols and alkoxylated carboxylic acid. Additionally, the solidifying agents can be selected from animal, vegetable and mineral waxes, synthetic waxes and alkyl silicones. Examples of solidifying agents include, but are not limited to, the following: alkyl silicones, alkyl trimethylsilanes, beeswax, behenyl behenate, behenyl benzoate, C24–C28 alkyl dimethicone, C30 alkyl dimethicone, cetyl methicone, stearyl methicone, cetyl dimethicone, stearyl dimethicone, cerotyl dimethicone, candelilla wax, carnauba, synthetic carnauba, PEG-12 carnauba, cerasin, hydrogenated microcrystalline wax, jojoba wax, microcrystalline wax, lanolin wax, ozokerite, paraffin, synthetic paraffin, cetyl esters, behenyl behenate, $C_{20}$–$C_{40}$ alkyl behenate, $C_{12}$–$C_{15}$ lactate, cetyl palmitate, stearyl palmitate, isosteryl behenate, lauryl behenate, stearyl benzoate, behenyl isostearate, cetyl myristate, cetyl octanoate, cetyl oleate, cetyl ricinoleate, cetyl stearate, decyl oleate, di-$C_{12}$–$C_{15}$ alkyl fumerate, dibehenyl fumerate, myristyl lactate, myristyl lignocerate, myristyl myristate, myristyl stearate, lauryl stearate, octyldodecyl stearate, octyldodecyl stearoyl stearate, oleyl arachidate, oleyl stearate, tridecyl behenate, tridecyl stearate, tridecyl stearoyl stearate, pentaerythrityl tetrabehenate, pentaerythritylhydrogenated rosinate, pentaerythrityl distearate, pentaerythrityl tetraabeite, pentaerythrityl tetracocoate, pentaerythrityl tetraperlargonate, pentaerythrityl tetrastearate, ethylene vinyl acetate, polyethylene, hydrogenated cottonseed oil, hydrogenated vegetable oil, hydrogenated squalene, hydrogenated coconut oil, hydrogenated jojoba oil, hydrogenated palm oil, hydrogenated palm kernel oil, hydrogenated olive oil, polyamides, metal stearates and other metal soaps, $C_{30}$–$C_{60}$ fatty alcohols, $C_{20+}$ fatty amides, polypropylene, polystyrene, polybutane, polybutylene terephthalate, polydipentane, polypropylene, zinc stearate, dodecyl laurate, stearyl palmitate, octadecyl hexadecanoate, octadecyl palmitate, stearyl behenate, docosyl octanoate, tetradecyl-octadecanyl behenate, hexadecyl-cosanyl hexacosanate, shellac wax, glycol montanate, fluoranated waxes, $C_{20}$–$C_{40}$ alkyl hydroxystearyl stearate and mixtures of such compounds. Suitable branched esters include tetradecyl-octadecanyl behenate and hexadecyl-cosanyl-hexacosanate. In one aspect, the solidifying agent is a blend including about 70 weight percent cerasin wax, about 10 weight percent microcrystalline wax, about 10 weight percent paraffin wax and about 10 weight percent cetyl esters (synthetic spermaceti wax.

Appropriate solidifying agents also include alkylmethylsiloxanes that can be described as non-volatile, occlusive silicone-aliphatic hydrocarbon hybrid waxes. An example of an alkylmethylsiloxane wax is a poly(n-alkylmethylsiloxane)dimethylsiloxane. The poly(n-alkylmethylsiloxane)dimethylsiloxane can have an n-alkyl substitution of an average of 16 carbon atoms or above with an average of more than 2 alkyl groups per molecule, with hydrocarbon contents of at least 40% and with an average molecular weight of at least 1800 or higher. Examples of desirable alkylmethylsiloxanes for use in the compositions of the invention include random copolymers having the following formula:

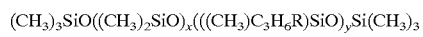

The "R" component of the formula can be an aliphatic hydrocarbon substituent where the chain length is from $C_4$ to $C_{45}$. In particular, "R" can be $C_{16}$, $C_{16-18}$, $C_{20-24}$ or $C_{30-45}$. For example, $C_{30-45}$ alkylmethylsiloxane is commercially available as trade designation "SF1642" from General Electric Silicones or "AMS-$C_{30}$" from Dow Corning Silicones. The value of "x" is on average more than 2 and the value of "y" is at least 1. The nature of the alkylmethylsiloxane must be balanced between its compatibility with dimethicone or polydimethyl siloxane and its compatibility with organic compounds like petrolatum and waxes. For example, as "x" increases, "y" decreases and "R" is small, the molecule increases its compatibility with dimethicone but decreases its compatibility with organic compounds. Alternatively, as "x" decreases, "y" increases and "R" is $C_{18+}$, the molecule decreases its compatibility with dimethicone but increases its compatibility with organic compounds. These solidifying agents can be used to stabilize dimethicone-containing compositions of the invention.

To provide improved transfer to the skin of the wearer, the composition may include from about 5 to about 95 percent by weight, desirably from about 25 to about 75 percent by weight, and more desirably from about 30 to about 50 percent by weight of solidifying agent(s).). In particular aspects, the solidifying agent can be at least a minimum of about 5 percent by weight. The solidifying agent can alternatively be at least about 25 percent, and optionally, can be at least about 30 percent to provide improved performance. In other aspects, the solidifying agent can be not more than a maximum of about 95 percent by weight. The solidifying agent can alternatively be not more than about 75 percent, and optionally, can be not more than about 50 percent to provide improved effectiveness. Compositions that include an amount of solidifying agent less than the recited amounts tend to be too soft and may have lower viscosities that may undesirably lead to migration of the composition away from bodyfacing surfaces 11 of the absorbent article, thus diminishing transfer to the wearer's skin. Whereas, compositions that include an amount of solidifying agent greater than the recited amounts tend to provide less transfer to the wearer's skin.

One or more viscosity enhancers may be added to the composition to increase the viscosity, to help stabilize the formulation on the bodyfacing surface 11 of the bodyside liner 22 and, thereby, to reduce migration and improve transfer to the skin. The viscosity enhancer increases the meltpoint viscosity of the compositions to have a high viscosity (greater than about 50,000 centipoise) under low shear at the "hot box car" stability temperature of about 54.5° C. and at lower temperatures. Having viscosity at elevated temperatures prevents the compositions from migrating into or away from the materials to which they are applied. However, the viscosity enhancer component also provides a low viscosity (less than about 5,000 centipoise) under shear for the compositions at process conditions. Typically, process temperatures are approximately 5° C. above the melting point of the composition. Generally, the process temperature is about 60° C. or higher. Different compositions of the invention will have different melting points. The viscosity enhancers of the invention are capable of maintaining the viscosity of compositions of the invention up to temperatures just below the desired processing temperature for a given composition. Examples of suitable viscosity enhancers include polyolefin resins, lipophilic/oil thickeners, ethylene/vinyl acetate copolymers, organically modified clays, polyethylene, silica, silica silylate, silica methyl silylate, colloidal silicone dioxide, cetyl hydroxy ethyl cellulose, other organically modified celluloses, PVP/decane copolymer, PVM/MA decadiene crosspolymer, PVP/eicosene copolymer, PVP/hexadecane copolymer, microcrystalline wax, hexadecyl-cosanyl-hexacosanate, shellac wax, glycol montanate, PEG-12 carnauba, synthetic paraffin, ozokerite, $C_{20}$–$C_{40}$ alkyl hydroxystearyl stearate, polyperfluoromethylisopropylether montan wax and mixtures of these compounds. A particularly well suited viscosity enhancer is an ethylene/vinyl acetate copolymer commercially available from E. I. Dupont De Ne Mours under the trade designation "ELVAX". Additionally, the compounds identified herein as suitable solidifying agents may also function as viscosity enhancers to benefit the rheology of the compositions of the invention.

To provide the improved transfer to the skin of the wearer, the composition may include from about 0.1 to about 40 percent by weight, desirably from about 3 to about 20 percent by weight, and more desirably from about 5 to about 10 percent by weight of the viscosity enhancer for reduced migration and improved transfer to the wearer's skin.). In particular aspects, the viscosity enhancer can be at least a minimum of about 0.1 percent by weight. The viscosity enhancer can alternatively be at least about 3 percent, and optionally, can be at least about 5 percent to provide improved performance. In other aspects, the viscosity enhancer can be not more than a maximum of about 40 percent by weight. The viscosity enhancer can alternatively be not more than about 20 percent, and optionally, can be not more than about 10 percent to provide improved effectiveness.

The extracted botanical actives of the compositions are extracts, containing the chemically "active" components, of various plants and plant substances. The extracted botanical actives, in combination with the other components of the composition, provide several benefits to the skin, particularly skin that is frequently covered by an absorbent article and that is exposed to biological insults. Extracted botanical actives can include any water-soluble or oil-soluble active extracted from a particular plant. Examples of suitable extracted botanical actives are actives extracted from echinacea, yucca glauca, willow herb, basil leaves, Turkish oregano, carrot root, grapefruit fruit, fennel fruit, rosemary, thyme, blueberry, bell pepper, black tea, blackberry, black currant fruit, Chinese tea, coffee seed, dandelion root, date palm fruit, gingko leaf, green tea polyphenols (i.e. including epicatechin gallate and epigallocatechin 3-O-gallate), hawthorn berries, licorice, oolong tea, sage, strawberry, sweet pea, tomato, vanilla fruit, neohesperidin, quercetin, rutin, morin, myricetin, chlorogenic acid, glutathione, glycyrrhizin, absinthe, arnica, centella asiatica, chamomelle, comfrey, cornflower, horse chestnut, ivy (Herdera helix), magnolia, mimosa, oat extract, pansey, scullcap, seabuckthorn, white nettle, witch hazel and any combinations thereof. Particular benefits have been observed with compositions including echinacea, yucca glauca, green tea, black tea, oolong tea, Chinese tea and willow herb. Echinacea actives may be obtained from the following echinacea species: *Echinacea angustifolia, Echinacea purpurea*, and *Echinacea pallida*. Varieties of black tea include Flowery Orange Pekoe, Golden Flowery Orange Pekoe and Fine Tippy Golden Flowery Orange Pekoe. Varieties of green tea include Japanese and Green Darjeeling.

The compositions of the invention can include from about 0.1 to about 10 percent by weight of one or more extracted botanical actives. More specifically, the compositions can include from about 0.5 to about 8 percent by weight of one or more extracted botanical actives. Even more specifically, the compositions include from about 1 to about 5 percent by weight of extracted botanical actives.). In particular aspects, the extracted botanical actives can be at least a minimum of about 0.1 percent by weight. The extracted botanical actives can alternatively be at least about 0.5 percent, and optionally, can be at least about 1 percent to provide improved performance. In other aspects, the extracted botanical actives can be not more than a maximum of about 10 percent by weight. The extracted botanical actives can alternatively be not more than about 8 percent, and optionally, can be not more than about 5 percent. Botanicals are primarily extracts of the plants from which they originate and botanicals are available from suppliers as part of a composition that also contains an extracting solvent. Amounts of the botanicals in the compositions of the invention in terms of active component (not extract) may range from about 0.000001 to about 10% by weight. Desirably, the amount of active botanical is from about 0.00001 to about 5% and more desirably from about 0.0001 to about 1% by weight of the composition. Further, it is also desirable that the amount of active botanical is from about 0.0001 to about 0.5% of the composition and more desirably from about 0.001 to about 0.1% by weight of the composition.

Sometimes it is necessary for the compositions of the invention to include additional components that can be used to emulsify or suspend the extracted botanical active with the rest of the composition. If the extracted botanical active is not properly incorporated into the composition, it may not have the bioavailability to provide benefits to the skin. In addition to modifications to the formulation, extracted botanical actives can also be better incorporated through the use of processing techniques. For compositions of the invention including Echinacea, it may be necessary to add an emulsifying agent such as an emulsifier having an HLB less than 7. An appropriate emulsifying agent is ABIL EM90 emulsifier available from Goldschmidt AG of Germany. Other appropriate emulsifiers include sorbitan monooleate, sorbitan sesquioleate, sorbitan trioleate and glycerol monooleate. The Echinacea can also be better incorporated into the composition by using high shear in processing or a suitable viscosity enhancer. Another option for dispersing a botanical such as Echinacea is to first blend the botanical with a hydrophilic solvent such as water, propylene glycol, butylene glycol or glycerol. Dispersing the botanical in a hydrophilic solvent and using an emulsifying agent to incorporate the solvent (which can also be referred to as a penetrant enhancer) into the remainder of the composition provides the botanical in a "bioavailable" form in which it can contribute to protecting the skin barrier and subduing the inflammatory response of the skin.

For the reasons described above, emulsifiers, particularly those of HLB below 7, may be useful for purposes of the present invention at levels to from about 0.1 to about 10% by weight. Suitable emulsifiers include alkoxylated $C_8$–$C_{30}$ fatty acids and fatty alcohols. Examples of such emulsifiers are polyoxyethylene (2) lauryl ether, polyoxyethylene (3) monostearate, polyoxyethylene (6) cetyl ether and polyoxyethylene (5) stearyl ether and Myreth-3-Myristate (CTFA name) available commercially as "Cetiol 1414-E®". Other suitable emulsifiers included cetyl phosphate salts and alkyl dimethicone copolyol, the latter commercially available as ABIL EM90 emulsifier from Goldschmidt AG of Germany. Phosphatides such as lecithin may also be useful as emulsifiers in the compositions of the invention.

In another aspect, the compositions of the invention include from about 0.1 to about 95 percent by weight of natural fats or oils, from about 0.1 to about 10 percent by weight of sterols or sterol derivatives, from about 1 to about 95 percent by weight of emollient, from about 0.1 to about 40 percent by weight of viscosity enhancer and from about 0.1 to about 10 percent by weight of extracted botanical active. The compositions may also include from about 5 to about 95 percent by weight of solidifying agent. In such aspects, the compositions of the invention can include fats and oils that provide a source of essential and non-essential fatty acids similar to those found in the skin's natural barrier. Fats and oils include compounds that are fats, oils, essential oils, fatty acids, fatty alcohols, phospholipids and mixtures of such compounds. Fats and oils include oils derived from plant and animal sources. Similarly, the essential oils include essential oils derived from plant sources. Those of skill in the art would understand that all compounds commonly understood to have the structure of or to function as fats, oils, essential oils, fatty acids, fatty alcohols and phospholipids can be used as the natural fat or oil component of the composition of the invention. While an exhaustive list of each and every fat and oil that could be used in the compositions of the invention is not provided, those of skill in the art will understand and appreciate the individual compounds that can serve as a fat or oil component of the compositions of the invention.

Representative examples of fats and oils include, but are not limited to: Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lanolin, Lanolin Alcohol, Lauric Acid, Palmitic Acid, Stearic Acid, Linoleic Acid, Stearyl Alcohol, Lauryl Alcohol, Myristyl Alcohol, Behenyl Alcohol, Rose Hip Oil, Calendula Oil, Chamomile Oil, Eucalyptus Oil, Juniper Oil, Sandlewood Oil, Tea Tree Oil, Sunflower Oil, and Soybean Oil. Another suitable fat/oil for the compositions of the invention is PROLIPID 141 blend available from International Specialty Products of Wayne, N.J. The PROLIPID 141 blend is a mixture of glyceryl stearate, fatty acids, fatty alcohols and phospholipids.

In order to assist in replenishing skin barrier enhancing agents, the compositions of the invention may include fats and oils in an amount of from about 0.1 to about 95 percent by weight, desirably from about 5 to about 75 percent by weight, and more desirably from about 10 to about 50 percent by weight of the composition.). In particular aspects, the fats and oils can be at least a minimum of about 0.1 percent by weight. The fats and oils can alternatively be at least about 5 percent, and optionally, can be at least about 10 percent to provide improved performance. In other aspects, the fats and oils can be not more than a maximum of about 95 percent by weight. The fats and oils can alternatively be not more than about 75 percent, and optionally, can be not more than about 50 percent to provide improved effectiveness.

The compositions of the invention also include sterols and sterol derivatives that act in combination with the natural fats/oils to provide natural skin barrier enhancement and skin barrier recovery. Sterols and sterol derivatives that can be used in the compositions of the invention include, but are not limited to: β-sterols having a tail on the 17 position and having no polar groups for example, cholesterol, sitosterol, stigmasterol, and ergosterol, as well as, $C_{10}$–$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyidecanoate, ergocalciferol, tall oil sterol, soy sterol acetate, lanasterol, soy sterol, avocado sterols, "AVOCADIN" (trade name of Croda Ltd of Parsippany, N.J.), sterol esters and similar compounds, as well as mixtures thereof. The compositions of the invention can include sterols, sterol derivatives or mixtures of both sterols and sterol derivatives in an amount of from about 0.1 to about 10 percent by weight, desirably from about 0.5 to about 5 percent by weight and more desirably from about 0.8 to about 1 percent by weight of the composition.). In particular aspects, the sterols can be at least a minimum of about 0.1 percent by weight. The sterols can alternatively be at least about 0.5 percent, and optionally, can be at least about 0.8 percent to provide improved performance. In other aspects, the sterols can be not more than a maximum of about 10 percent by weight. The sterols can alternatively be not more than about 5 percent, and optionally, can be not more than about 1 percent to provide improved effectiveness.

The compositions of the invention may also include one or more rheology modifiers. Rheology modifiers are compounds that increase the viscosity of the compositions at lower temperatures as well as process temperatures. Rheology modifiers or suspending agents are also compounds that provide "structure" to the compositions to prevent settling out (separation) of insoluble and partially soluble components. By increasing the viscosity at process temperatures, the rheology modifiers will increase the viscosity above 200 centipoise. However, the rheology modifiers are thixotropic in behavior and, therefore, their viscosity decreases as shear and pressure increases. Consequently, when the rheology modifiers are used in the compositions of the invention, they maintain the suspension of insoluble and partially soluble components. This capability can be particularly important if, during processing, the composition must be left stagnant in process lines and hoses. The rheology modifiers will maintain the suspension of the insoluble and partially soluble components for a period of time that depends on the viscosity of the composition and on the amount of rheology modifier present. The thixotropic behavior of the rheology modifiers causes their viscosity to drop when processing is resumed and the composition is no longer stagnant due to the application of pressure and shear forces. The rheology modifiers provide different benefits than the viscosity enhancers described herein. The viscosity enhancers increase the melt-point viscosity of the compositions, but the viscosity enhancers may not provide the correct rheology to suspend insoluble particulates or materials.

In addition to stabilizing the suspension of insoluble and partially soluble components, the rheology modifiers of the invention also help to stabilize the compositions on the bodyfacing or other materials to which the compositions are applied. Examples of suitable rheology modifiers include silica, silica silylate, silica methyl silylate, quaternary starch compounds, quaternary clay compounds, organically modified clays and mixtures thereof. The organically modified clays are typically used in combination with an activator such as propylene carbonate, ethanol, propanol, acetone, alpha hydroxy acids or mixtures of such activators. Such rheology modifiers can help maintain the suspension of an insoluble or partially soluble emollient, such as a siloxane, within the composition. The compositions of the invention can include from about 0.5 to about 20 percent by weight of one or more rheology modifiers.

The use of one or more than one rheology modifier, such as an organically modified clay in combination with a silica, can provide a benefit to the rheology of the compositions by increasing the viscosity of the compositions at process temperatures. When a silica, an organically modified clay or both are used in an ointment or lotion type composition, it is expected that they will increase the hardness of the composition and, consequently, have a negative effect on transfer of the ointment to the skin. However, when a natural clay or a synthetic analog of a natural clay is used in combination with an organically modified clay or a silica, there is an unexpected, synergistic enhancement of the rheology of the composition. The organically modified clay and silica assist the suspension of the natural clay (or synthetic analog of the natural clay) in the compositions of the invention. When a natural clay is combined with an organically modified clay or a silica, a small amount of shear (such as rubbing) will unexpectedly cause the composition to become soft and to spread easily. Therefore, when such a combination is used in the compositions of the invention, there is an improvement in the transfer of the composition from the bodyside liner of the article to the skin. Though these compositions provide improved transfer from the liner to the skin, they remain stable on the bodyside liner under storage conditions. Natural clays include montmorillonite, bentonite, beidellite, hectorite, saponite, stevensite, magnesium aluminum silicate and similar clays. Synthetic analogs of natural clays, such as LAPONITE synthetic clay available from Southern Clay Products Inc. of Gonzales, Tex. can also be used to provide the rheology benefit to compositions of the invention when used in combination with organically modified clays or silica. Natural clays and synthetic analogs of natural clays can be included in the compositions of the invention in amounts of from about 0.5 to about 20 percent by weight of the composition.

The unexpected benefits provided by the combination of natural clay with organically modified clay or silica in the compositions of the invention are demonstrated by tests measuring the relationship between the amount of composition transferred and the penetration hardness of the composition. Prior to identifying the benefits provided by combining natural clay with organically modified clays or silicas, it was believed that as the penetration hardness of a composition was increased, the less that composition could be transferred. The penetration hardness of a composition is typically measured using the standardized method of ASTM D1321. A method has been developed for measuring the amount of composition transferred from a surface. Composition transfer is measured using an Ink Rub Tester such as Model #10-18-01 manufactured by Testing Machines Inc. For purposes of the method described herein, the Ink Rub Tester is set to have the following settings: (1) Cycles=50; (2) Cycles/minute=100; (3) Alarm=on; (4) Pause every=off; and (5) Count=down. A four pound weighted block is used in order to more closely simulate the pressure applied by an infant to an absorbent article, such as a diaper, while sitting or moving. The receptor or receiving material is held to the four pound weighted block by four magnets. The four magnets are positioned so that there are two evenly spaced on either side of the four pound weighted block. Typically, the receptor material is Natural Silk Noil, style #651, which is available from Testfabrics, Inc. The receptor material is cut to have dimensions of 2 inches by 6 inches. Desirably, the magnets are high powered neodymium magnets having a diameter of 0.25 inches and a height of 0.25 inches. Preferably, the tension on the receptor material is uniform and the receptor material is held tightly with no gaps between the weighted block and the receptor material. The receptor material should not, however, be subjected to extraordinary strain.

The base or liner material that is treated with a composition is centered on a rubber pad that will be brought into contact with the four pound weighted block during the test. The liner material is typically an spunbond liner material with UVITEX fluorescener laced add-on. The planar dimension of the rubber pad is approximately 2.5 inches by 6 inches. The liner material is usually cut to dimensions of approximately 3 inches by 9 inches in order to completely cover the rubber pad. A composition is applied to the liner material using a slot-coating or spraying technique. Desirably, the slot-coated lines of composition are aligned lengthwise with the length of the rubber pad and the lines are centered as much as possible. Both ends of the rubber pad have strips of hook 88 VELCRO tape adhered to them. The liner material is held in place on the rubber pad by pressing the liner material against the VELCRO tapes. The liner material should be as wrinkle-free as possible when positioned against the rubber pad. Two three inch wide IDL ball bearing clips are then attached to either end of the rubber pad in order to hold the liner material in place and to prevent movement of the liner material.

Prior to attachment to the four pound weighted block, the receptor material should be weighed on a balance that is significant to at least decimal places. Prior to placement on the weighing plate of the balance, the receptor material should be tri-folded so that no portion is hanging off of the weighing plate. Care should be taken to make sure there are no threads hanging from the receptor material as well. The initial mass of the receptor material is recorded. Gloves should be worn during handling of each of the materials in order to prevent transfer of oils naturally present on hands to the test materials. Once both the receptor material and liner material are secured, the test is conducted using the Ink Rub Tester settings described previously. At the end of the test, the liner material is removed and thrown away. The receptor material is removed and sprayed with Milty Zerostat 3 Anti-Static Pistol available from SPI Supplies. After removal of static, the receptor material is once again tri-folded and its mass is recorded using the balance. The change in mass is the difference between the initial and final masses of the receptor material and is representative of the amount of composition transferred from the liner material.

A series of Ink Rub Tester tests were conducted on "control" compositions including only petrolatum and a wax and test compositions representative of compositions of the invention containing natural clay in combination with organically modified clay or silica. The penetration hardnesses of the compositions were also measured using the standardized test method identified previously. Descriptions of the compositions, the penetration hardnesses and the amounts transferred (as measured by the Ink Rub Tester test method) are provided in Table 1 below. Each of the liner materials used in the Ink Rub Tester tests had 0.40 grams of composition applied by slot coating.

TABLE 1

| Test Composition | Average Penetration Hardness (millimeters) | Average Amount Transferred |
|---|---|---|
| 80% Petrolatum 20% Ozokerite Wax | 23.1 | 0.0223 |
| 60% Petrolatum 40% Ozokerite Wax | 8.9 | 0.0106 |
| 40% Petrolatum 60% Ozokerite Wax | 6.6 | 0.0042 |
| 20% Petrolatum 80% Ozokerite Wax | 1.6 | 0.0012 |
| Composition A | 5.2 | 0.0124 |
| Composition B | 7.4 | 0.0166 |

Figure 4:
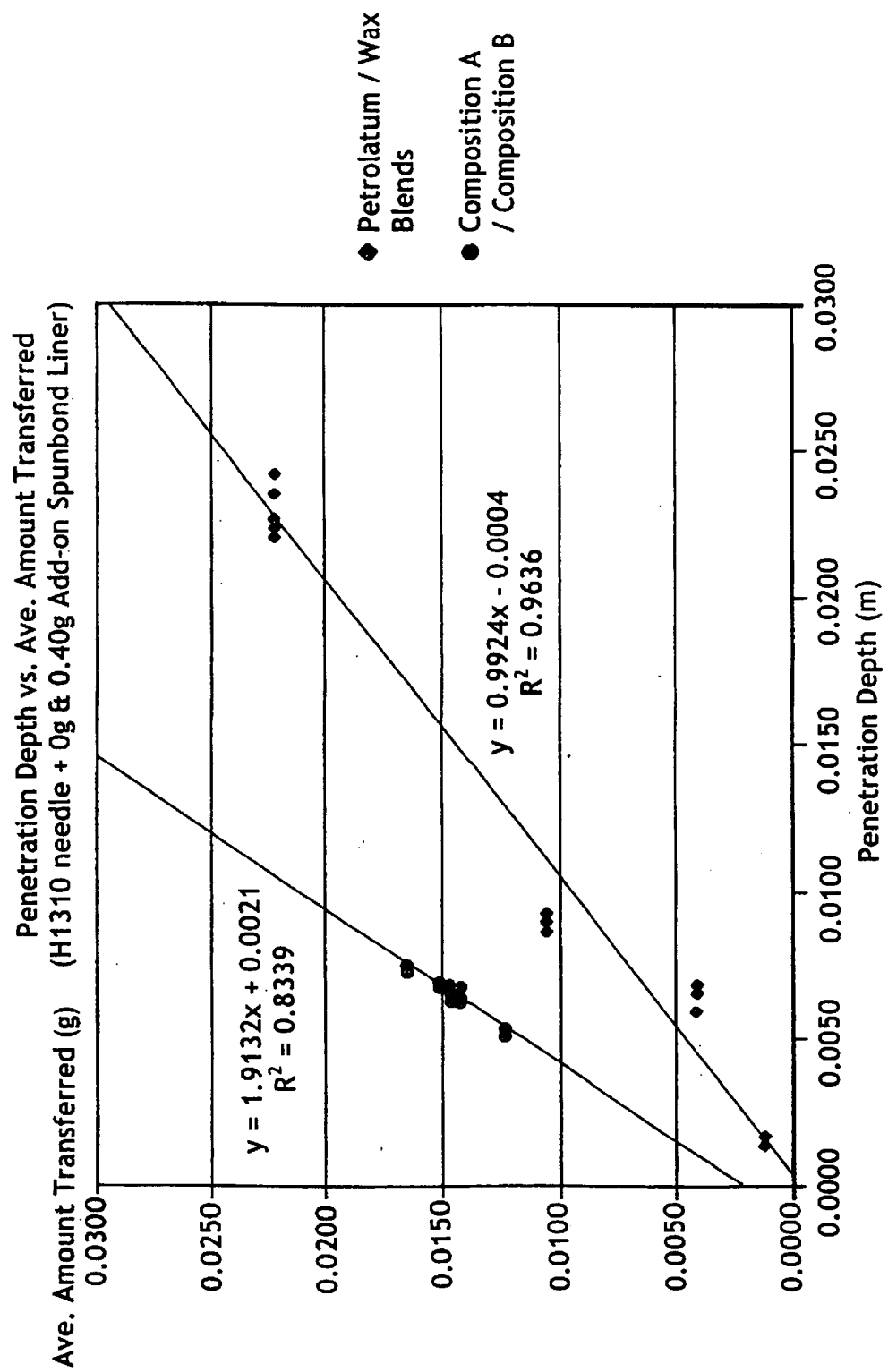
FIG. 4 graphically represents the relationship between transfer amount and penetration hardness for compositions of the invention and previously known compositions.

The average penetration hardness measurements are based on a sample size of ten. The average amount transferred measurements are based on a sample size of ten. Composition A includes 39.7% petrolatum; 36% ozokerite wax; 1% alkyl silicone wax; 10% sunflower oil; 0.8% soy sterol; 1% PROLIPID 141 blend; 2% dimethicone; 7.5% LAPONITE synthetic analog bentonite clay; and 2% fumed silica. Composition B includes 37.2% petrolatum; 36% ozokerite wax; 1% alkyl silicone wax; 10% sunflower oil; 0.8% soy sterol; 1% PROLIPID 141 blend; 2% dimethicone; 10% LAPONITE synthetic analog bentonite clay; and 2% fumed silica. The values for average amount transferred are plotted against the values for average penetration hardness in FIG. 4. An "H1310 Needle" is a reference to a specific part of the penetrometer used for the hardness measurements. With the non-natural clay compositions, there is a linear relationship between amount transferred and penetration hardness. With the natural clay containing compositions, there is also a linear relationship between the amount transferred and penetration hardness, however, the slope of the line is significantly greater. Therefore, unexpectedly, for two compositions of the same penetration hardness, for example 0.01 meters, the non-natural clay composition would transfer 0.0095 grams of composition while the natural clay-containing composition would transfer 0.021 grams of composition.

In order to more fully elaborate upon the unexpected benefit of combining a natural clay or synthetic analog of a natural clay with a rheology modifier, the relationship between viscosity and shear rate was determined for various compositions of the invention. Ideally, compositions applied to the bodyfacing surfaces of absorbent articles have a high viscosity at the stability-measuring temperature of 54.5° C. and a low shear rate in order to minimize migration of the composition away from the bodyfacing surfaces. Previously, it was thought that if a composition had a melting point greater than 55° C., the composition would not migrate. However, in reality, such compositions would have components with melting points below the bulk melting point of the composition. Those lower melting point components would soften the composition and migration would occur. Addition of the viscosity enhancers of the invention to compositions results in significantly greater stability—even when the composition has a bulk melting point below 54.5° C. Even better stability is achieved when compositions include a rheology modifier and a natural clay (or synthetic analog of a natural clay) and, unexpectedly, and as shown by the Ink Rub Test results, the compositions have improved transfer to the skin of the wearer of the absorbent article.

Figure 5:
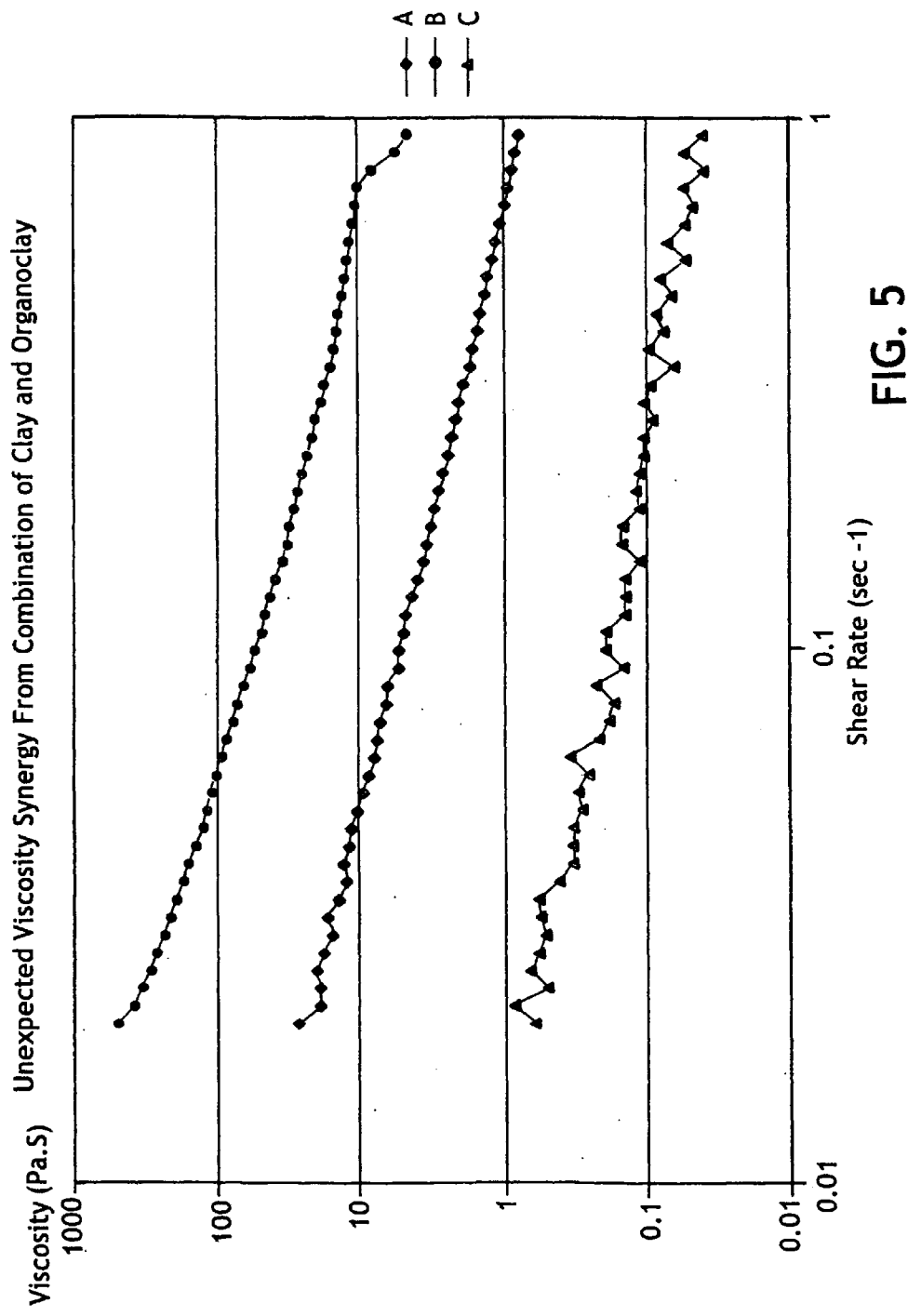
FIG. 5 graphically represents the relationship between viscosity and shear rate for compositions of the invention and previously known compositions.

FIG. 5 shows a plot of viscosity versus shear rate and evidences the unexpected benefits provides by the compositions of the invention. The viscosity of several compositions was measured at 75° C. over increasing shear rates. The temperature of 75° C. was selected to represent a processing temperature. The compositions for which viscosity was measured are described in Table 2 below.

TABLE 2

| Composition Component | Composition A | Composition B | Composition C |
|---|---|---|---|
| Petrolatum | 95% | 97.4% | 92.4% |
| CLAYTON HY organomodified clay | | 2% | 2% |
| Propylene Carbonate | | 0.6% | 0.6% |
| POLAR GEL NF natural clay | 5% | | 5% |

CLAYTON HY is an organically modified clay that is available from Southern Clay Company and represents a rheology modifier of the invention. Propylene carbonate is an activator that activates the organically modified clay. POLAR GEL NF is a natural clay that is available from American Colloid. The relationship between viscosity and shear rate is plotted for compositions A–C in FIG. 5. The relationship between viscosity and shear rate can be defined by the following equations for each composition:

| Composition A: | $y = 0.0384x^{-0.7163}$ |
| Composition B: | $y = 0.6816x^{-0.8911}$ |
| Composition C: | $y = 5.2332x^{-1.0574}$ |

The results portrayed in FIG. 5 show the synergistic benefit of combining a rheology modifier with a natural clay (or a synthetic analog of a natural clay). Composition A, including a natural clay, has the lowest viscosity over the range of shear rates. Composition B, including an organically modified clay, has the next highest viscosity over the range of shear rates. However, Composition C, including both an organically modified clay and a natural clay, maintains the highest viscosity over the range of shear rates. A similar set of experiments were conducted for silica-containing compositions. The compositions are described in Table 3. below.

TABLE 3

| Composition Component | Composition A | Composition B | Composition C |
|---|---|---|---|
| Petrolatum | 54.9% | 57.9% | 52.9% |
| Microcrystalline Wax | 40% | 40% | 40% |
| Silica (M5) | | 2% | 2% |
| POLAR GEL NF Natural clay | 5% | | 5% |
| UV Tracers | 0.1% | 0.1% | 0.1% |

Figure 6:
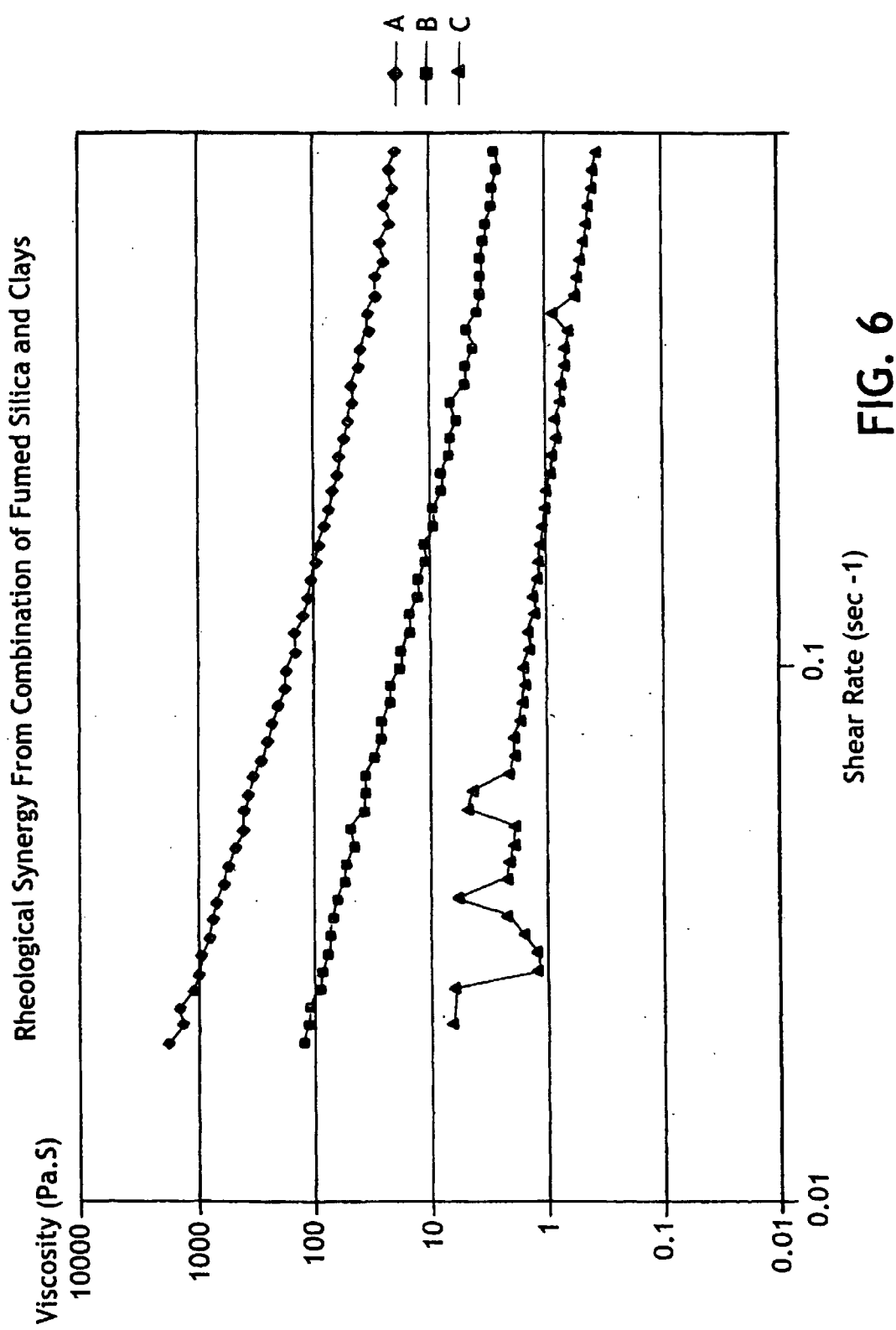
FIG. 6 graphically represents the relationship between viscosity and shear rate for compositions of the invention and previously known compositions.

The relationship between viscosity and shear rate for compositions A–C (described in Table 3.) is depicted in FIG. 6.

The relationship between viscosity and shear rate can be defined by the following equations for each composition:

| | |
|---|---|
| Composition A: | $y = 0.3958x^{-0.5941}$ |
| Composition B: | $y = 1.8522x^{-1.0518}$ |
| Composition C: | $y = 13.191x^{-1.1664}$ |

Composition A, including a natural clay, has the lowest viscosities over the range of shear rates. Composition B, including silica, has a higher viscosity over the range of shear rates. Composition C, including both silica and natural clay, has the highest viscosities over the range of shear rates and exhibits strong thixotropic behavior as evidenced from the large negative exponential value. The combination of the rheology modifier, silica, with a natural clay provides a synergistic beneficial effect on the viscosities of the compositions of the invention. Though viscosities increase, as described previously, the compositions of the invention show improved transfer from a liner-type material.

If it is desired that the composition provide a treatment for the skin, the composition can also include an active ingredient such as a diaper rash skin protectant. Skin protectants are drug products that protect injured or exposed skin or mucous membrane surface from harmful or annoying stimuli. Suitable active ingredients, in addition to those mentioned above as suitable emollients, that can be incorporated into the composition include, but are not limited to, allantoin and its derivatives, aloe, aluminum hydroxide gel, calamine, cocoa butter, dimethicone, cod liver oil, glycerin, kaolin and its derivatives, lanolin and its derivatives, mineral oil, petrolatum, shark liver oil, talc, topical starch, zinc acetate, zinc carbonate, zinc oxide and the like, and mixtures thereof. The composition may include from about 0.10 to about 95 percent by weight of the active ingredient depending upon the skin protectant, the amount desired to be transferred to the skin or the amount of a particular skin protectant required in the U.S. Food and Drug Administration monograph.

In order to better enhance the benefits to the wearer, additional ingredients can be included in the compositions of the present invention. For example, the classes of ingredients that may be used and their corresponding benefits include, without limitation: antifoaming agents (reduce the tendency of foaming during processing); antimicrobial actives; antifungal actives; antiseptic actives; antioxidants (product integrity); antioxidants-cosmetic (reduce oxidation); astringents-cosmetic (induce a tightening or tingling sensation on skin); astringent-drug (a drug product that checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); other emollients (help to maintain the soft, smooth, and pliable appearance of the skin by their ability to remain on the skin surface or in the stratum corneum to act as lubricants, to reduce flaking, and to improve the skin's appearance); external analgesics (a topically applied drug that has a topical analgesic, anesthetic, or antipruritic effect by depressing cutaneous sensory receptors, or that has a topical counterirritant effect by stimulating cutaneous sensory receptors); film formers (to hold active ingredients on the skin by producing a continuous film on skin upon drying); fragrances (consumer appeal); silicones/organomodified silicones (protection, water resistance, lubricity, softness); oils (mineral, vegetable, and animal); natural moisturizing agents (NMF) and other skin moisturizing ingredients known in the art; opacifiers (reduce the clarity or transparent appearance of the product); powders (enhance lubricity, oil adsorption, provide skin protection, astringency, opacity, etc.); skin conditioning agents; solvents (liquids employed to dissolve components found useful in the cosmetics or drugs); and surfactants (as cleansing agents, emulsifying agents, solubilizing agents, and suspending agents).

An important property of the compositions of the different aspects of the present invention is their ability to remain on the surface of the bodyside liner 22 and their resistance to migration into the diaper 10 such that they can readily be transferred to the wearer's skin. In this regard, the articles having the compositions of the present invention applied to their bodyside liner 22 define a z-direction migration loss of no more than about 55%, desirably no more than about 50%, more desirably no more than about 45%, even more desirably no more than about 40% and yet even more desirably no more than about 35% when subjected to the Z-Direction Lotion Migration Test set forth below. In articles that have a greater z-direction migration loss, the composition undesirably migrates into the interior and along the surface of the bodyside liner 22 and at times through the bodyside liner 22 into the absorbent body 24 of the article which results in a lower reduction in abrasion and less transfer to the skin of the wearer.

Another important measure of the compositions of the different aspects of the present invention is their ability to resist migration laterally along the surface of the bodyside liner 22. In this regard, the articles having the compositions of the present invention applied to the bodyside liner 22 define a cd-direction migration loss of no more than about 40%, desirably no more than about 35%, more desirably no more than about 30%, even more desirably no more than about 25% and yet even more desirably no more than about 20% when subjected to the CD-Direction Lotion Migration Test set forth below. In articles which have a greater cd-direction migration loss, the composition undesirably migrates along the surface of the bodyside liner 22 and at times through the bodyside liner 22 into the absorbent body 24 of the article which results in a lower reduction in abrasion and less transfer to the skin of the wearer.

Moreover, to provide the improved stability and transfer to the skin of the wearer, the compositions of the present invention may define a melting point of from about 32° C. to about 100° C., desirably from about 35° C. to about 80° C., and more desirably from about 40° C. to about 75° C. Compositions that have lower melting points exhibit migration of the composition during use and at elevated temperatures in storage that can undesirably result in reduced transfer to the skin. Whereas, compositions that have higher melting points may require that the composition be at a temperature above the flash point of the bodyside liner 22 material which can undesirably lead to fires. The melting points of the compositions of the invention cause the compositions to be relatively immobile and localized on the bodyfacing surface 11 of the diaper 10 at room temperature and readily transferable to the skin of the wearer at body temperatures. However, the compositions of the invention are not completely liquid under extreme storage conditions. Desirably, the compositions are easily transferable to the skin by way of normal contact, wearer motion, adhesion or body heat. When the compositions are relatively immobilized at room temperature, a lesser quantity of composition is required on the bodyfacing surface 11 to provide a beneficial effect.

The composition of the present invention may further define a low shear viscosity at about 55° C. of greater than about 50,000 centipoise, desirably from about 50,000 to about 1,000,000 centipoise, and more desirably from about 100,000 to about 800,000 centipoise for reduced migration and improved transfer to the skin of the wearer. Compositions that have lower melt point viscosities exhibit migration of the composition through the bodyside liner 22 into the absorbent body 24 of the article which can undesirably result in reduced transfer to the skin. Whereas, compositions that have higher melt point viscosities may be so solid as to also exhibit a reduced transfer to the skin.

Further, to provide the improved stability and transfer to the skin of the wearer, the compositions of the present invention may also define a high shear viscosity of less than about 5,000 centipoise, desirably from about 100 to about 500 centipoise, and more desirably from about 150 to about 250 centipoise at a temperature of about 60° C. (or higher temperatures depending on the components and melting point of the composition).

The penetration hardness of the compositions of this invention can be from about 5 to about 365 millimeters, more desirably from about 10 to about 300 millimeters, more desirably from about 20 to about 200 millimeters, and still more desirably from about 40 to about 120 millimeters at 25° C. (Compositions having a needle penetration hardness greater than 365 millimeters cannot be measured using ASTM method D 1321). The hardness of the compositions of this invention is important for two reasons. First, the softer the formulation the more mobile the formulation will be, making the formulation more likely to migrate to the inner plies of the diaper 10, which is not desirable. Secondly, softer compositions tend to be more greasy/oily to the touch, which is also less desirable.

Figure 3:
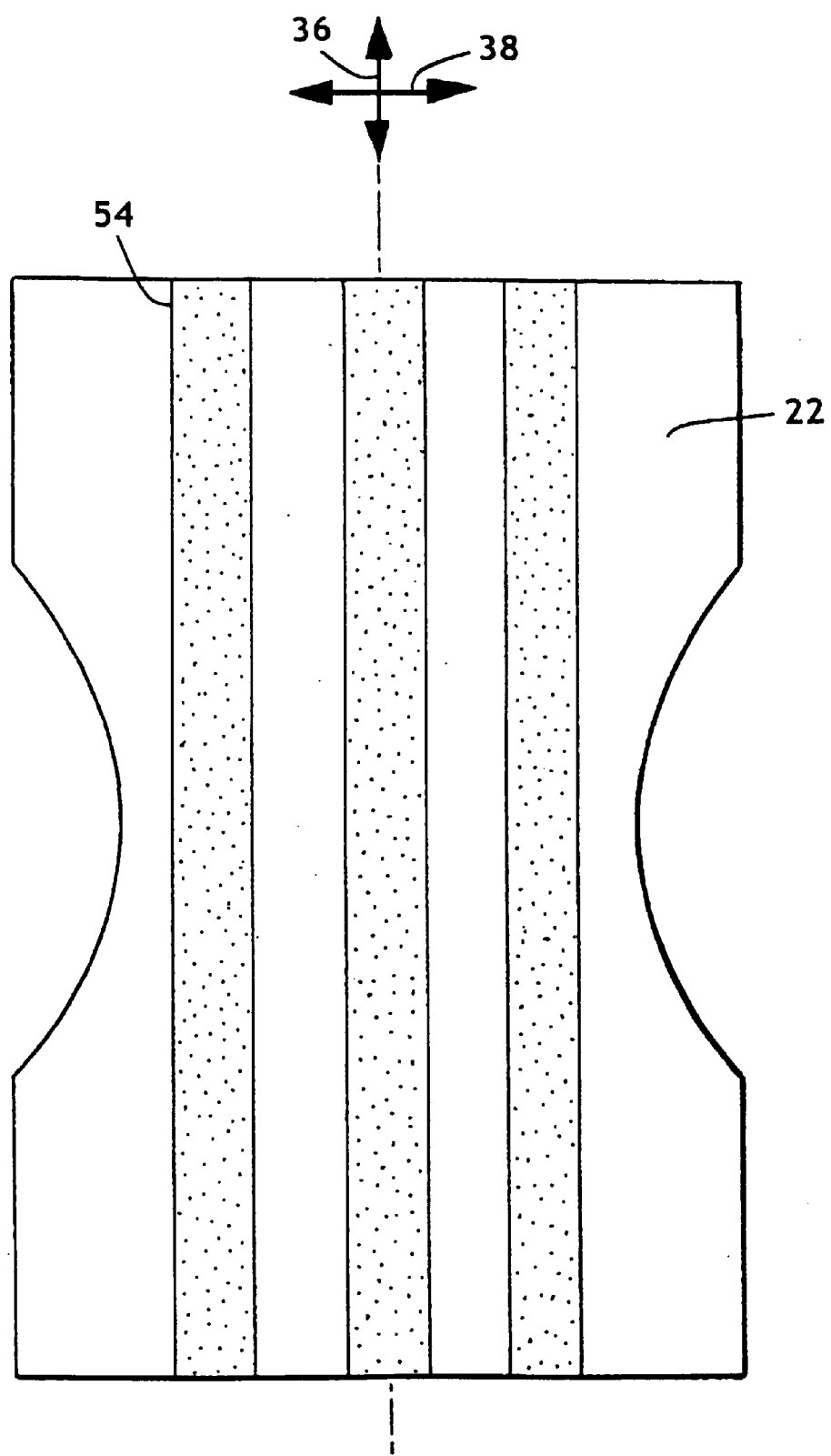
FIG. 3 representatively shows a top plan view of the bodyside liner of the absorbent article of FIG. 1 with the surface that contacts the wearer facing the viewer.

The composition may be applied to the entire bodyfacing surface 11 of the bodyside liner 22 or may be selectively applied to particular sections of the bodyfacing surface 11, such as the medial section along the longitudinal centerline of the diaper 10, to provide greater lubricity of such sections and to transfer such composition to the wearer's skin. Alternatively, the bodyfacing surface 11 of the bodyside liner 22 may include multiple stripes of the composition applied thereto as illustrated in FIG. 3. For example, the bodyfacing surface 11 of the bodyside liner 22 may include from 1 to 20 stripes 54 of composition extending along the longitudinal direction of the diaper 10. The stripes 54 may extend the full length of the bodyside liner 22 or only a portion thereof. The stripes 54 may also define a width of from about 0.2 to about 1 centimeters.

The composition should cover a sufficient amount of the bodyfacing surface 11 of the bodyside liner 22 to ensure adequate transfer to the skin and reduced abrasion between the bodyside liner 22 and the wearer's skin. Desirably, the composition is applied to at least about 5 percent and more desirably at least about 25 percent of the bodyfacing surface 11 of the bodyside liner 22.

The composition can be applied to the bodyside liner 22 at any add-on level that provides the desired transfer benefit. For example, the total add-on level of the composition can be from about 0.05 to about 100 mg/cm$^2$, desirably from about 1 to about 50 mg/cm$^2$ and more desirably from about 10 to about 40 mg/cm$^2$ for improved performance. The add-on amount will depend upon the desired effect of the composition on the skin barrier function and the specific composition. As discussed above, the improved stability and reduced tendency to migrate of the compositions of the present invention allows a lesser amount of composition to be applied to the bodyside liner 22 to achieve the same benefit when compared with conventional compositions.

The composition may be applied to the bodyside liner 22 in any of many well known manners. A preferred method to uniformly apply the composition to the bodyfacing surface 11 of the bodyside liner 22 is spraying or slot coating. Spraying or slot coating the composition is the most exact process and offers maximum control of the composition distribution and transfer rate. However, other methods, such as rotogravure or flexographic printing and foam application can be used. The compositions of the present invention can be applied after the bodyfacing material has been incorporated into the absorbent article or prior to incorporating the body facing material into the absorbent article.

The composition may be applied to the bodyside liner 22 by (a) heating the composition to a temperature above the melting point of the composition, causing the composition to melt, (b) uniformly applying the melted composition to the bodyfacing surface 11 of the bodyside liner 22; and (c) resolidifying the composition applied to the bodyfacing surface 11. Desirably, resolidification of the composition occurs almost instantaneously, without the need for external cooling devices such as chill rolls. This can occur if the composition is heated to a temperature only slightly above or at the melting point of the composition. However, external cooling devices such as chill rolls, either before or after the application of melt, can be used if desired to accelerate resolidification. Other cooling methods such as cooling tunnels could also be used.

The increased viscosity of the composition at the process temperature and the instantaneous resolidification tends to impede penetration of the composition into the bodyside liner 22 and absorbent body 24 of the diaper 10 and retain it on the bodyfacing surface 11 of the bodyside liner 22, which is advantageous. For example, the temperature of the melted composition can advantageously be less than about 20° C., more desirably less than about 10° C., and still more desirably less than about 5° C. above the melting point of the composition prior to applying it to the bodyside liner 22 for reduced migration. As the temperature of the melted composition approaches the freezing point of the composition, the viscosity of the melted composition generally increases, which further enhances the tendency of the melted composition to be retained on the bodyfacing surface 11.

The present invention is also directed to an absorbent article, such as a diaper 10, that includes an outer cover 20, a liquid permeable bodyside liner 22, an absorbent body 24 and a composition. The bodyside liner 22 defines a bodyfacing surface 11. As already described herein, the bodyfacing surface 11 is that portion of the article that comes into contact with the skin of the wearer or user of the article. When the article is a diaper 10, the bodyfacing surface 11 typically is primarily the bodyside liner 22, but the bodyfacing surface 11 can also include waist and leg elastics 26, 28, containment flaps and fasteners 30. When the article is a primarily two-dimensional substrate such as a tissue or wet wipe, the entire surface area of the tissue or wet wipe is the bodyfacing surface 11 as any portion of such articles may contact the user's skin.

The bodyside liner 22 is in superposed relation to the outer cover 20. The —20 absorbent body 24 is located between the bodyside liner 22 and the outer cover 20. At least a portion of the bodyfacing surface 11 of the bodyside liner 22 has a composition on it. The composition may include from about 0.5 to about 75 percent by weight of natural fats or oils. The natural fats and oils can be selected from avocado oil, borage oil, sunflower oil, soybean oil, corn oil, cottonseed oil and mixtures of these compounds. The composition may also include from about 0.5 to about 5 percent by weight of sterols or sterol derivatives. The sterols and sterol derivatives can be selected from cholesterol, sitosterol, stigmasterol, tall oil sterol, soy sterol and mixtures of these compounds. Additionally, the composition includes from about 20 to about 75 percent by weight of one or more emollients. The emollients can be selected from petrolatum, silicone oils, dimethicone, lanolin and mixtures of these compounds. The composition may include from about 25 to about 75 percent by weight of one or more solidifying agents. The solidifying agents may be selected from cerasin, microcrystalline wax, ozokerite, alkylmethylsiloxanes including alkyl silicones and mixtures of these compounds. The composition may also include from about 5 to about 40 percent by weight of one or more viscosity enhancers. The viscosity enhancers can be selected from ethylene/vinyl acetate copolymers, polyethylene, silica and mixtures of these compounds. The composition further includes from about 0.1 to about 10 percent by weight of one or more extracted botanical actives. The extracted botanical actives can be selected from extracts taken from plants of echinacea, yucca, willow herb, green tea, black tea, oolong tea, Chinese tea and mixtures of these extracts.

The composition has physical properties that are suitable to provide a relative degree of immobilization on the bodyfacing surface 11 at room temperature and to provide sufficient fluid or transfer properties at body temperature so that the composition can migrate to the skin. Typically, the composition has a melting point of from about 32° C. to about 100° C. and a viscosity of less than about 5,000 centipoise at a temperature of about 60° C. The composition has a viscosity of greater than about 50,000 at a temperature of about 55° C. The composition may also have a penetration hardness of from about 5 millimeters to about 365 millimeters at 25° C. The composition is typically present on the bodyfacing surface 11 in an amount of from about 0.1 g/m² to about 30 g/m². The composition applied to the bodyfacing surface 11 may have additional ingredients added to it in order to provide additional benefits or to enhance the functionality and processability of the composition.

The present invention is also directed to a method of applying a composition to a bodyfacing surface 11 of a bodyside liner 22 of an absorbent article. The method includes a step of heating a composition to a temperature above the melting point of the composition. The composition generally protects the skin barrier and reduces inflammation and can include an emollient, a viscosity enhancer and an extracted botanical active. The composition can also include natural fats or oils, sterols or sterol derivatives, solidifying agents, rheology modifiers and clays. The melting point of the composition is from about 32° C. to about 100° C. The method also includes a step of applying the composition to the bodyfacing surface 11 of a bodyside liner 22 of an absorbent article. The method further includes a step of resolidifying the composition. The composition can be applied to the bodyfacing surface 11 using any of the techniques already describe herein such as foam application, spraying, slot coating and printing. The composition can be resolidified using devices that are commonly used for cooling, such as chill rolls and cooling tunnels, or the composition can be resolidified or become very viscous by selecting a combination of ingredients that puts the melting point or high viscosity close to the processing temperature. When the melting point of the composition is close to the processing temperature, the composition should quickly resolidify or become very viscous after application to the bodyfacing surface 11. Typically, after resolidification, the composition has a viscosity of greater than about 50,000 centipoise and a penetration hardness of from about 5 to about 365 millimeters at 25° C.

The present invention is further directed to a method for protecting the skin barrier on a skin surface of a user. The method includes a step of contacting a skin surface of a user of an absorbent article with a bodyfacing surface 11 of a bodyside liner material. The method could also include a step of contacting the skin surface of a user of a tissue or wet wipe article with the outer surface of the material from which the tissue or wet wipe is constructed. The bodyfacing surface 11 or outer surface has a composition on it. The composition can include an emollient, a viscosity enhancer and an extracted botanical active. The relative amounts and combinations of composition components can be varied. The method of the invention also includes a step of maintaining the bodyfacing surface 11 in contact with the skin surface of the user for a sufficient amount of time to transfer the composition to the skin surface. The amount of time is related to the nature of the composition and its physical properties; different compositions will transfer to a skin surface at different rates. The method further includes a step of repeating the maintaining step for a sufficient period of time to evidence enhancement of skin barrier function. Therefore, the method includes repeating the contact of the skin surface with the bodyfacing surface 11 of the liner material.

As suggested by the compositions already described herein, the composition applied to the bodyfacing surface 11 can include from about 50 to about 95 percent by weight of one or more emollients, from about 1 to about 40 percent by weight of one or more viscosity enhancers and from about 0.1 to about 10 percent by weight of one or more extracted botanical actives. Examples of suitable emollients, viscosity enhancers and extracted botanical actives are as described herein.

The descriptions of the articles and compositions of the invention provided herein have included references to various tests for assessing the attributes or properties of the components of the articles and compositions as well as the articles and compositions in their entireties. Descriptions of the test procedures used to make those assessments are now provided.

Hydrostatic Pressure Test

The Hydrostatic Pressure Test is a measure of the liquid barrier properties of a material. In general, the Hydrostatic Pressure Test determines the height of water (in centimeters) in a column that the material will support before a predetermined amount of water passes through. A material with a higher hydrohead value indicates it is a greater barrier to liquid penetration than a material having a lower hydrohead value. The Hydrostatic Pressure Test is performed according to Method 5514—Federal Test Methods Standard No. 191A.

Frazier Porosity Test

The Frazier Porosity values referred to in the present specification can be determined employing a Frazier Air Permeability Tester (Frazier Precision Instrument Co., Gaithersburg, Maryland) and Method 5450, Federal Test Methods Standard No. 191A. For the purposes of the present invention, the test is conducted with a sample that measures 8 inches×8 inches.

Water Vapor Transmission Test

A suitable technique for determining the WVTR (water vapor transmission rate) value of a material is as follows. For the purposes of the present invention, 3-inch diameter (76 millimeter) circular samples are cut from the test material and from a control material, CELGUARD 2500 material (Hoechst Celanese Corporation). Two or three samples are prepared for each material. Test cups used for testing are cast aluminum, flanged, 2 inches deep and come with a mechanical seal and neoprene gasket. The cups are distributed by Thwing-Albert Instrument Company, Philadelphia, Pa., under the designation "Vapometer cup #681". One hundred milliliters of distilled water are poured into each Vapometer cup, and each of the individual samples of the test materials and control material are placed across the open top area of an individual cup. Screw-on flanges are tightened to form a seal along the edges of the cups leaving the associated test material or control material exposed to the ambient atmosphere over a 62 millimeter diameter circular area (an open, exposed area of about 30 cm$^2$). The cups are then weighed, placed on a tray, and set in a forced air oven set at 100° F. (38° C.). The oven is a constant temperature oven with external air circulating through it to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary, test WVTR value is calculated as follows:

$$\text{Test WVTR} = \frac{[(\text{grams weight loss over 24 hours}) \times 7571]}{24} (g/m^2/24 \text{ hours})$$

The relative humidity within the oven is not specifically controlled. Under predetermined set conditions of 100° F. and ambient relative humidity, the WVTR for CELGUARD 2500 materials has been determined to be 5000 g/m$^2$/24 hours. Accordingly, CELGUARD 2500 material is run as a control sample with each test. CELGUARD 2500 material is a 0.0025 cm thick film composed of a microporous polypropylene.

Z-Direction Composition Migration Test

This test determines the quantity of composition that remains on the target area of the bodyfacing surface of an absorbent article after a given period of time at a given temperature. Specifically, the purpose of the test is to compare the amount of composition present in the target zone on articles stored at a lower temperature with that present on articles stored at a higher temperature. The test simulates storage at elevated temperature conditions to which absorbent articles may be subjected. For example, such articles may be stored in the trunk of a vehicle or in a warehouse in a warm climate such as in a warehouse in Arizona in July or August. The z-direction migration loss is a measure of the composition migration after storage at 130° F. when compared to the composition migration at 73° F. after a fixed period of time. Thus, this test predicts the amount of composition that will be available on the bodyfacing surface of the article for transfer to the skin when the article is used as well as how quickly it will undesirably migrate away from or along the bodyfacing surface of the article in use. Specifically, the test is conducted as follows:

1. Ten (10) products having a composition applied to the topsheet or bodyside liner are obtained.
2. Five (5) products are placed in a controlled environment at a temperature of 73° F. and a relative humidity of 50% for a fixed period of time such as, for example, 28 days. The other five (5) products are placed in a controlled environment at a temperature of 130° F. and ambient humidity for the same period of time.
3. The products are removed from the controlled environment and a sample of the bodyside liner having a width of 3.75 inches and a length of 13 inches is removed from the center of each product.
4. The samples are then subjected to Soxhlet Extraction with Gravimetric Analysis (SEGA) as follows. The test apparatus includes a reboiler, chloroform vapor duct, cold water condenser, holding tank where the samples are placed and a chloroform recycle duct. The components of the test apparatus are conventional glassware well known to those skilled in the art. For example, the reboiler may include a 250 ml round bottom flask and the vapor duct can include an 85 ml soxhlet. A sample is placed in the holding tank and subjected to chloroform washing cycles for 2.5 hours. One hundred twenty-five milliliters of liquid chloroform is placed in the reboiler. The chloroform vaporizes and rises up through the vapor duct into the condenser having tap water therein that, in turn, causes the chloroform to liquefy and fall into the holding tank with the sample. The chloroform dissolves the composition from the liner sample. When the liquid chloroform reaches a high enough level, the recycle duct returns the chloroform/composition mixture to the reboiler. The temperature in the reboiler is controlled such that it is above the boiling point of the chloroform but below that of the composition such that only the chloroform vaporizes to start the process over again. One complete wash cycle takes approximately 15 minutes with about 75 milliliters of chloroform circulating through the liner sample in each cycle. Upon completion, the chloroform in the evaporator is evaporated utilizing a conventional vacuum evaporator such as a rotovap commercially available under the model number Buchi 011 RE 121 for a period of 4 minutes followed by placing the composition in an aluminum pan and heating on a hot plate with forced air circulation for an additional 30 minutes.
5. The residue (composition) remaining for each sample is then weighed. The amount of composition recovered from the products stored at 73° F. is then compared to the amount of composition recovered from the products stored at 130° F. to determine the stability of the composition formulation at high temperature.

The z-direction migration loss of the absorbent article is then determined as follows:

$$Z\text{-direction migration loss}(\%) = [(L_{73} - L_{130})/L_{73}] \times 100$$

wherein, $L_{73}$=average weight (g) of composition recovered per sample stored at 73° F.

$L_{130}$=average weight (g) of composition recovered per sample stored at 130° F.

CD-Direction Composition Migration Test

This test determines the quantity of composition that remains on the specific location where it is applied on the bodyfacing surface of an absorbent article after a given period of time at a given temperature. Specifically, the purpose of the test is to compare the amount of composition present in the applied location on the topsheet or bodyside liner with that present on the remaining portions of the bodyside liners of the articles after being stored at an elevated temperature. The test simulates storage at elevated temperature conditions to which absorbent articles may be subjected. For example, such articles may be stored in the trunk of a vehicle or in a warehouse in a warm climate such as in a warehouse in Arizona in July or August. The cd-direction migration loss is a measure of the lateral composition migration along the bodyfacing surface of the article after storage at 130° F. after a fixed period of time. Thus, this test predicts the amount of composition that will be available in the desired location on the bodyfacing surface of the article for transfer to the skin when the article is used as well as how quickly it will undesirably migrate away from or along the bodyfacing surface of the article in use.

Specifically, the test is conducted as follows:

1. Five (5) products having a composition applied to the bodyside liner in a specific pattern are obtained.
2. The products are placed in a controlled environment at a temperature of 130° F. and ambient humidity for a fixed period of time such as, for example, 28 days.
3. The products are removed from the controlled environment and the bodyside liner on each product is removed and dissected to remove the portion of the bodyside liner to which the composition was actually applied. For example, if the composition was applied as 4 continuous lines having a width of 0.25 inches with spaces of 0.75 inches in between, the 4 strips of bodyside liner would be removed.
4. The samples which include the portions of the bodyside liner to which the composition was applied are then grouped together and subjected to Soxhlet Extraction with Gravimetric Analysis (SEGA) as described above. The remaining portions of the bodyside liner are also grouped together and subjected to a separate SEGA extraction.
5. The residue (composition) remaining for each group is then weighed. The amount of composition recovered from the portions of the bodyside liner to which the composition was applied is then compared to the amount of composition recovered from the remaining portions of the bodyside liner to determine the stability of the composition at high temperature.

The cd-direction migration loss of the absorbent article is then determined as follows:

$$CD\text{-direction migration loss}(\%) = [L_{sp}/(L_a + L_{sp})] \times 100$$

wherein, $L_{sp}$=average weight (g) of composition recovered from the portions of the bodyside liner to which the composition was not applied per diaper $L_a$=average weight (g) of composition recovered from the portions of the bodyside liner to which the composition was applied per diaper The compositions of the present invention can be further described through examples of compositions considered to be within the scope of the present invention. The examples provided herein are intended to be representative of the present invention but are not intended to delineate the extent of the present invention. To the extent that amounts of individual components or total compositions are referred to in terms of "effective amounts", "effective amount" is understood to mean an amount that will have the desired effect of that component or composition. For example, an "effective amount" of one of the compositions of the invention is understood to mean an amount that, when applied to the bodyfacing or skin contacting surface of an article, will protect the barrier of the skin or reduce inflammatory response. Illustrative examples of the compositions of the invention are provided in Table 4. below.

TABLE 4

Formula (weight percent)

| | 1 | 2 | 3 | 4 |
|---|---|---|---|---|
| Petrolatum | 50% | 50% | 54% | 66% |
| Ozokerite Wax | 43% | 33% | 30% | — |
| Ethylene Vinyl Acetate Copolymer | 5% | 5% | 10% | 25% |
| Canadian Willowherb Extract | 1% | 10% | — | — |
| Yucca Gluauca-Root Extract | — | — | 5% | 8% |
| Sorbitan Monooleate | 1% | 1% | 1% | 1% |

| | 5 | 6 | 7 | 8 |
|---|---|---|---|---|
| Petrolatum | 55% | 55% | 45% | 40% |
| Microcrystalline Wax | 36.50% | 25% | 46.25% | 47% |
| Ethylene Vinyl Acetate Copolymer | 7% | 9% | 5% | 5% |
| Echinacea Extract | 1% | 10% | — | — |
| Green Tea Extract | — | — | 3% | 7% |
| Cetyl Dimethicone Copolymer | 0.50% | 1% | 0.75% | 1% |

| | 9 | 10 | 11 | 12 |
|---|---|---|---|---|
| Petrolatum | 40% | 42% | 47% | 68% |
| Cerasin | 35% | 30% | 25% | 22% |
| Ethylene Vinyl Acetate Copolymer | 5% | 5% | — | 3% |
| Propylene Glycol | 5% | 5% | — | — |
| Glycerin | 2% | 2% | — | — |
| Green Tea Extract | 3% | 6% | — | — |
| Green Tea Powder | — | — | 1% | 5% |
| BENTONE TN Organically Modified Clay | 10% | 10% | — | — |
| Silica | — | — | 2% | 2% |
| Zinc Oxide | — | — | 25% | — |

| | 13 | 14 | 15 | 16 |
|---|---|---|---|---|
| Petrolatum | 15% | 5% | — | — |
| Myristyl Myristate | 17% | 25% | 30% | 33% |
| Behenyl Benzoate | — | 35% | 20% | 30% |
| Behenyl Behenate | 50% | — | 5% | — |
| C12–C15 Alkyl Benzoate | — | 7% | 20% | 5% |
| Ethylene Vinyl Acetate Copolymer | 5% | 3% | 2% | 2% |
| Octyl Dodecanol | — | 10% | 5% | 5% |
| Silica | — | 2% | 3% | 5% |
| Avocado Oil | — | — | — | 5% |
| Green Tea Extract | 10% | — | — | — |
| Willowherb Extract | — | 10% | — | — |
| Yucca Gluauca Extract | — | — | 10% | — |
| Echinacea Extract | — | — | — | 10% |
| Sorbitan Trioleate | 3% | 3% | 5% | 5% |

| | 17 | 18 | 19 | 20 |
|---|---|---|---|---|
| Petrolatum | 64% | 53% | 48% | 40% |
| Cerasin | 5% | 10% | 25% | 30% |
| Glycerin | 5% | 8% | 10% | 3% |
| Sunflower Oil | 10% | — | — | — |
| Echium Oil | — | 5% | — | — |
| Borage Oil | — | — | 3% | — |
| Rapeseed Oil | — | — | — | 5% |
| Soy Sterol | 1% | — | — | — |
| Cholesterol | — | 3% | — | — |
| AVOCADIN | — | — | 5% | 10% |
| PROLIPID 141 Blend | 2% | 1% | — | — |
| Glyceryl Stearate SE | — | — | 3% | 2% |
| BENTONE TN Organically Modified Clay | 10% | 15% | — | — |
| Silica | — | — | 4% | 2% |
| Green Tea Extract | 3% | — | — | 2% |
| Willowherb Extract | — | 5% | — | — |
| Yucca Glauca Extract | — | — | 2% | 6% |

| | 21 | 22 | 23 | 24 |
|---|---|---|---|---|
| Mineral Oil | 45% | 50% | 63% | — |
| Behenyl Behenate | 53% | — | — | 25% |
| Ethylene Vinyl Acetate Copolymer | — | 40% | 15% | — |
| Borage Oil | — | — | — | 70% |
| Cetyl Esters | — | — | 15% | — |

TABLE 4-continued

Formula (weight percent)

| | | | | |
|---|---|---|---|---|
| Silica | 1% | — | 2% | 5% |
| Green Tea Extract | 1% | — | — | — |
| Green Tea Powder | — | 10% | — | — |
| Canadian Willowherb | — | — | 5% | — |

| | 25 | 26 | 27 |
|---|---|---|---|
| Petrolatum | 40% | 57% | 75% |
| Behenyl Behenate | — | 30% | — |
| Myristyl Myristate | — | 10% | — |
| Ethylene Vinyl Acetate Copolymer | 40% | 1% | 10% |
| Silica | 5% | 1% | 5% |
| LAPONITE synthetic clay | 15% | 1% | 10% |

| | 28 | 29 | 30 |
|---|---|---|---|
| Petrolatum | 90.7% | 8% | 50% |
| Avocado Oil | 1% | 80% | 10% |
| Soy Sterol | 0.2% | 1% | 10% |
| Ethylene Vinyl Acetate Copolymer | 8% | 10% | 20% |
| Green Tea Extract | 0.1% | 1% | 10% |

| | 31 | 32 | 33 |
|---|---|---|---|
| Petrolatum | 52% | 5% | 40% |
| Microcrystalline Wax | 40% | — | 5% |
| Polyethylene | — | 1% | 5% |
| Avocado Oil | 1% | 77% | 10% |
| Soy Sterol | 0.2% | 1% | 10% |
| Green Tea Extract | 0.1% | 1% | 10% |
| Silica | 1% | 5% | 10% |
| Bentonite | 5% | 10% | 10% |

| | 34 | 35 | 36 |
|---|---|---|---|
| Petrolatum | 79.9% | 60% | 60% |
| Microcrystalline Wax | — | — | 35% |
| Ethylene Vinyl Acetate Copolymer | 20.0% | 10% | — |
| Silica | — | — | — |
| Echinacea Extract | — | 10% | — |
| Yucca Glauca-Root Extract | — | — | 5% |
| Canadian Willowherb Extract | 0.1% | — | — |

The extracted botanical actives are available from numerous suppliers. For example, Echinacea extract is available from Bio-Botanica of Hauppauge, N.Y. Yucca Glauca extract is available from Brooks of South Plainfield, N.J. Canadian Willow Herb is available from Fytokem Products of Saskatchewan, Canada. Borage seed oil is available from Loders Croklaan of England. Green Tea extract and Green Tea powder are available from CRODA of Parsippany, N.J. and DRAGOCO of Totowa, N.J., respectively. The actual percentages of active botanicals in the extract composition are typically proprietary to the supplier of the extract.

As used herein, all recited ranges of amounts, temperatures, molecular weights and penetration hardnesses are intended to include all sub-ranges within the recited ranges, even though not specifically stated. The following examples are presented to provide a more detailed understanding of the invention.

In order to evaluate the efficacy of the compositions of the invention, a human skin culture was selected to model the response of the human epidermis. EPIDERM skin culture is a cornified, air-interfaced human skin culture. EPIDERM skin culture has multiple layers of progressively differentiated keratinocytes resembling human epidermis. EPIDERM EPI-200 skin culture can be purchased from MatTek Corporation of Ashland, MA. Experiments using EPIDERM skin culture are conducted in six well plates. Typically, five EPIDERM skin culture inserts are added to five of the six wells. Each well contains one milliliter of pre-warmed media that is the same as the EPIDERM skin culture media. The plates are then incubated in a 37° C., 5% $CO_2$ incubator for thirty minutes. After incubation, 15 microliters of test composition or control are applied to the surface of the EPIDERM skin culture after removing any residual media. For test compositions using a petrolatum base, the composition is applied using a positive-displacement pipettor and spread over the skin culture surface using a glass rod. The well plates, with the test compositions/control applied, are incubated in the 37° C., 5% $CO_2$ incubator for thirty minutes after which the underlying media is removed and replaced with fresh, pre-warmed media. Next, ten microliters of insult solution, either fecal protease or bile acid, are applied to the surface of the EPIDERM skin culture.

Infant feces contain proteases that include trypsin and chymotrypsin (See Haverback, B. J., Dyce, B. J., Gutentag, P. J., and Montgomery, D. W. (1963) Measurement of Trypsin and Chymotrypsin in Stool. Gasteroenterology 44:588–597; and Barbero, G. J., Sibinga, M. S., Marino, J. M., and Seibel, R. (1966) Stool Trypsin and Chymotrypsin. Amer. J. Dis. Child 112:536–540). For internal studies, infant feces were collected and the amount of total protease and trypsin activities determined for each of the fecal extracts. To prepare the extract, the feces were suspended in water and vigorously vortexed. After vortexing, the samples were held on ice prior to centrifugation at 15,000 times the force of gravity for 20 minutes. The supernatant was filtered through 0.22 micron cellulose acetate filters and stored at −80° C. until use. The amount of trypsin activity in the fecal extracts ranged from 0.4–402 μg/ml (n=19) as measured by the ability of the sample to hydrolyze a fluorescently-labeled trypsin peptide substrate (Boc-Gin-Ala-Arg-AMC HCl, BACHEM California, Incorporated, Torrance, Calif.). Total protease activity was measured as the ability of the sample to hydrolyze a fluorescent dye-labeled casein substrate (EnzChek Protease Assay Kit (E-6639), Molecular Probes, Eugene, Oreg.). Irritation induced in the EPIDERM skin culture correlated with the total protease as well as trypsin activities of the fecal extracts. Based on the literature sources as well as internal data, a trypsin-chymotrypsin insult was chosen as representative of a fecal insult, specifically a fecal protease insult, for the examples that follow.

The insult solution is prepared by diluting a 10 mg/ml stock solution in phosphate-buffered saline to a working concentration of 250 μg/ml. The base of the stock solution is 50 mM NaOAcetate, pH 5.5 and 0.15 M NaCl stored at −80° C. One milliliter of the stock protease insult solution contains 2558 USP units of trypsin and 298 USP units of chymotrypsin and is available from Specialty Enzymes, Inc. of Chino, Calif. The bile acid insult solution can be prepared by dissolving 65 mg of cholic acid, 62 mg of deoxycholic acid and 31 mg of chenodeoxycholic acid in 10 ml of phosphate-buffered saline. The bile acid insult components can also be purchased from Sigma Chemical Co. of St. Louis, Mo. Phosphate-buffered saline, pH 7.4 (hereinafter "PBS") can be purchased from Life Technologies of Rockville, Md.

After application of the insult solution, the well plates are incubated for six hours in the 37° C., 5% $CO_2$ incubator. At the end of six hours, the well plates are removed from the incubator, the underlying media is removed and stored at −80° C. The response of the EPIDERM skin culture to the test compositions/control and the insult solution is determined by measuring the amount of interleukin-1 alpha (IL-1α). Interleukin-1 alpha can be quantified using an Interleukin-1 alpha Quantikine Kit available from R&D Systems of Minneapolis, Minn. Interleukin-1 alpha measurements are converted to $Log_{10}$ for each of the treatments and the averages for each treatment are calculated. In order to determine the ability of the test compositions to reduce skin irritation caused by the biological insults, the percent mean reduction of IL-1α is calculated as follows:

$$\% \text{ mean reduction of IL-}1\alpha = 100 \times \frac{((PJ \text{ control} + \text{insult}) \text{ result} - (\text{test composition} + \text{insult}) \text{ result})}{((PJ \text{ control} + \text{insult}) \text{ result} - (PJ \text{ control} + PBS) \text{ result})}$$

(Test composition+insult) result=the measured amount of IL-1α from treatment with a test formulation+insult.

(PJ control+insult) result=the measured amount of IL-1α from a treatment with a control formulation+insult.

(PJ control+PBS) result=the measured amount of IL-1α from a treatment with a control formulation with PBS.

The greater the % mean reduction of IL-1α, the more effective a composition is at reducing irritation caused by the biological insult (proteases or bile acids).

In order to insure that the test compositions/control do not affect the viability of the EPIDERM skin culture, a MTT assay is run. The MTT dye is taken up by the cells. The reduction of the dye as a result of cellular metabolism can be used to measure the cytotoxicity of the test compositions. In order to confirm viability, inserts of the EPIDERM skin culture that have already been subjected to the test compositions and biological insults are removed from their media and are washed consecutively through immersion in three different beakers of PBS. Fresh PBS is used for each test composition or control being evaluated. The PBS is discarded onto paper towel. The EPIDERM skin culture inserts are then patted onto paper towel and placed into the wells of a 24 well plate containing 300 microliters of pre-warmed media. After all of the EPIDERM skin culture inserts are washed, they are transferred to new 24 well plates containing 300 microliters of the MTT reagent. The MTT reagent is thiazolyl blue having the formula 3-[4,5-Dimethylthiazol-2-yl]-2,5-diphenyltetrzoliumbromide. The plates are incubated for 2 hours in a 37° C., 5% $CO_2$ incubator. After incubation, the EPIDERM skin culture inserts are transferred to 24 well plates and are immersed in 2 milliliters of MTT extraction buffer. The extraction buffer extracts the MTT reagent from the cells. The 24 well plates are parafilmed, covered and placed in ZIPLOCK bags to reduce evaporation of the extraction buffer. The covered plates are rocked overnight in the dark. Following overnight rocking, the liquid in the EPIDERM skin culture inserts is decanted back into the wells. The contents of each well are mixed and a 200 microliter aliquot is then removed from each well and transferred to a 96 well plate. The optical density (OD) of the samples is measured at 570 nm using a spectrophotometer. Five hundred seventy nanometers is the optimal wavelength at which to measure the reduced form of MTT reagent. This reading is subtracted from a background reading at 650 nm to improve data quality. Percent viability of each test composition+insult relative to a negative petrolatum control+PBS is recorded as the Mean $OD_{test\ composition+insult}$ divided by the Mean $OD_{PJ\ control+PBS}$; the quotient then multiplied by 100.

As described above, various experiments were conducted to elucidate the benefits provided by the compositions of the invention. For example, EPIDERM skin culture studies were conducted to measure the reduction in IL-1α response between compositions of the invention and a fecal protease-induced irritation. The studies were conducted using three botanicals that are representative of the invention. The EPIDERM skin culture studies and associated MTT assays were conducted as already described herein and the results are as reported in Table 5. below.

TABLE 5

| Composition | Botanical Component of Composition | Mean Reduction of Interleukin-1 Alpha (percentage) | Viability (percentage) |
|---|---|---|---|
| A | 16.8% Echinacea | 0% | 99% |
| B | 16.8% Echinacea + AbilEM90 | 18% | 99% |
| C | 1% Yucca | 30%*; 26%* | 88%; 85% |
| D | 10% Yucca | 24%; 14% | 93%; 85% |
| E | 1% Willow Herb | 41%*; 36%* | 92%; 93% |
| F | 10% Willow Herb | 16%; 44% | 87%; 94% |

*indicates the composition had a significant mean difference from the PJ control + protease insult applying a Student's t-test with p < 0.05.

For each of the compositions in Table 5 (except Echinacea compositions), mean reduction of the inflammatory marker (IL-1α) for two experiments are shown. For each experiment, five replicates for each composition were evaluated. The IL-1α reduction results of Table 5 show that the compositions of the invention provide a skin protectant effect as evidenced by a reduced irritation response.

The reduction of IL-1α results were analyzed to statistically identify "outlier" results. The EPIDERM skin model is known to be variable with the variability attributed to differences in the culture, variation in the application of treatment and other uncontrollable factors. A statistical analysis technique was applied to identify when a result abnormally deviated from the rest of the data set. The irritation values were first converted to Log10 in order to make them more Gaussian (bell curve-shaped). After conversion, the values were analyzed for high or low value outliers; subsequently, the values were analyzed with a student's t-test to identify significant differences from the "control". The statistical analysis used to identify "outliers" is described on page 460 of the book, "Statistical Methods in Research and Production" edited by Owen L. Davies and Peter L. Goldsmith, published by Longman Group Limited, fourth revised edition published in 1984.

Interestingly, the Echinacea-containing composition required an emulsifying agent in order to provide efficacy in a petrolatum-based composition. Echinacea-containing compositions have been found to be effective at protecting the skin without an emulsifying agent when the composition is hydrophilic-based. The formulations for Compositions A–F are described in Table 6. below.

TABLE 6

| Component | A (Wt. %) | B (Wt. %) | C (Wt. %) | D (Wt. %) | E (Wt. %) | F (Wt. %) |
|---|---|---|---|---|---|---|
| White Fonoline Petrolatum | 83.2% | 81.52% | | | | |
| Petrolatum USP | | | 82.2% | 73.2% | 82.2% | 73.2% |
| Glycerin | | | 5.00% | 5.00% | 5.00% | 5.00% |
| Sunflower Oil | | | 10.00% | 10.00% | 10.00% | 10.00% |
| Soy Sterol | | | 0.80% | 0.80% | 0.80% | 0.80% |
| PROLIPID 141 blend | | | 1.00% | 1.00% | 1.00% | 1.00% |
| ABIL EM90 emulsifier | | 1.68% | | | | |
| Echinacea | 16.8% | 16.8% | | | | |
| Yucca | | | 1.00% | 10.00% | | |
| Willow Herb | | | | | 1.00% | 10.00% |

The compositions of the invention are also effective at protecting the skin from irritation induced by bile acids. EPIDERM skin culture studies were conducted to measure the reduction in IL-1α response between compositions of the invention and a bile acid-induced irritation. For this set of experiments, the oil miscible botanicals were blended in water +10% emulsifying wax. For the oil miscible compositions, 10% corn oil in water+10% emulsifying wax was used as the base control (analogous to petrolatum control of Table 5.). The results of the bile acid insult tests are provided in Table 7. below.

TABLE 7

| Composition | Botanical Component of Composition | Mean Reduction of Interleukin-1 Alpha (percentage) | Viability (percentage) |
|---|---|---|---|
| A | 1% Borage | 8% (5) | 95% |
| B | 10% Borage | 17% (5) | 101% |

The IL-α reduction results of Table 7. show that the compositions of the invention provide a skin protectant effect as evidenced by a reduced irritation response. The values in parentheses identify the number of replicates performed.

The compositions of the invention were also evaluated for their efficacy in a clinical study. The study was directed to measuring the erythema response to application of an "insult" and application of compositions of the invention. The control compositions were 100% petrolatum and 100% irritant mixture. The test compositions contained from 0.2% to 16.8% botanical; 0.8% preservatives/stabilizers including propyl paraben, methyl paraben, disodium EDTA, BHT and NaCl; and a balance of petrolatum. The test compositions containing Echinacea also included 1.68% of ABIL EM90 emulsifier.

The panel size for the clinical study was a minimum of 17 adult males and females. The control and test compositions were applied to areas on the backs of the adults. Up to sixteen sites on each adult's back were used for the study. Each test site was 2.5 cm in diameter. The irritant mixture included trypsin, chymotrypsin and bile acid in phosphate-buffered saline at a total concentration of 1500 µg/ml. The irritant mixture was either freshly prepared or refrigerated at −80° C. and defrosted at 37° C. just prior to use and then held in an ice bath. For each application of the irritant mixture, 0.2 ml of the irritant mixture was placed into a 25 mm HILLTOP chamber. Thirty milligram portions of the petrolatum control and test compositions were applied to the selected sites on each participant's back for twenty minutes. After application of the test compositions, the HILLTOP chambers with the irritant mixture were taped onto each test site and the petrolatum control site for 24 hrs.; an extra chamber was applied to a previously untreated site for 100% irritant mixture control. After 24 hrs., the HILLTOP chambers were removed. After an additional thirty minutes, experts evaluated the control and test sites for erythema, edema and dryness. The experts evaluated the sites using a scoring scale of 0 to 4 with 0.5 point intervals. The score given for each site was a combined evaluation for erythema, edema and dryness. The data recorded by the experts was analyzed using a Nonparametric Wilcoxon signed rank test statistical treatment to determine significant differences between two sites and, therefore, between two compositions. Each test site was treated with a particular composition and challenged daily with irritant mixture for up to ten days. When a test site reached a score of 2.5 or more, the test site was no longer treated or challenged. Participants returned daily (including weekends) for patch removal, evaluation and subsequent composition/irritant mixture application.

The lower the score, the more effective a composition was at preventing an irritation response. Table 8. below contains the irritation scores for the petrolatum control, the irritant control and three test compositions each containing 16.8% of a different botanical.

TABLE 8

| Number of Days After Application of Irritant Mixture | Petrolatum Control Site | Irritant Control Site | 16.8% Echinacea Test Composition | 16.8% Yucca Test Composition | 16.8% Willow Herb Test Composition |
|---|---|---|---|---|---|
| 1 | 0 | 0.1 | 0.1 | 0.1 | 0.1 |
| 2 | 0.6 | 0.7 | 0.5 | 0.3 | 0.3 |
| 3 | 0.6# | 1.1 | 0.6# | 0.5# | 0.5# |
| 4 | 0.9# | 1.5 | 0.8# | 1.1 | 0.8# |
| 5 | 1.1 | 1.6 | 1.0# | 1.1# | 1.0# |
| 6 | 1.4# | 1.9 | 1.1# | 1.4# | 1.2# |
| 7 | 1.4# | 1.9 | 1.2# | 1.3# | 1.4# |
| 8 | 1.9# | 2.2 | 1.6# | 1.4# | 1.7# |
| 9 | 2.1# | 2.3 | 1.8# | 1.7# | 2.0# |
| 10 | 2.2# | 2.2 | 1.8# | 1.9# | 2.0# |

A number sign ("#") indicates that the result was significantly different from the irritant control at a 95% level of confidence. The statistical analysis performed factored in the number of participants at any given time during the study. The number of participants varied between compositions because participants were dropped if their erythema scores reached the upper limit of 2.5. The results in Table 8. show that each of the test compositions resulted in lower irritation scores versus the irritant control from Day 3 onward. Consequently, the compositions of the invention provide a benefit to the skin when the skin is exposed to biological insults such as fecal proteases and bile acids. The results showed the additional benefits associated with using an extracted botanical active over using petrolatum alone. In Table 9. below, the irritation scores for four different Echinacea test compositions are provided for comparison with the scores for a petrolatum control and an irritant control.

TABLE 9

| Number of Days After Application of Irritant Mixture | Petrolatum Control Site | Irritant Control Site | 0.2% Echinacea Test Composition | 1.7% Echinacea Test Composition | 7.5% Echinacea Test Composition | 16.8% Echinacea Test Composition |
|---|---|---|---|---|---|---|
| 1 | 0.1 | 0.6 | 0.21# | 0.1# | 0.3# | 0.2# |
| 2 | 0.2 | 0.9 | 0.3# | 0.1# | 0.3# | 0.4# |
| 3 | 0.5 | 1.2 | 0.6# | 0.3# | 0.6 | 0.7 |
| 4 | 0.6 | 1.7 | 0.8# | 0.5# | 0.3# | 0.9# |
| 5 | 1.4 | 1.9 | 1.0# | 1.0*# | 1.2# | 1.3# |
| 6 | 1.7 | 2.1 | 1.4# | 1.3# | 1.4# | 1.4# |
| 7 | 2.0 | 2.1 | 1.6# | 1.5# | 1.6# | 1.8# |
| 8 | 2.0 | 2.1 | 1.6# | 1.2*# | 1.8# | 1.6# |
| 9 | 1.8 | 2.3 | 1.6# | 1.1# | 1.9# | 1.6# |
| 10 | 1.9 | 2.4 | 1.5# | 1.4*# | 2.0# | 1.7# |

And asterisk ("*") after a value indicates a significant difference from the petrolatum control. A number sign ("#") after a value indicates a significant difference from the irritant control at a confidence level of 95%. The statistical analysis performed factored in the number of participants at any given time during the study. The number of participants varied between compositions because participants were dropped if their erythema scores reached the upper limit of 2.5. The irritation score results in Table 9. show that each of the Echinacea test compositions reduced skin irritation from day 1 of the study forward compared with the irritant control. Therefore, the compositions of the invention provide a benefit to skin that is exposed to biological insults such as fecal proteases and bile acids. The results show the benefits associated with using compositions of the invention over using petrolatum alone.

In order to demonstrate that compositions of the invention do indeed transfer from the liner or other bodyfacing material of an absorbent article, studies were conducted to quantify the amount of composition transferred from the liner of a diaper to a TEGADERM skin patch. The studies were conducted on infants wearing a "Size 3" HUGGIES diaper fitting a child ranging in weight from about 16 to about 28 pounds. The children participating in the studies wore the test diapers for a period of 6 hours; therefore, the amount of composition transferred to a TEGADERM skin patch over a period of 6 hours was measured. The children were first evaluated for any type of diaper rash or skin irritation and, if such irritation was present, those children did not participate. Prior to application of the diapers being evaluated in the studies, each participating child's buttocks were wiped with a HUGGIES NATURAL CARE unscented wet wipe. A 1.75 square inch TEGADERM adhesive skin patch was then applied to each participating child's buttocks in such a way that the entire skin patch would be in contact with the bodyfacing surface of the bodyside liner of the diaper. Next, a disposable diaper having a composition of the invention on the bodyfacing surface of the bodyside liner was applied to each child. The children wore the test diapers for six hours, however, between the three and 4 hour time points, the children's' caregivers changed their diapers and applied a new test diaper. After six hours, the diapers and the TEGADERM skin patches were removed. The TEGADERM skin patches were removed by first lifting up one corner of the patch and then gently pulling back the patch to remove. The skin patches were placed in individual vials using tweezers to avoid contamination. The skin patches were then analyzed for the amount of composition taken up from the bodyside liners of the diapers. The amount of composition taken up was determined by extracted the composition from the skin patches and then quantifying the amount using gravimetric analysis. Descriptions of the compositions tested and the results of the transfer studies are reported below in Table 10.

TABLE 10

| Diaper Sample Number | Composition Applied to Bodyside Liner (amounts are % by weight) | Add-On Level of Composition to Bodyside Liner (grams/18" of diaper length) | Average Amount of Composition Transferred to Skin Patch (mg/cm$^2$) | Relative Standard Deviation |
|---|---|---|---|---|
| 1[a] | Petrolatum, 42.2% Ozokerite Wax, 40% Soy Sterol, 0.80% Sunflower Oil, 10% PROLIPID 141 blend, 1% Glycerin, 5% Sorbitan Monooleate, 0.85% Polysorbate 80, 0.15% | 0.2 | 0.104 | 23% |
| 2[b] | Petrolatum, 42.2% Ozokerite Wax, 40% Soy Sterol, 0.80% Sunflower Oil, 10% PROLIPID 141 blend, 1% Glycerin, 5% Sorbitan Monooleate, 0.85% Polysorbate 80, 0.15% | 0.2 | 0.105 | 18.3% |
| 3[c] | Petrolatum, 60% Ozokerite Wax, 40% | 0.34 | 0.074 | 41.2% |
| 4[c] | Petrolatum, 42.2% Ozokerite Wax, 40% Soy Sterol, 0.80% Sunflower Oil, 10% PROLIPID 141 blend, 1% Glycerin, 5% Sorbitan Monooleate, 0.85% Polysorbate 80, 0.15% | 0.24 | 0.128 | 23.7% |
| 5[c] | Petrolatum, 41% Ozokerite Wax, 38.2% Soy Sterol, 0.80% Sunflower Oil, 10% PROLIPID 141 blend, 1% Glycerin, 5% Sorbitan Monooleate, 0.85% Polysorbate 80, 0.15% Dimethicone, 2% Alkyl Silicone Wax, 1% | 0.24 | 0.084 | 48.9% |

TABLE 10-continued

| Diaper Sample Number | Composition Applied to Bodyside Liner (amounts are % by weight) | Add-On Level of Composition to Bodyside Liner (grams/18" of diaper length) | Average Amount of Composition Transferred to Skin Patch (mg/cm$^2$) | Relative Standard Deviation |
|---|---|---|---|---|
| 6[c] | Petrolatum, 42.2%<br>Ozokerite Wax, 40%<br>Soy Sterol, 0.80%<br>Sunflower Oil, 10%<br>PROLIPID 141 blend, 1%<br>Glycerin, 5%<br>Sorbitan Monooleate, 0.85%<br>Polysorbate 80, 0.15% | 0.34 | 0.173 | 33.2% |
| 7[a] | Petrolatum, 42.2%<br>Ozokerite Wax, 40%<br>Soy Sterol, 0.80%<br>Sunflower Oil, 10%<br>PROLIPID 141 blend, 1%<br>Glycerin, 5%<br>Sorbitan Monooleate, 0.85%<br>Polysorbate 80, 0.15% | 0.10 | 0.114 | 17.5% |
| 8[e] | Petrolatum, 41%<br>Ozokerite Wax, 38.2%<br>Soy Sterol, 0.80%<br>Sunflower Oil, 10%<br>PROLIPID 141 blend, 1%<br>Glycerin, 5%<br>Sorbitan Monooleate, 0.85%<br>Polysorbate 80, 0.15%<br>Dimethicone, 2%<br>Alkyl Silicone Wax, 1% | 0.28 | 0.103 | 38.8% |
| 9[d] | Petrolatum, 42.2%<br>Ozokerite Wax, 40%<br>Soy Sterol, 0.80%<br>Sunflower Oil, 10%<br>PROLIPID 141 blend, 1%<br>Glycerin, 5%<br>Sorbitan Monooleate, 0.85%<br>Polysorbate 80, 0.15% | 0.20 | 0.246 | 16.7% |
| 10[e] | Petrolatum, 42.2%<br>Ozokerite Wax, 40%<br>Soy Sterol, 0.80%<br>Sunflower Oil, 10%<br>PROLIPID 141 blend, 1%<br>Glycerin, 5%<br>Sorbitan Monooleate, 0.85%<br>Polysorbate 80, 0.15% | 0.18 | 0.258 | 10.0% |

[a] = bodyside liner was a spunbond material and the composition was applied by spray application
[b] = bodyside liner was a dual layer liner and the composition was applied by spray application
[c] = bodyside liner was a dual layer liner and composition was applied by slot coating
[d] = composition was applied in a pinstripe pattern using a hybrid of spray application and slot coating
[e] = bodyside liner was a spunbond material and composition was applied by slot coating The average amount of composition transferred to the skin patch is based on a sample size of twenty for each diaper sample. The results in Table 10. show that the compositions of the invention do indeed transfer from the bodyside liner of the diaper to the skin of the wearer of the absorbent article. While the compositions used in these transfer studies did not contain extracted botanical actives, it is expected that similar composition with extracted botanical actives would transfer to the skin similarly. The extracted botanical actives are not expected to impact transfer of the composition from the bodyside liner to the skin.

The preceding test results representatively illustrate that the compositions of the present invention protect the skin barrier and subdue the inflammatory response of the skin when the skin is exposed to biological insults. The compositions are efficacious when applied to the skin directly and when transferred to the skin from a liner material such as would be a component of an absorbent article.

While the invention has been described in detail with respect to the specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

We claim:

1. An absorbent article comprising:
   (a) an outer cover;
   (b) a liquid permeable bodyside liner that defines a bodyfacing surface and that is connected in superposed relation to the outer cover;
   (c) an absorbent body that is located between the bodyside liner and the outer cover; and
   (d) a composition on at least a portion of the bodyfacing surface of the bodyside liner that includes from about 50 to about 95 percent by weight of emollient, from about 1 to about 40 percent by weight of viscosity enhancer and from about 0.1 to about 10 percent by weight of extracted botanical active.

2. The absorbent article of claim 1, wherein the composition has a high shear viscosity less than about 5,000 centipoise at a temperature greater than about 60° C. and has a low shear viscosity greater than about 50,000 centipoise at a temperature of about 55° C.

3. The absorbent article of claim 1, wherein the emollient of the composition is selected from petrolatum, vegetable based oils, mineral oils, dimethicone, lanolin, glycerol esters, alkoxylated carboxylic acids, alkoxylated alcohols, fatty alcohols and mixtures thereof.

4. The absorbent article of claim 1, wherein the viscosity enhancer of the composition is selected from polyolefin resins, lipophilic/oil thickeners, ethylene/vinyl acetate copolymers, organically modified clays, polyethylene, silica, silica silylate, silica methyl silylate, colloidal silicone dioxide, alkyl hydroxy ethyl cellulose, microcrystalline wax, shellac wax, hexadecyl cosanyl hexacosanate, C20–C40 alkyl hydroxystearyl stearate, glycol montanate, ozokerite wax, polyperfluoromethylisopropylether montan wax and mixtures thereof.

5. The absorbent article of claim 1, wherein the extracted botanical active of the composition is selected from echinacea, yucca, willow herb, green tea, black tea, oolong tea, Chinese tea and mixtures thereof.

6. The absorbent article of claim 1, wherein the composition further includes from about 5 to about 48 percent by weight of solidifying agent.

7. The absorbent article of claim 6 wherein the solidifying agent of the composition is selected from beeswax, behenyl behenate, behenyl benzoate, branched esters, candelilla wax, carnauba wax, synthetic carnauba wax, PEG-12 carnauba wax, cerasin, microcrystalline wax, hydrogenated microcrystalline wax, hexadecylcosanyl hexacosanate, polyperfluoromethylisopropylether montan wax, alkylmethylsiloxanes, glycol montanate, jojoba wax, lanolin wax, ozokerite, paraffin, synthetic paraffin, polyethylene, C20–C40 alkyl hydroxystearyl stearate, C30 alkyl dimethicone, cetyl esters, zinc stearate, shellac wax, hydrogenated cottonseed oil, hydrogenated squalene, hydrogenated jojoba oil and mixtures thereof.

8. The absorbent article of claim 1 wherein the composition further includes from about 0.1 to about 48 percent by weight of natural fats or oils.

9. The absorbent article of claim 8, wherein the natural fat or oil is selected from Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lauric Acid, Palmitic Acid, Stearic Acid, Linoleic Acid, Stearyl Alcohol, Lauryl Alcohol, Myristyl Alcohol, Behenyl Alcohol, Rose Hip Oil, Calendula Oil, Chamomile Oil, Eucalyptus Oil, Juniper Oil, Sandlewood Oil, Tea Tree Oil, Sunflower Oil, Soybean Oil and mixtures thereof.

10. The absorbent article of claim 1 wherein the composition further includes from about 0.1 to about 10 percent by weight of sterols or sterol derivatives.

11. The absorbent article of claim 10, wherein the sterol or sterol derivative is selected from cholesterol, sitosterol, stigmasterol, and ergosterol, as well as, C10–C30 cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, sterol esters and mixtures thereof.

12. The absorbent article of claim 1, wherein the composition further includes from about 0.5 to about 20 percent by weight of a rheology modifier.

13. The absorbent article of claim 12, wherein the rheology modifier is selected from silica, silica silylate, silica methyl silylate, quaternary starch compounds, quaternary modified clays, organically modified clays and mixtures thereof.

14. The absorbent article of claim 13 wherein the composition further comprises from about 1 to about 20 percent by weight of clay selected from natural clays and synthetic analogs of natural clays.

15. An absorbent article comprising:
(a) an outer cover;
(b) a liquid permeable bodyside liner that defines a bodyfacing surface and that is connected in superposed relation to the outer cover;
(c) an absorbent body that is located between the bodyside liner and the outer cover; and
(d) a composition on at least a portion of the bodyfacing surface of the bodyside liner that includes from about 50 to about 98 percent by weight of emollient, from about 1 to about 40 percent by weight of viscosity enhancer and from about 0.1 to about 10 percent by weight of extracted botanical active selected from echinacea, yucca, willow herb, green tea, black tea, oolong tea, Chinese tea and mixtures thereof.

16. An absorbent article comprising:
(a) an outer cover;
(b) a liquid permeable bodyside liner that defines a bodyfacing surface and that is connected in superposed relation to the outer cover;
(c) an absorbent body that is located between the bodyside liner and the outer cover; and
(d) a composition on at least a portion of the bodyfacing surface of the bodyside liner that includes from about 60 to about 95 percent by weight of emollient, from about 0.5 to about 20 percent by weight of rheology modifier and from about 1 to about 20 percent by weight of clay selected from natural clays and synthetic analogs of natural clays.

17. The absorbent article of claim 16, wherein the rheology modifier is selected from silica, organically modified clays, silica silylate, silica methyl silylate, quaternary starch compounds, quaternary modified clays and mixtures thereof.

18. The absorbent article of claim 16 wherein the clay is selected from montmorrillonite, bentonite, hectorite, stevensite, beidellite, saponite, magnesium aluminum silicate and mixtures thereof.

19. An absorbent article comprising:
(a) an outer cover;
(b) a liquid permeable bodyside liner that defines a bodyfacing surface and that is connected in superposed relation to the outer cover;
(c) an absorbent body that is located between the bodyside liner and the outer cover; and
(d) a composition on at least a portion of the bodyfacing surface of the bodyside liner that includes from about 20 to about 95 percent by weight of emollient, from about 0.5 to about 20 percent by weight of rheology modifier and from about 1 to about 25 percent by weight of zinc oxide.

20. An absorbent article comprising:
(a) an outer cover;
(b) a liquid permeable bodyside liner that defines a bodyfacing surface and that is connected in superposed relation to the outer cover;
(c) an absorbent body that is located between the bodyside liner and the outer cover; and
(d) a composition on at least a portion of the bodyfacing surface of the bodyside liner that includes from about 0.1 to about 95 percent by weight of natural fats or oils, from about 0.1 to about 10 percent by weight of sterols or sterol derivatives, from about 1 to about 95 percent by weight of emollient, from about 1 to about 40 percent by weight of viscosity enhancer and from about 0.1 to about 10 percent by weight of extracted botanical active.

21. The absorbent article of claim 20, wherein the composition has a melting point from about 32° C. to about 100° C.

22. The absorbent article of claim 20, wherein the composition has a high shear viscosity less than about 5,000 centipoise at a temperature greater than about 60° C. and has a low shear viscosity greater than about 50,000 centipoise at a temperature of about 55° C.

23. The absorbent article of claim 20, wherein the composition has a penetration hardness of from about 5 millimeters to about 365 millimeters at 25° C.

24. The absorbent article of claim 20, wherein the composition is on the bodyfacing surface in an amount of from about 0.1 grams per meter squared (g/m2) to about 30 g/m2.

25. The absorbent article of claim 20, wherein the natural fat or oil of the composition is selected from Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lauric Acid, Palmitic Acid, Stearic Acid, Linoleic Acid, Stearyl Alcohol, Lauryl Alcohol, Myristyl Alcohol, Behenyl Alcohol, Rose Hip Oil, Calendula Oil, Chamomile Oil, Eucalyptus Oil, Juniper Oil, Sandlewood Oil, Tea Tree Oil, Sunflower Oil, Soybean Oil and mixtures thereof.

26. The absorbent article of claim 20, wherein the sterol or sterol derivative of the composition is selected from cholesterol, sitosterol, stigmasterol, and ergosterol, as well as, C10–C30 cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, sterol esters and mixtures thereof.

27. The absorbent article of claim 20, wherein the emollient of the composition is selected from petrolatum, vegetable based oils, mineral oils, dimethicone, lanolin, glycerol esters, alkoxylated carboxylic acids, alkoxylated alcohols, fatty alcohols and mixtures thereof.

28. The absorbent article of claim 20, wherein the viscosity enhancer of the composition is selected from polyolefin resins, lipophilic/oil thickeners, ethylene/vinyl acetate copolymers, organically modified clays, polyethylene, silica, silica silylate, silica methyl silylate, colloidal silicone dioxide, alkyl hydroxy ethyl cellulose, microcrystalline wax, shellac wax, hexadecyl cosanyl hexacosanate, C20–C40 alkyl hydroxystearyl stearate, glycol montanate, ozokerite wax, polyperfluoromethylisopropylether montan wax and mixtures thereof.

29. The absorbent article of claim 20, wherein the extracted botanical active of the composition is selected from selected from echinacea, yucca, willow herb, green tea, black tea, oolong tea, Chinese tea and mixtures thereof.

30. The absorbent article of claim 20, wherein the composition further includes from about 5 to about 95 percent by weight of a solidifying agent.

31. The absorbent article of claim 30, wherein the solidifying agent of the composition is selected from beeswax, behenyl behenate, behenyl benzoate, branched esters, candelilla wax, carnauba wax, synthetic carnauba wax, PEG-12 carnauba wax, cerasin, microcrystalline wax, hydrogenated microcrystalline wax, hexadecylcosanyl hexacosanate, polyperfluoromethylisopropylether montan wax, alkylmethylsiloxanes, glycol montanate, jojoba wax, lanolin wax, ozokerite, paraffin, synthetic paraffin, polyethylene, C20–C40 alkyl hydroxystearyl stearate, C30 alkyl dimethicone, cetyl esters, zinc stearate, shellac wax, hydrogenated cottonseed oil, hydrogenated squalene, hydrogenated jojoba oil and mixtures thereof.

32. The absorbent article of claim 20, wherein the composition further includes from about 0.5 to about 20 percent by weight of a rheology modifier.

33. The absorbent article of claim 32, wherein the rheology modifier is selected from silica, silica silylate, silica methyl silylate, quaternary starch compounds, quaternary modified clays, organically modified clays and mixtures thereof.

34. The absorbent article of claim 32 wherein the composition further includes from about 1 to about 20 percent by weight of clay selected from natural clays and synthetic analogs of natural clays.

35. An absorbent article comprising:
(a) an outer cover;
(b) a liquid permeable bodyside liner that defines a bodyfacing surface and that is connected in superposed relation to the outer cover;
(c) an absorbent body that is located between the bodyside liner and the outer cover; and
(d) a composition on at least a portion of the bodyfacing surface of the bodyside liner that includes from about 0.1 to about 95 percent by weight of natural fats or oils, from about 0.1 to about 10 percent by weight of sterols or sterol derivatives, from about 1 to about 95 percent by weight of emollient, from about 1 to about 40 percent by weight of viscosity enhancer and from about 0.1 to about 10 percent by weight of extracted botanical active selected from echinacea, yucca, willow herb, green tea, black tea, oolong tea, Chinese tea and mixtures thereof.

36. An absorbent article comprising:
(a) an outer cover;
(b) a liquid permeable bodyside liner that defines a bodyfacing surface and that is connected in superposed relation to the outer cover;
(c) an absorbent body that is located between the bodyside liner and the outer cover; and
(d) a composition on at least a portion of the bodyfacing surface of the bodyside liner that includes from about 0.1 to about 95 percent by weight of natural fats or oils, from about 0.1 to about 10 percent by weight of sterols or sterol derivatives, from about 1 to about 95 percent by weight of emollient, from about 0.5 to about 20 percent by weight of rheology modifier and from about 1 to about 20 percent by weight of clay selected from natural clays and synthetic analogs of natural clays.

37. The absorbent article of claim 36, wherein the rheology modifier is selected from silica, organically modified clays, silica silylate, silica methyl silylate, quaternary starch compounds, quaternary modified clays and mixtures thereof.

38. The absorbent article of claim 36 wherein the clay is selected from montmorrillonite, bentonite, hectorite, stevensite, beidellite, saponite, magnesium aluminum silicate and mixtures thereof.

39. An absorbent article comprising:
(a) an outer cover;
(b) a liquid permeable bodyside liner that defines a bodyfacing surface and that is connected in superposed relation to the outer cover;
(c) an absorbent body that is located between the bodyside liner and the outer cover; and
(d) a composition on at least a portion of the bodyfacing surface of the bodyside liner that includes from about 0.1 to about 95 percent by weight of natural fats or oils, from about 0.1 to about 10 percent by weight of sterols or sterol derivatives, from about 1 to about 95 percent by weight of emollient, from about 0.5 to about 20 percent by weight of rheology modifier and from about 1 to about 25 percent by weight of zinc oxide.

40. A method of applying a composition to a bodyfacing surface of a bodyside liner of an absorbent article comprising the steps of:
(a) heating a composition comprising an emollient, a viscosity enhancer and from about 0.1 to about 10 percent by weight of an extracted botanical active selected from echinacea, yucca, willow herb, green tea, black tea, oolong tea, Chinese tea and mixtures thereof, to a temperature above the melting point of the composition, the composition having a melting point of from about 32° C. to about 100° C.;
(b) applying the composition to the bodyfacing surface of a bodyside liner of an absorbent article; and
(c) resolidifying the composition.

41. The method of claim 40, wherein after the step of resolidification, the composition has a viscosity of greater than about 50,000 centipoise.

42. The method of claim 40, wherein after the step of heating, the composition is applied by spraying.

43. The method of claim 40, wherein after the step of heating, the composition is applied by slot coating.

44. The method of claim 40, wherein after the step of heating, the composition is applied by printing.

45. The method of claim 40, wherein the emollient of the composition is from about 50 to about 95 percent by weight of the composition and is selected from petrolatum, vegetable based oils, mineral oils, dimethicone, lanolin, glycerol esters, alkoxylated carboxylic acids, alkoxylated alcohols, fatty alcohols and mixtures thereof.

46. The method of claim 40, wherein the viscosity enhancer of the composition is from about 1 to about 40 percent by weight of the composition and is selected from polyolefin resins, lipophilic/oil thickeners, ethylene/vinyl acetate copolymers, organically modified clays, polyethylene, silica, silica silylate, silica methyl silylate, colloidal silicone dioxide, alkyl hydroxy ethyl cellulose, microcrystalline wax, shellac wax, hexadecyl cosanyl hexacosanate, C20–C40 alkyl hydroxystearyl stearate, glycol montanate, ozokerite wax, polyperfluoromethylisopropylether montan wax and mixtures thereof.

47. The method of claim 40, wherein the composition further includes from about 5 to about 95 percent by weight of solidifying agent selected from beeswax, behenyl behenate, behenyl benzoate, branched esters, candelilla wax, carnauba wax, synthetic carnauba wax, PEG-12 carnauba wax, cerasin, microcrystalline wax, hydrogenated microcrystalline wax, hexadecylcosanyl hexacosanate, polyperfluoromethylisopropylether montan wax, alkylmethylsiloxanes, glycol montanate, jojoba wax, lanolin wax, ozokerite, paraffin, synthetic paraffin, polyethylene, C20–C40 alkyl hydroxystearyl stearate, C30 alkyl dimethicone, cetyl esters, zinc stearate, shellac wax, hydrogenated cottonseed oil, hydrogenated squalene, hydrogenated jojoba oil and mixtures thereof.

48. The method of claim 40 wherein the composition further includes from about 0.1 to about 95 percent by weight of natural fats or oils selected from Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lauric Acid, Palmitic Acid, Stearic Acid, Linoleic Acid, Stearyl Alcohol, Lauryl Alcohol, Myristyl Alcohol, Behenyl Alcohol, Rose Hip Oil, Calendula Oil, Chamomile Oil, Eucalyptus Oil, Juniper Oil, Sandlewood Oil, Tea Tree Oil, Sunflower Oil, Soybean Oil and mixtures thereof.

49. The method of claim 40 wherein the composition further includes from about 0.1 to about 10 percent by weight of sterols or sterol derivatives selected from cholesterol, sitosterol, stigmasterol, and ergosterol, as well as, C10–C30 cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, sterol esters and mixtures thereof.

50. The method of claim 40, wherein the composition further includes from about 0.5 to about 20 percent by weight of a rheology modifier selected from silica, silica silylate, silica methyl silylate, quaternary starch compounds, quaternary modified clays, organically modified clays and mixtures thereof.

51. A method for protecting the skin barrier on a skin surface of a user, comprising the steps of:
a) contacting the skin surface of the user with a bodyfacing surface of a liner material, the bodyfacing surface having a composition comprising an emollient, a viscosity enhancer and an extracted botanical active;
b) maintaining the bodyfacing surface in contact with the skin surface for a sufficient amount of time to transfer the composition to the skin surface; and
c) repeating the contact of the skin surface with the bodyfacing surface of the liner material for a sufficient period of time to protect the skin barrier, wherein the composition comprises from about 50 to about 95 percent by weight of an emollient, from about 1 to about 40 percent by weight of a viscosity enhancer and from about 0.1 to about 10 percent by weight of an extracted botanical active selected from echinacea, yucca, willow herb, green tea, black tea, oolong tea, Chinese tea and mixtures thereof.

52. The method of claim 51, wherein the composition has a melting point from about 32° C. to about 100° C.

53. The method of claim 51, wherein the composition has a high shear viscosity less than about 5,000 centipoise at a temperature greater than about 60° C. and has a low shear viscosity greater than about 50,000 centipoise at a temperature of about 55° C.

54. The method of claim 51, wherein the composition has a penetration hardness of from about 5 to about 365 millimeters at 25° C.

* * * * *